US011744594B2

(12) United States Patent
Larsen et al.

(10) Patent No.: US 11,744,594 B2
(45) Date of Patent: Sep. 5, 2023

(54) SPACE FILLING DEVICES

(71) Applicant: W.L. Gore & Associates, Inc., Newark, DE (US)

(72) Inventors: Coby C. Larsen, Flagstaff, AZ (US); Brandon A. Lurie, Flagstaff, AZ (US); Steven J. Masters, Flagstaff, AZ (US); Thomas R. McDaniel, Flagstaff, AZ (US); Stanislaw L. Zukowski, Flagstaff, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 1124 days.

(21) Appl. No.: 14/080,739

(22) Filed: Nov. 14, 2013

(65) Prior Publication Data
US 2014/0142610 A1    May 22, 2014

Related U.S. Application Data

(60) Provisional application No. 61/798,791, filed on Mar. 15, 2013, provisional application No. 61/727,458, filed on Nov. 16, 2012.

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12172* (2013.01);
(Continued)

(58) Field of Classification Search
CPC ........ A61B 17/12172; A61B 17/12122; A61B 2017/00579; A61B 2017/00575; A61B 2017/00597; A61B 2017/00606
See application file for complete search history.

(56) References Cited

U.S. PATENT DOCUMENTS 3,874,388 A    4/1975  King
4,762,129 A    8/1988  Bonzel
(Continued)

FOREIGN PATENT DOCUMENTS

CN    1725988 A    1/2006
EP    2478868 A1    7/2012
(Continued)

OTHER PUBLICATIONS

Invitation to Pay Additional Fees and Partial International Search for PCT/US2013/070371, 5 pages, 2014.
(Continued)

*Primary Examiner* — Alexander J Orkin
(74) *Attorney, Agent, or Firm* — GREENBERG TRAURIG, LLP

(57) ABSTRACT

A device includes a plurality of elongate members, an occlusive component, and a support component. The occlusive component includes a plurality of first features each defined by a first portion of a respective elongate member. The support component includes a plurality of second features each defined by a second portion of the respective elongate member. A first termination element is defined by proximal end portions of the plurality of elongate members and located near a proximal end of the device, and a second termination element is defined by distal end portions of the plurality of elongate members and located near a distal end of the device. One or more anchor elements include a frame attachment portion and an anchor portion, the frame attachment portion including a first portion of a fixation elongate element wrapped around an elongate member, and the anchor portion including an anchor feature.

7 Claims, 30 Drawing Sheets

(52) U.S. Cl.
CPC ............ *A61B 17/12177* (2013.01); *A61B 2017/00526* (2013.01); *A61B 2017/00575* (2013.01); *A61B 2017/00579* (2013.01); *A61B 2017/00592* (2013.01); *A61B 2017/00597* (2013.01)

(56) References Cited

U.S. PATENT DOCUMENTS

| | | | |
|---|---|---|---|
| 5,040,548 A | 8/1991 | Yock | |
| 5,061,273 A | 10/1991 | Yock | |
| 5,476,589 A | 12/1995 | Bacino | |
| 5,486,193 A | 1/1996 | Bourne et al. | |
| 5,607,463 A | 3/1997 | Schwartz et al. | |
| 5,626,599 A | 5/1997 | Bourne et al. | |
| 5,733,294 A * | 3/1998 | Forber | A61B 17/12022 606/151 |
| 5,814,405 A | 9/1998 | Branca et al. | |
| 6,080,182 A | 6/2000 | Shaw et al. | |
| 6,165,197 A | 12/2000 | Yock | |
| 6,171,329 B1 * | 1/2001 | Shaw | A61B 17/0057 606/151 |
| 6,214,025 B1 * | 4/2001 | Thistle | A61F 2/01 606/200 |
| 6,254,632 B1 | 7/2001 | Wu et al. | |
| 6,355,052 B1 * | 3/2002 | Neuss | A61B 17/0057 606/213 |
| 6,488,706 B1 | 12/2002 | Solymar | |
| 6,506,204 B2 * | 1/2003 | Mazzocchi | A61B 17/0057 606/200 |
| 6,537,310 B1 | 3/2003 | Palmaz et al. | |
| 6,589,265 B1 | 7/2003 | Palmer | |
| D493,223 S | 7/2004 | Solymar | |
| 7,704,268 B2 * | 4/2010 | Chanduszko | A61B 17/0057 606/213 |
| 8,246,762 B2 | 8/2012 | Janko et al. | |
| 9,700,441 B2 | 7/2017 | Cully | |
| 2001/0032013 A1 | 10/2001 | Marton | |
| 2002/0111647 A1 * | 8/2002 | Khairkhahan | A61B 17/12172 606/200 |
| 2003/0023265 A1 | 1/2003 | Forber | |
| 2003/0149463 A1 | 8/2003 | Solymar et al. | |
| 2003/0236570 A1 * | 12/2003 | Cook | A61F 2/848 623/1.36 |
| 2004/0073242 A1 * | 4/2004 | Chanduszko | A61B 17/0057 606/157 |
| 2004/0148015 A1 | 7/2004 | Lye et al. | |
| 2004/0176799 A1 * | 9/2004 | Chanduszko | A61B 17/0057 606/213 |
| 2005/0273119 A1 * | 12/2005 | Widomski | A61B 17/0057 606/151 |
| 2006/0122646 A1 | 6/2006 | Corcoran | |
| 2006/0217761 A1 * | 9/2006 | Opolski | A61B 17/0057 606/213 |
| 2006/0229711 A1 | 10/2006 | Yan et al. | |
| 2006/0241687 A1 | 10/2006 | Glaser et al. | |
| 2007/0118176 A1 * | 5/2007 | Opolski | A61B 17/0057 606/213 |
| 2007/0167980 A1 * | 7/2007 | Figulla | A61B 17/0057 606/213 |
| 2008/0033475 A1 | 2/2008 | Meng | |
| 2008/0033534 A1 * | 2/2008 | Cook | A61F 2/848 623/1.36 |
| 2008/0147111 A1 * | 6/2008 | Johnson | A61F 2/01 606/200 |
| 2009/0012559 A1 | 1/2009 | Chanduszko | |
| 2009/0099647 A1 | 4/2009 | Glimsdale | |
| 2009/0171442 A1 * | 7/2009 | Young | A61F 2/90 623/1.15 |
| 2009/0228038 A1 * | 9/2009 | Amin | A61B 17/0057 606/213 |
| 2009/0292310 A1 * | 11/2009 | Chin | A61B 17/0057 606/215 |
| 2010/0057195 A1 | 3/2010 | Roeder | |
| 2010/0076544 A1 | 3/2010 | Hoffmann et al. | |
| 2010/0191323 A1 | 7/2010 | Cox | |
| 2010/0324538 A1 * | 12/2010 | Van Orden | A61B 17/0057 604/528 |
| 2011/0112547 A1 | 5/2011 | Uihlein | |
| 2011/0166593 A1 * | 7/2011 | Paul, Jr. | A61B 17/12022 606/200 |
| 2011/0238156 A1 | 9/2011 | Tischler et al. | |
| 2012/0071918 A1 | 3/2012 | Amin | |
| 2012/0078295 A1 | 3/2012 | Steiner | |
| 2012/0091809 A1 | 4/2012 | Müller | |
| 2012/0143242 A1 | 6/2012 | Masters | |
| 2012/0165919 A1 | 6/2012 | Cox | |
| 2012/0172927 A1 * | 7/2012 | Campbell | A61B 17/12122 606/213 |
| 2012/0283768 A1 | 11/2012 | Cox | |
| 2013/0073029 A1 * | 3/2013 | Shaw | A61F 2/848 623/1.36 |
| 2013/0138138 A1 | 5/2013 | Clark | |
| 2014/0018841 A1 | 1/2014 | Peiffer | |
| 2014/0031928 A1 | 1/2014 | Murphy | |
| 2014/0142617 A1 | 5/2014 | Larsen | |
| 2015/0265391 A1 | 9/2015 | Cully et al. | |

FOREIGN PATENT DOCUMENTS

| | | |
|---|---|---|
| JP | 2012-519572 A | 8/2012 |
| WO | WO1996032882 A1 | 10/1996 |
| WO | 01/74274 A2 | 10/2001 |
| WO | 02/56790 | 7/2002 |
| WO | 2005/084583 A2 | 9/2005 |
| WO | 2006/099470 A2 | 9/2006 |
| WO | 2007/089912 A2 | 8/2007 |
| WO | WO2008041225 A2 | 1/2008 |
| WO | 2008/083190 A2 | 7/2008 |

OTHER PUBLICATIONS

International Search Report and Written Opinion for PCT/US2013/067510, dated Feb. 13, 2014, 12 pages.
International Search Report and Written Opinion for PCT/US2013/070371, dated May 16, 2014, 29 pages.
European Search Report from 17185101.7, dated Nov. 2, 2017, 8 pages.
Annex to Form PCT/ISA/206 Communication Relating to the Results of the Partial International Search Report for PCT/US2013/067432 dated Feb. 6, 2014, corresponding to U.S. Appl. No. 14/066,382, pp. 1-3.
Durmoo et al. Biocorrosion of Stainless Steel Grade 304L (SS304L) in Sugar Cane Juice, Electrochimica Acta 54 (2008) pp. 74-79.
International Preliminary Report on Patentability received for PCT Patent Application No. PCT/US2013/067432, dated May 14, 2015, 9 pages.
International Search Report for PCT/US2013/067432 dated Jun. 12, 2014, corresponding to U.S. Appl. No. 14/066,382, pp. 7.
International Written Opinion received for PCT Patent Application No. PCT/US13/067432, dated Jun. 12, 2014, 7 pages.
Majid et al. Analysis of In Vivo Corrosion of 316L Stainless Steel Posterior Thoracolumbar Plate Systems; A Retrieval Study, J Spinal Disord Tech 2011;24:500-505.

* cited by examiner

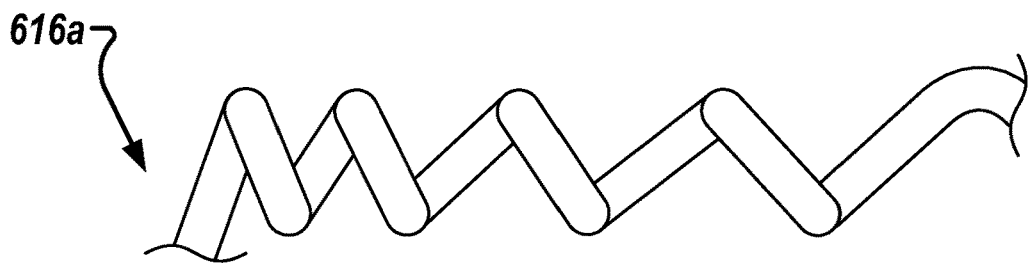
FIG. 6A
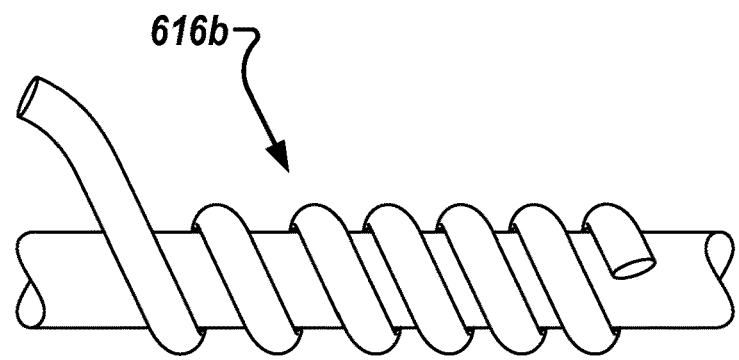
FIG. 6B
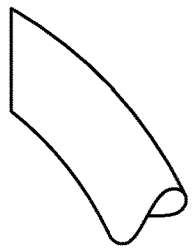 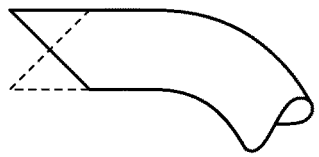 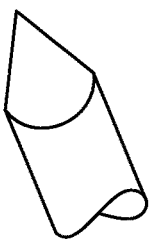
FIG. 6C  FIG. 6D  FIG. 6E
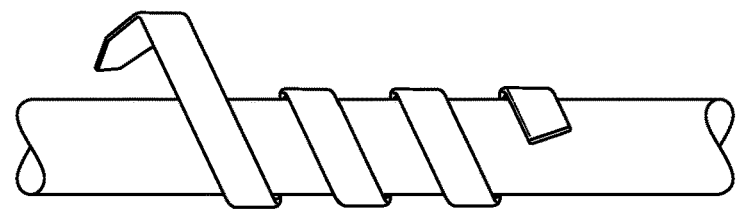
FIG. 6F
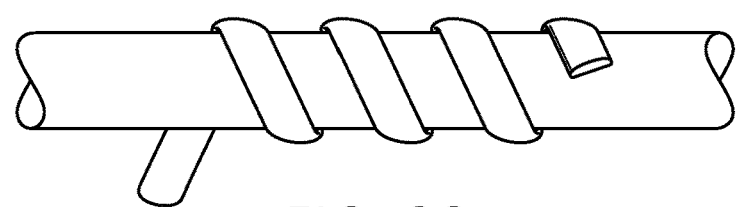
FIG. 6G

SPACE FILLING DEVICES

CLAIM OF PRIORITY

This application claims priority under 35 USC §119(e) to U.S. Provisional Application Ser. No. 61/727,458 filed on Nov. 16, 2012, and U.S. Provisional Application Ser. No. 61/798,791 filed on Mar. 15, 2013, the entire contents of which are hereby incorporated by reference.

TECHNICAL FIELD

The present disclosure relates to implantable medical devices that may be used to occlude apertures, conduits, or structures within a patient.

BACKGROUND

Cardiac features such as atrial appendages often contribute to cardiac blood flow disturbance, which is associated with a number of cardiac-related pathologies. For example, complications caused by blood flow disturbance within the left atrial appendage (LAA) and associated with atrial fibrillation can contribute to embolic stroke. The LAA is a muscular pouch extending from the anterolateral wall of the left atrium of the heart and serves as a reservoir for the left atrium. During a normal cardiac cycle, the LAA contracts with the left atrium to pump blood from the LAA, which generally prevents blood from stagnating within the LAA. However, during cardiac cycles characterized by arrhythmias (e.g., atrial fibrillation), the LAA often fails to sufficiently contract, which can allow blood to stagnate within the LAA. Stagnant blood within the LAA is susceptible to coagulating and forming a thrombus, which can dislodge from the LAA and ultimately result in an embolic stroke.

SUMMARY

In a first general aspect, a device for occluding an aperture in a body of a patient includes a plurality of elongate members. The device also includes an occlusive component that includes a plurality of first features that are each defined by a first portion of a respective elongate member of the plurality of elongate members, where the first features are located in a generally proximal region of the device. The device further includes a support component that includes a plurality of second features that are each defined by a second portion of the respective elongate member of the plurality of elongate members, where the second features are located in a generally distal region of the device. The device further includes a first termination element that is defined by proximal end portions of the plurality of elongate members, and is located near a proximal end of the device, and a second termination element that is defined by distal end portions of the plurality of elongate members, and is located near a distal end of the device. Each elongate element of the plurality of elongate elements defines one of the first features and one of the second features, and the second feature defined by a particular elongate element is generally offset in an angular direction with respect to the first feature defined by the particular elongate element when viewed from a proximal end of the device.

In various implementations, the second feature defined by the particular elongate element may be offset in a clockwise angular direction with respect to the first feature defined by the particular elongate element when viewed from the proximal end of the device. The second feature defined by the particular elongate element may be offset in a counter-clockwise angular direction with respect to the first feature defined by the particular elongate element when viewed from the proximal end of the device. The second feature defined by the particular elongate element may be generally longitudinally aligned with a first feature defined by another elongate element of the plurality of elongate elements. The first feature defined by the another elongate element may be adjacent to the first feature defined by the particular elongate element. For each elongate element of the plurality of elongate elements, the corresponding second feature defined by the elongate element may be generally offset in the angular direction with respect to the corresponding first feature defined by the elongate element when viewed from the proximal end of the device. A winding direction may be reversed for at least one elongate member of the plurality of elongate members between the corresponding first and second features defined by the at least one elongate member. The winding direction may reverse from clockwise to counter-clockwise, or from counter-clockwise to clockwise. The first and second termination elements may be eyelets. The device may also include a membranous covering that covers at least a portion of the device. The membranous covering may cover the occlusive component and the support component. The membranous covering may cover the first termination element and the second termination element. Each elongate member of the plurality of elongate members may be a wire, such as a Nitinol wire. The device may be formed by cutting a metal tube. Each elongate member of the plurality of elongate members may be a portion of a tube. The device may further include one or more anchor elements. The one or more anchor elements may include a frame attachment portion and an anchor portion, where the frame attachment portion includes a first portion of a fixation elongate element wrapped multiple times around an elongate member of the plurality of elongate members, and the anchor portion includes an anchor feature for engaging body tissue at a second portion of the fixation elongate element. The one or more anchor elements may include an anchor portion formed by a portion of an elongate element of the plurality of elongate elements.

In a second general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a first termination element that is defined by proximal end portions of the plurality of elongate members, and is located near a proximal end of the device, and a second termination element that is defined by distal end portions of the plurality of elongate members, and is located near a distal end of the device. Between a corresponding first feature and a corresponding second feature each defined by a particular elongate element of the plurality of elongate elements, a winding direction of the particular elongate element is reversed.

In a third general aspect a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a termination element that is defined by proximal end portions of the plurality of elongate members and by distal end portions of the plurality of elongate members.

In a fourth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a first termination element that is defined by proximal end portions of the plurality of elongate members, and is located near a proximal end of the device. The device further includes a second termination element that is defined by distal end portions of the plurality of elongate members, and is located near a distal end of the device. Each elongate element of the plurality of elongate elements defines one of the first features and one of the second features, and the second feature defined by a particular elongate element is generally aligned in a longitudinal dimension of the device with the first feature defined by the particular elongate element.

In a fifth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a first termination element that is defined by proximal end portions of the plurality of elongate members, and is located near a proximal end of the device. The device further includes a second termination element that is defined by distal end portions of the plurality of elongate members, and is located near a distal end of the device within a space defined by the plurality of elongate members. Ends of the distal end portions are located nearer a proximal-facing end of the second termination element than to a distal-facing end of the second termination element.

In a sixth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a termination element that is defined by proximal end portions of the plurality of elongate members and by distal end portions of the plurality of elongate members, where the termination element are located near a proximal end of the device. The device further includes a hub component located near a distal end of the device, where the hub component includes a generally donut-shaped member through which each elongate member of the plurality of elongate members passes.

In a seventh general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a first termination element that is defined by proximal end portions of the plurality of elongate members, and is located near a proximal end of the device within a space defined by the plurality of elongate members. Ends of the proximal end portions are located nearer a distal-facing end of the first termination element than to a proximal-facing end of the first termination element. The device further includes a second termination element that is defined by distal end portions of the plurality of elongate members, and is located near a distal end of the device within a space defined by the plurality of elongate members. Ends of the distal end portions are located nearer a proximal-facing end of the second termination element than to a distal-facing end of the second termination element.

In an eighth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a first termination element that is defined by proximal end portions of the plurality of elongate members, and is located near a proximal end of the device, and a second termination element that is defined by distal end portions of the plurality of elongate members, and is located near a distal end of the device. The device further includes one or more anchor elements that include a frame attachment portion and an anchor portion, where the frame attachment portion includes a first portion of a fixation elongate element wrapped multiple times around an elongate member of the plurality of elongate members, and where the anchor portion includes an anchor feature for engaging body tissue at a second portion of the fixation elongate element.

In a ninth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a first termination element that is defined by proximal end portions of the plurality of elongate members, and is located near a proximal end of the device. The device further includes a second termination element that is defined by distal end portions of the plurality of elongate members, and is located near a distal end of the device. Adjacent elongate elements of the plurality of elongate elements are wound in opposite directions.

In a tenth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a termination element that is defined by proximal end portions of the plurality of elongate members, where the termination element is located near a proximal end of the device. The device further includes a hub component located near a distal end of the device, where the hub component includes a body portion that defines a plurality of apertures through a side wall of the body portion, and where the apertures are disposed at an angle so that the slots are not orthogonal to the side wall. Each elongate member of the plurality of elongate members passes through an aperture of the plurality of apertures and wraps around at least a portion of the side wall of the hub component.

In an eleventh general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a termination element that is defined by proximal end portions of the plurality of elongate members, where the termination element is located near a proximal end of the device. The device further includes a hub component located near a distal end of the device, where the hub component includes a base surface, a retaining surface, and a region defined between the base surface and the retaining surface, and where an end portion of each elongate member of the plurality of elongate members is located within the region defined between the base surface and the retaining surface.

In a twelfth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a termination element that is defined by proximal end portions of the plurality of elongate members and by distal end portions of the plurality of elongate members, where the termination element is located near a proximal end of the device. The device further includes a hub component located near a distal end of the device, where the hub component includes a generally ring shaped body that defines a plurality of apertures longitudinally through a side wall of the generally ring-shaped body. Each elongate member of the plurality of elongate members passes through two of the apertures in the side wall of the generally ring-shaped body.

In a thirteenth general aspect, a device for occluding an aperture in a body of a patient includes a plurality of elongate members, and an occlusive component that includes a plurality of first features that are each defined by a first portion of a respective elongate member of the plurality of elongate members, where the first features are located in a generally proximal region of the device. The device also includes a support component that includes a plurality of second features that are each defined by a second portion of the respective elongate member of the plurality of elongate members, where the second features are located in a generally distal region of the device. The device further includes a termination element that is defined by proximal end portions of the plurality of elongate members and by distal end portions of the plurality of elongate members, where the termination element is located near a proximal end of the device. The device further includes a hub component located near a distal end of the device, where the hub component includes a generally ring shaped body and defines a plurality of apertures longitudinally through a side wall of the generally ring-shaped body. Each elongate member of the plurality of elongate members includes a ball end that is sized larger than the apertures, and each elongate member of the plurality of elongate members passes through an apertures in the side wall of the generally ring-shaped body.

Methods are disclosed for occluding an aperture in a patient. The methods include providing any of the devices disclosed herein, advancing a delivery apparatus, to which the device is attached, to a location of aperture, and deploying the device at the location.

The details of one or more embodiments are set forth in the accompanying drawings and the description below. Other features, objects, and advantages will be apparent from the description and drawings, and from the claims.

BRIEF DESCRIPTION OF THE DRAWINGS

FIGS. 6A and 6B are side views of example anchor attachment portions of example fixation anchors.

FIGS. 6C-6E are views or example grind geometries for anchor fixation members.

FIGS. 6F and 6G are views of example anchor frame wire profiles.

Like reference symbols in the various drawings indicate like elements.

DETAILED DESCRIPTION

Figure 1A:
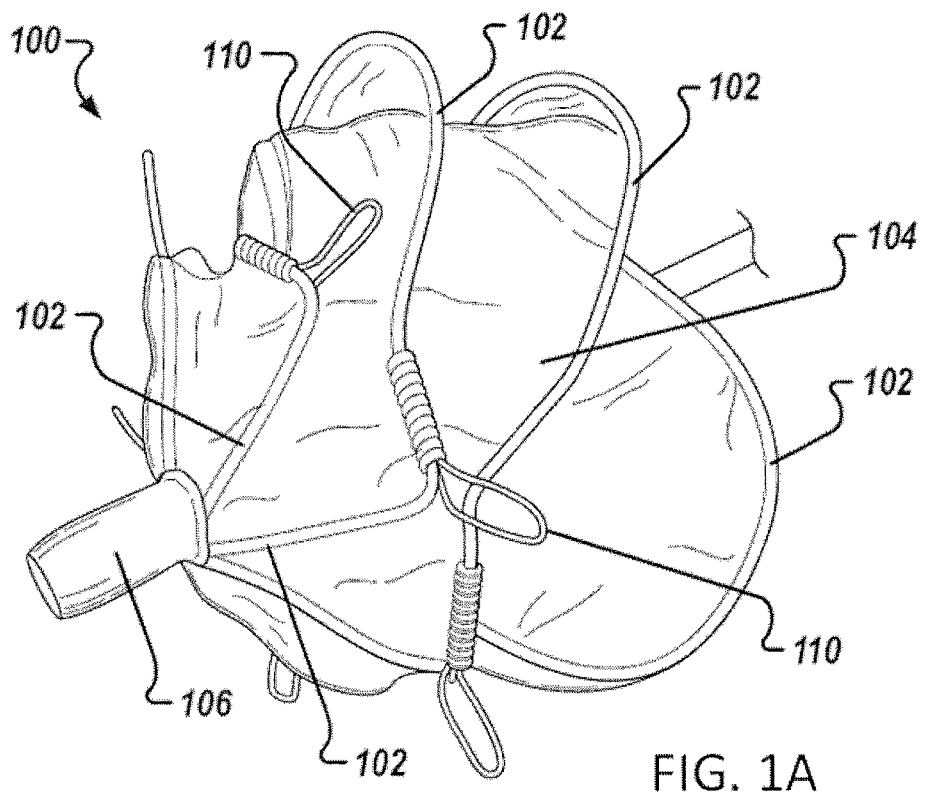
FIG. 1A is a perspective view of an example occlusion device that can be used to occlude a hole, defect, aperture, or appendage within a body of a patient.

This document describes devices, systems and methods that are useful, for example, for occluding spaces, holes, defects, apertures, appendages, vessels or conduits within a body of a patient. Several implantable medical devices are described herein, and in general any of the features described with respect to a particular device may also be used with any of the other devices described herein. In some examples, one or more features described with respect to a particular device may replace or be substituted for one or more features of another device. In some examples, one or more features described with respect to a particular device may be added to or included with another device. Also, various combinations or sub-combinations of any of the features described herein may generally be used with any of the devices described herein.

In general, any of the implantable medical devices described herein can be delivered to, and deployed at, an in vivo deployment site within a body of a patient using various minimally invasive transcatheter deployment techniques. For example, any of the implantable medical devices described herein may be releasably attached to a delivery catheter, and the device and delivery catheter may be loaded into a delivery sheath. The delivery sheath may be introduced to the vasculature of the patient and advanced through the vasculature, until a distal end of the delivery sheath is located at or near the target in vivo deployment site. The implantable medical device may be deployed at the deployment site, for example by retracting the delivery sheath and/or advancing the delivery catheter and the implantable medical device, and detaching the implantable medical device from the delivery catheter. In some implementations, a first portion of the device is released from the delivery sheath while a second portion of the device remains constrained by the delivery sheath, a positioning of the first portion of the device is verified, and then the second portion of the device is released from the delivery sheath. The delivery catheter and delivery sheath can then be withdrawn or retracted from the body of the patient.

Any of the implantable medical devices discussed herein can be used to occlude a left atrial appendage (LAA) of a human heart. The implantable medical devices can be delivered in an endovascular manner through or over a catheter system to a delivery site, such as the LAA or other appropriate delivery site, and deployed at the site. The implantable medical devices can be deployed within the LAA or across the ostium of the LAA to isolate the LAA from the main chamber of the left atrium (left atrial chamber), for example. This may prevent thrombus formation within the LAA and/or thrombus exit from the LAA. In this manner, a risk of stroke may be reduced or minimized.

In some implementations, the devices described herein can assume two or more configurations. For example, while the device is being delivered to the deployment site, the device may assume a collapsed or delivery configuration. Following deployment of the device, the device may assume an expanded or deployed configuration. While the device is being deployed, for example, the device may assume one or more partially expanded or partially deployed configurations.

Figure 1B:
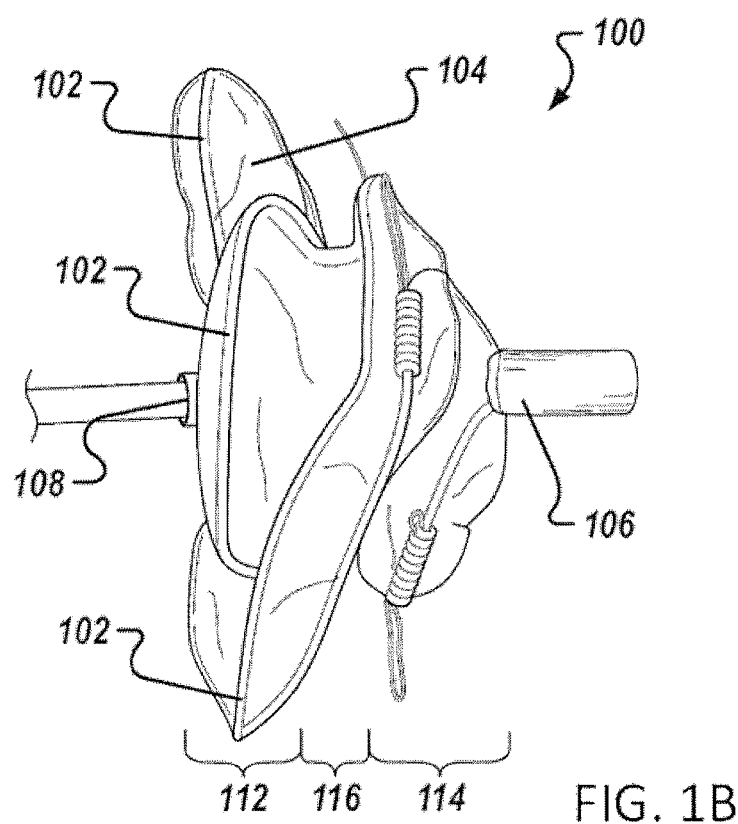
FIG. 1B is a side view of the example occlusion device of FIG. 1A.

FIGS. 1A and 1B are, respectively, perspective and side views of an example occlusion device 100 that can be used to occlude a hole, defect, aperture, appendage, vessel or conduit within a body of a patient. The occlusion device 100 includes a frame comprised of elongate members 102, and includes a membranous covering 104 that covers at least a portion of the frame. As used herein, "frame" may refer to an entire frame of a device, or may alternatively refer to a localized portion of a device that includes at least one elongate member.

Elongate members 102 are wires in some implementations. For example, elongate members 102 may be spring wires, shape memory alloy wires, or super-elastic alloy wires. Elongate members 102 can be made of nitinol (NiTi), L605 steel, stainless steel, or any other appropriate biocompatible material. Additionally, specialized forms of metals can be used. For example, drawn-filled tubes that use platinum, tantalum, or other appropriate noble metals for the wire core may be used for enhanced radio-opacity. An example is a platinum drawn filled nitinol wire that is available from Fort Wayne Metals (Fort Wayne, Ind.). In some embodiments, bioresorbable or bioabsorbable materials may be used, for example a bioresorbable or bioabsorbable polymer. The super-elastic properties of NiTi make it a particularly good candidate material for the elongate members 102 (e.g., NiTi wires can be heat-set into a desired shape), according to some implementations. NiTi can be heat-set so that an elongate member 102 can self-expand into a desired shape when the elongate member 102 is placed in a less restrictive environment, such as when it is deployed from the delivery sheath to a body cavity. The elongate members 102 can provide structure and shape for the device 100. In general, the devices described herein include elongate members 102 that are shaped as desired to suit the purpose of the device. The elongate members 102 may generally be conformable, fatigue resistant, and elastic such that the elongate members 102 have a stored length. The elongate members 102 may have a spring nature that allows them to collapse and elongate to a pre-formed shape (e.g., the frame of a device may have a pre-formed shape).

In some embodiments, the diameter or thickness of the elongate members 102 may be about 0.020 mm to 0.040 mm, but in other embodiments elongate members having smaller or larger diameters may be used. In some embodiments, the elongate members 102 have a diameter of about 0.022 mm. In some embodiments, each of the elongate members 102 has the same diameter. In some embodiments, one or more portions of the elongate members 102 may be diametrically tapered. Tapering of elongate members may permit varying a stiffness of portions of the device. For example, device stiffness may be varied along a longitudinal axis of the device, in some implementations. The elongate members may have a round cross-sectional shape or may have a cross-sectional shape that is not round, such as a rectangle or other polygon. Examples of other cross-sectional shapes that the elongate members 102 may have include a square, oval, rectangle, triangle, D-shape, trapezoid, or irregular cross-sectional shape formed by a braided or stranded construct. In some embodiments, an occlusion device may include flat elongate members 102. In some examples, the elongate members 102 may be formed using a centerless grind technique, such that the diameter of the elongate members 102 varies along the length of the elongate members 102.

The membranous covering 104 may be a porous, elastic member that can stretch and collapse to accommodate extension and collapse, respectively, of the elongate members 102. Pores of the membranous covering 104 may be sized to substantially, or in some examples completely, prevent passage of blood, other bodily fluids, and emboli. In some implementations, the membranous covering 104 prevents or substantially prevents passage of blood, other bodily fluids, emboli, or other bodily materials through the membranous covering 104. The membranous covering 104 can have a microporous structure that provides a tissue ingrowth scaffold for durable occlusion and supplemental anchoring strength of the occlusion device 100. Some embodiments of the membranous covering 104 comprise a fluoropolymer, such as an expanded polytetrafluoroethylene (ePTFE) polymer.

In some embodiments, the membranous covering 104 is configured such that the inhibition of fluid passage through the membranous covering 104 is immediate and does not rely on a thrombotic process. In some embodiments, the membranous covering 104 can be modified by one or more chemical or physical processes that enhance certain physical properties of the membranous covering 104. For example, a hydrophilic coating may be applied to the membranous covering 104 to improve the wettability and echo translucency of the membranous covering 104. In some embodiments, the membranous covering 104 may be modified with chemical moieties that promote one or more of endothelial cell attachment, endothelial cell migration, endothelial cell proliferation, and resistance to thrombosis. In some embodiments, the membranous covering 104 may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

In some embodiments, the membranous covering 104 may be formed of a fluoropolymer (e.g., expanded PTFE (ePTFE) or PTFE). In some embodiments, the membranous covering 104 may be formed of a polyester, a silicone, a urethane, or another biocompatible polymer, or combinations thereof. In some embodiments, bioresorbable or bioabsorbable materials may be used, for example a bioresorbable or bioabsorbable polymer. In some embodiments, the membranous covering 104 may be formed of a copolymer. In some examples, a first portion of the membranous covering 104 may be formed of a first material and a second portion of the membranous covering 104 may be formed of a second material. For example, the portion of the membranous covering 104 that covers an occlusion member of the device may be formed of a first material, and a portion of the membranous covering 104 that covers a support member of the device may be formed of a second material.

The example occlusion device 100 includes six elongate members 102, but in other examples, and generally for any of the devices discussed herein, more or fewer elongate members 102 may be used (e.g., two, three, four, five, seven, eight, nine, ten, eleven, twelve, or more). As described above, the device 100 may assume a collapsed configuration, in which the elongate members 102 of the device 100 may be elongated so that the device assumes a low crossing profile for positioning within a delivery sheath. In some examples, the elongate members 102 are caused to collapse or elongate as the device is pulled into the delivery sheath. The sheath may provide a constraining environment and may maintain the device in the delivery configuration while the device is located within the sheath. The device 100 may be configured to self-expand as a result of a bias or shape-memory property of the elongate members, where the device may self-expand upon liberation from the constraining environment, as by exiting the delivery sheath. The example occlusion device 100 is shown in an expanded configuration in FIGS. 1A and 1B, and this configuration is a result of the self-expanding nature of the elongate members 102.

The frame also includes, in this example, a distal eyelet 106 and a proximal eyelet 108, each of which is covered by the membranous covering 104 in this example. In other examples, the distal eyelet 106, proximal eyelet 108, or both, is/are completely covered by the membranous covering 104, or is/are completely uncovered by the membranous covering 104. In some examples, one or both of the eyelets is partially covered by the membranous covering 104. The distal eyelet 106 and the proximal eyelet 108 can be made from the coiled end portions of the one or more elongate members 102. In various implementations, one or more components of a delivery system may attach to the occlusion device 100 at the distal eyelet 106, at the proximal eyelet 108, or at both the distal eyelet 106 and the proximal eyelet 108. In some examples, one or more of the distal eyelet 106 and the proximal eyelet 108 may be considered an attachment feature for the device 100. Such attachment features can provide locations for releasable couplings with a deployment system. In some implementations, one or more attachment elements or components are located within a space defined by the distal eyelet 106 or within a space defined by the proximal eyelet 108, and one or more delivery system components can be releasably coupled to the one or more attachment elements. In various examples, attachment can be by, for example, threaded screw-type connections, spring-loaded connections, snap-fit connections, and others.

Occlusion device 100 also includes fixation anchors 110, in the depicted example. Fixation anchors 110 can contact surrounding tissue at a target deployment site so as to secure the position of the device 100, or certain portions of the device, at the target deployment site. Fixation anchors 110 can be made from a variety of suitable materials. For example, the fixation anchors 110 can be made of NiTi, L605 steel, MP35N steel, stainless steel, a polymeric material, Pyhnox, Elgiloy, or any other appropriate biocompatible material. In some embodiments, the fixation anchors 110 can be made from a non-permanent biodegradable or bioabsorbable material. The super-elastic properties of NiTi make it a particularly good candidate material for such fixation anchors, according to some implementations. NiTi can be heat-set so that a fixation anchor can self-expand into a desired shape when the fixation anchor is placed in a less restrictive environment, such as when it is deployed from the delivery sheath to a body cavity. In some embodiments, it is desirable for a fixation anchor to be biased to have a particular shape to enhance the anchoring properties of the fixation anchor. In some embodiments, the device 100 does not include fixation anchors 110.

The devices described herein may sometimes be repositioned after deployment to an initial location, or may be retrieved from a current deployment location. As part of repositioning the device, the device may be pulled back into the delivery sheath, for example. The anchors described herein (both for anchors designed to pierce tissue on deployment, and for anchors designed to not pierce or only minimally pierce tissue on deployment) may be adapted to minimize tissue damage on repositioning or retrieval of the device. For example, the anchors may relinquish the tissue on retrieval without substantial additional trauma to the tissue. This feature may reduce or minimize trauma, pericardial effusion, major perforations, or erosions, for example.

Device 100 includes a proximal region 112, a distal region 114, and a transition region 116 between the proximal region 112 and the distal region 114. Each of the proximal region 112, distal region 114, and transition region 116 are defined by the shape of the elongate members 102 in the respective areas. In general, the shape or topology of each of the regions may be selected as desired to suit the purpose of the device, and the elongate members 102 of the device 100 can be wound and heat-set in constructing the device so that, in a deployed configuration, the elongate members 102 assume the desired shape or topology.

In this example, the elongate members 102 are shaped to form features in each of the proximal region 112 and the distal region 114. With reference first to the proximal region 112, the elongate members 102 are shaped to generally collectively form an occlusion disc or occlusion bulb that can be used to substantially seal the space, hole, defect, aperture, appendage, vessel or conduit at the deployment site within the body of a patient. The elongate members 102, in the distal region 114, are shaped to generally form a second disc or bulb that can provide support for the device and can be used to position or anchor the device at a particular location at the delivery site. Within the transition region 116, which may alternatively be referred to as an inflection region or a waist region, the elongate members 102 transition from the feature formed in the proximal region 112 to the feature formed in the distal region 114. In some examples, the elongate members 102 may be shaped to form one or more occlusion features to appropriately occlude or partially occlude an aperture. In various implementations, such occlusion features may be included in the proximal region 112, in the distal region 114, in the transition region 116, or in combinations of the foregoing.

The distal region 114 and the distal eyelet 106 are referred to as "distal" because, after deployment, their position is generally distal of other portions of the device with respect to the delivery system. By contrast, the proximal region 112 and the proximal eyelet 108 are referred to as "proximal" because their deployed position is generally proximal to the delivery system as compared to other portions of the device. In some examples, the distal eyelet 106 and distal region 114 are deployed first from the delivery sheath, the transition region 116 is deployed next, and finally the proximal region 112 and the proximal eyelet 108 are deployed from the delivery sheath. With respect to a LAA, following deployment of the device, the distal eyelet 106 may be oriented to face the interior of the LAA, while a proximal-facing face of the proximal region 112 and the proximal eyelet 108 may be oriented to face the left atrial chamber of the heart.

Figure 2:
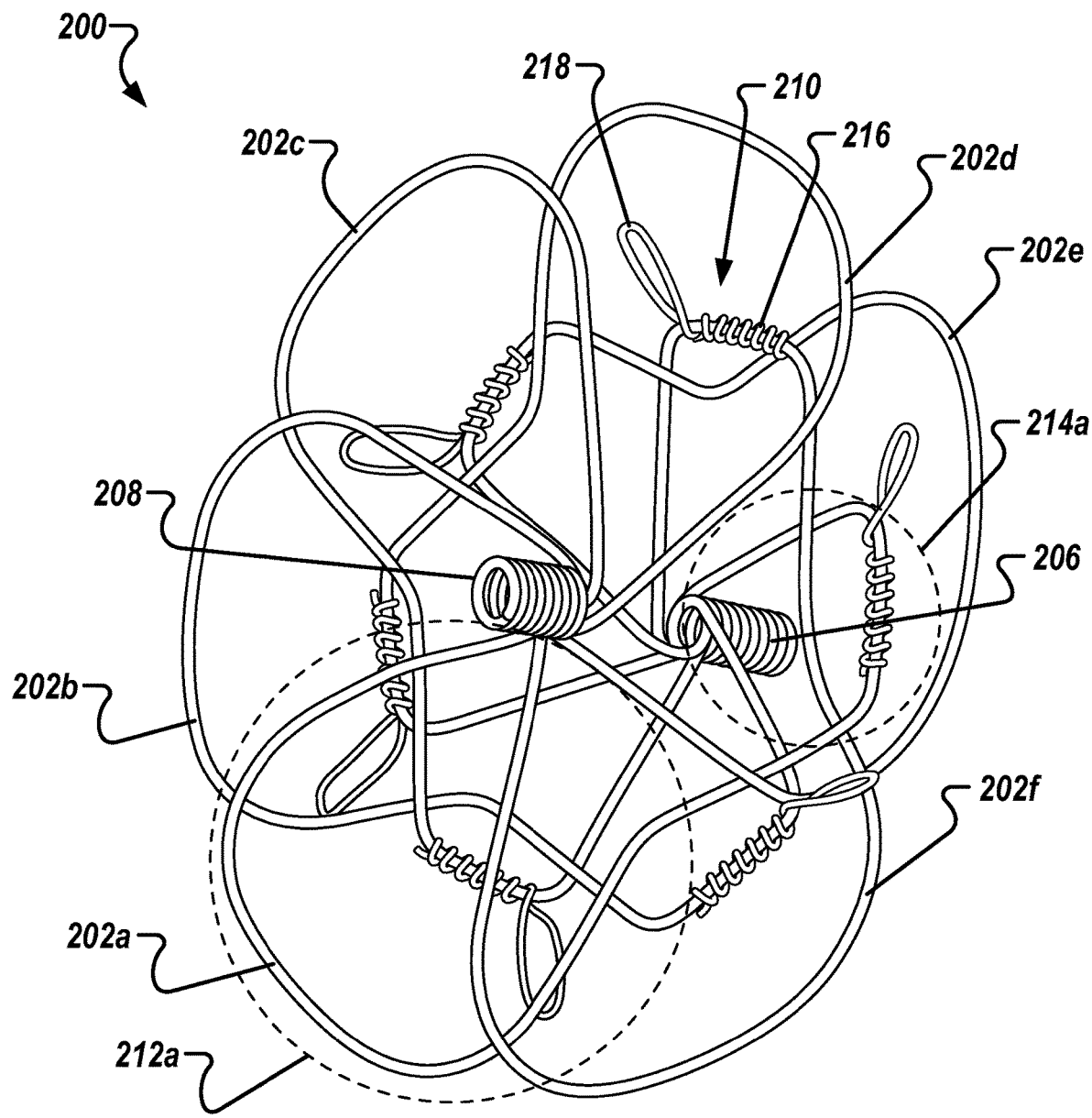
FIG. 2 is a perspective view of an example occlusion device frame that can be used to occlude a hole, defect, aperture, or appendage within a body of a patient.

FIG. 2 is a perspective view of an example frame 200 of an example occlusion device. For example, the frame 200 may correspond to the frame of the occlusion device 100 of FIGS. 1A and 1B, but with the membranous covering 104 removed. Elongate members 202 correspond to the elongate members 102 of FIGS. 1A and 1B; distal eyelet 206 corresponds to distal eyelet 106 of FIGS. 1A and 1B; proximal eyelet 208 corresponds to proximal eyelet 108 of FIGS. 1A and 1B; and fixation anchors 210 correspond to fixation anchors 110 of FIGS. 1A and 1B.

In general, the frames for any of the devices described herein may be constructed from one or more elongate members. Devices may be constructed using a modular tool, in some examples, or by using a jig apparatus in other examples. In some implementations, device frames may be wound generally as follows: a first eyelet (e.g., a distal eyelet) may be wound around a mandrel. In some examples, the eyelet may be wound on a mandrel having a round cross-section, so that the eyelet also has a round cross section. In other examples, the eyelet may be wound on a mandrel having a non-round cross-section, such as an ovalized cross section, so that the eyelet has an ovalized shape. Such an eyelet that does not have a round cross-section may be referred to as a "keyed" eyelet, and when two-eyelet devices include keyed eyelets, eyelet alignment may be improved, for example. Next, one or more features of a first region (e.g., the distal region) may be wound; one or more features of a second region (e.g. the proximal region) may be wound; and a second eyelet (e.g., the proximal eyelet) may be wound around the mandrel. In some examples, one or more features of a third region (e.g., the transitional region) may involve an additional winding step, and in the example above the additional winding step could occur after the step of winding the feature of the first region. In other examples, the winding order described above may be reversed, so that the proximal eyelet is wound first and the distal eyelet is wound last. The elongate members of the frame may be completely or partially coated with fluorinated ethylene propylene (FEP) or another appropriate adhesive material, and baked to heat set the frame.

The elongate members may be wound, for example, using a winding jig or a modular tool and by guiding each elongate member along a winding path defined by one or more pins, bars, blocks, channels, or feature-defining jig components to create the features of the device as desired. When using a jig apparatus, for example, the elongate members may follow a predetermined path as defined by the jig apparatus or determined by features of the jig apparatus. For example, for a given device with a given number of elongate members, a first eyelet may be created by winding first ends of the elongate members in a coiled fashion around a pin or mandrel. The elongate members can then be fanned out (e.g., if using a modular tool) from the first eyelet to define features of the first region, as by winding the elongate members around one or more feature-defining components, or routed along a predetermined path of a jig apparatus, for example. The elongate members can then be wound around one or more feature-defining jig components (or tool features for a modular tool process) to define features of the second region, and then the second ends of the elongate members can be wound again around the pin or mandrel in a coiled fashion to define the second eyelet. A heat set process may be applied to the formed device, as appropriate. As described above, mandrels having round, ovalized, or other cross-sectional shape can be used. In some implementations, the proximal and distal eyelets are aligned along a longitudinal axis of the device.

In some embodiments, the frame 200 includes six elongate members 202, labeled 202a, 202b, 202c, 202d, 202e, and 202f. A first end portion of each of the six elongate members 202a-202f forms the proximal eyelet 208, and a second (opposite) end portion of each of the elongate members 202a-202f forms the distal eyelet 206. Between the eyelets, in this example, are the features of the proximal region and the distal region (corresponding to proximal region 112 and distal region 114 of FIG. 1B, for example). With reference to elongate member 202a, the elongate member 202a extends from the proximal eyelet 208 and forms a proximal feature 212a. The proximal feature 212a may generally be referred to as a "petal" of the device, and may generally be located in a proximal region of the device (e.g., corresponding to region 112 of the device of FIG. 1B). After passing through a transition region (e.g., corresponding to region 116 of the device of FIG. 1B) of the device, the elongate member 202a forms a distal feature 214a. The distal feature 214a may generally be located in a distal region of the device (e.g., corresponding to region 114 of the device of FIG. 1B).

Similarly, each of the elongate members 202b-202f extends from the proximal eyelet 208 and forms a respective proximal feature in the proximal region of the device, passes through the transition region of the device, and forms a respective distal feature in the distal region of the device. The six proximal features or petals may be generally spaced equidistantly (or in some examples not equidistantly) around the proximal eyelet 208, and in aggregate the six proximal features may form an occlusion feature of the frame 200 (e.g., when the frame or a portion of the frame is covered by a membranous covering). When the proximal features of the frame are covered by a membranous covering, for example, the occlusion feature may be used to occlude an LAA, or other space, hole, defect, aperture, appendage, vessel or conduit within a body of a patient. Similarly, the six distal features may be generally equidistantly spaced around the distal eyelet 206, and in aggregate the six distal features may form a support feature of the frame 200.

The fixation anchors 210 generally include a frame attachment portion 216 that is wrapped or coiled around a corresponding elongate member 202 to secure the fixation anchor 210 to the frame of the device, and an anchor portion 218 that can anchor, secure, or fix the device to body tissue at the deployment site so that migration of the device within the body may be reduced or minimized. In the depicted example, the fixation anchors 210 include a frame anchor wire. A first portion of the frame anchor wire is wrapped or coiled around a corresponding elongate member 202, as part of the frame attachment portion 216. A second portion of the frame anchor wire forms the loop or boot of the anchor portion 218. A third portion of the frame anchor wire is located between the coiled portion of the frame anchor wire and the elongate member 202 as part of the frame attachment portion 216, so that the coiled portion of the wire loops around both the elongate member and this third portion of the frame anchor wire. In some implementations, because the coiled portion of the frame anchor wire loops around both the elongate member 202 and the third portion of the frame anchor wire, the fixation anchor 210 may have better engagement with the frame, for example, and may be less likely to slip or rotate around the elongate member 202. For example, the coiled portion in this case is not concentric with only the elongate member 202, but is also concentric with the third portion of the frame anchor wire. In some examples, the frame attachment portion 216 and/or the corresponding portion of the elongate member 202 is coated with FEP or another appropriate adhesive material to secure the frame attachment portion 216 of the fixation anchor 210 to the frame 200.

The fixation anchors discussed herein can be made from a variety of suitable materials. For example, the fixation anchors can be made of NiTi, L605 steel, stainless steel, a polymeric material, or any other appropriate biocompatible material. In some embodiments, the fixation anchors can be made from a non-permanent biodegradable or bioabsorbable material. The super-elastic properties of NiTi make it a particularly good candidate material for such fixation anchors, according to some implementations. NiTi can be heat-set so that a fixation anchor can self-expand into a desired shape when the fixation anchor is placed in a less restrictive environment, such as when it is deployed from the delivery sheath to a body cavity. In some embodiments, it is desirable for a fixation anchor to be biased to have a particular shape to enhance the anchoring properties of the fixation anchor.

In some implementations, the fixation anchors discussed herein are formed from one, two, or more elongate members (e.g., wires) that are separate or distinct from the elongate members that define the frame of the device. For a given fixation anchor wire of a fixation anchor 210, a first portion of the fixation anchor wire may be wound or coiled around an elongate member 202. A second portion of the fixation anchor wire may be used to form the anchor portion 218, which comprises a generally oval-shaped loop in the depicted example of FIG. 2, and a third portion of the fixation anchor wire may be wound around the elongate member 202. In the example of FIG. 2, the third portion of the fixation anchor wire is wound around generally the same area of elongate member 202 as is the first portion of the fixation anchor, and together the first and third portions of the fixation anchor wire comprise the frame attachment portion 216. Loop shapes other than an oval may be used for anchor portions 218, including an ellipse, circle, triangle, square, rectangle, diamond, or other polygon.

In general, fixation elements discussed herein (including micro-coil anchors, discussed in more detail below) may comprise an elongate element or fixation anchor wire that is separate from the elongate elements that define the frame of the device. In some embodiments, each of the fixation anchor wires has the same diameter. In some embodiments, one or more portions of the fixation anchor wires may be diametrically tapered. The fixation anchor wires may have a round cross-sectional shape or may have a cross-sectional shape that is not round, such as a rectangle or other polygon. Examples of other cross-sectional shapes that the fixation anchor wires may have include a square, oval, rectangle, triangle, D-shape, trapezoid, or irregular cross-sectional shape formed by a braided construct. In some embodiments, an occlusion device may include flat fixation anchor wires. In some examples, the fixation anchor wires may be formed using a centerless grind technique, such that the diameter of the fixation anchor wires varies along the length of the fixation anchor wires.

In the depicted example, the fixation anchors 210 are included on portions of the elongate members 202 in the distal region 114 (see FIG. 1B) of the frame. In some examples, fixation anchors 210 may be included on portions of the elongate members 202 in the proximal region 112 of the frame, and may not be included in the distal region 114. In some examples, fixation anchors 210 may be included on both the distal region 114 and on the proximal region 112. In some examples, fixation anchors may be included on the transition region 116. FIGS. 8A-8E show some examples of possible fixation anchor locations on example occlusion devices.

In the depicted example, one fixation anchor 210 is included on each of the elongate members 202 in the distal region of the frame. Stated another way, each of the features (six in this example) of the distal region 114 of the frame includes a fixation anchor 210. In some implementation, one or more of the elongate elements 202 does not include a fixation anchor 210. For example, in some implementations, a first subset of the elongate members includes one or more fixation anchors 210, and a second subset of the elongate members does not include a fixation anchor 210. In various examples, if the elongate members 202 are consecutively numbered from 1 to n (1 to 6 in this example since frame 200 includes six wires), the odd-numbered elongate members may include a fixation anchor while the even-numbered elongate members may not include a fixation anchor, or vice versa. Stated another way, every-other elongate element may include a fixation anchor 210 (e.g., elongate elements 202a, 202c, and 202e; or elements 202b, 202d, 202f). In other examples, every third elongate element may include a fixation anchor (e.g., elements 202a and 202d; or elements 202b and 202e; or elements 202c and 202f).

Fixation anchors that comprise a frame attachment portion that includes at least a portion of the fixation anchor member wrapped or coiled around a frame-defining elongate member 202, including anchors 210 in FIG. 2, may generally be referred to as "micro-coil" anchors. Micro-coil fixation anchors can have many different shapes and styles, as will be further described below with reference to FIGS. 3A-3C, 4A-4D, 5A-5F, 6A, 6B, 7A-7E, and 8A-8E. In general, micro-coil fixation anchors may include either an active anchor portion that is adapted to penetrate body tissue at the deployment site, or may include a passive anchor portion that is adapted to non-traumatically contact body tissue at the deployment site, generally without piercing the body tissue. Anchor portion 218 of fixation anchor 210 is such a passive anchor type. Passive anchor portions are generally intended to engage tissue with minimal penetration of the tissue.

Figure 3A:
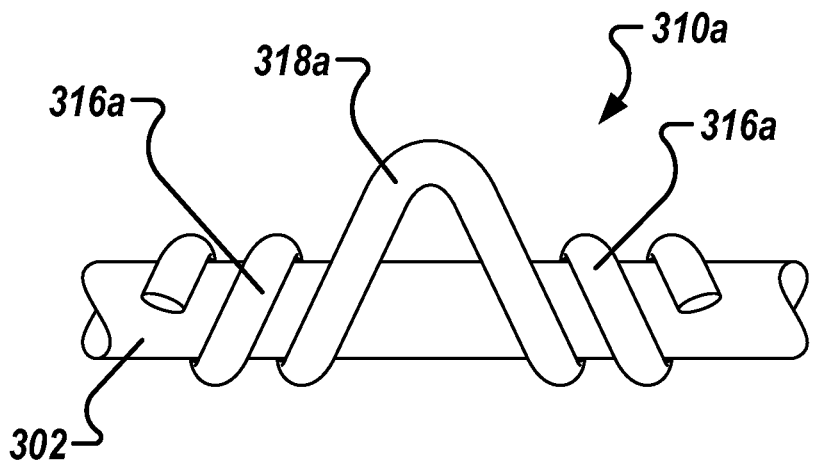
FIGS. 3A-3C, 4A-4D, and 5A-5D are side views of example fixation anchors.
Figure 3B:
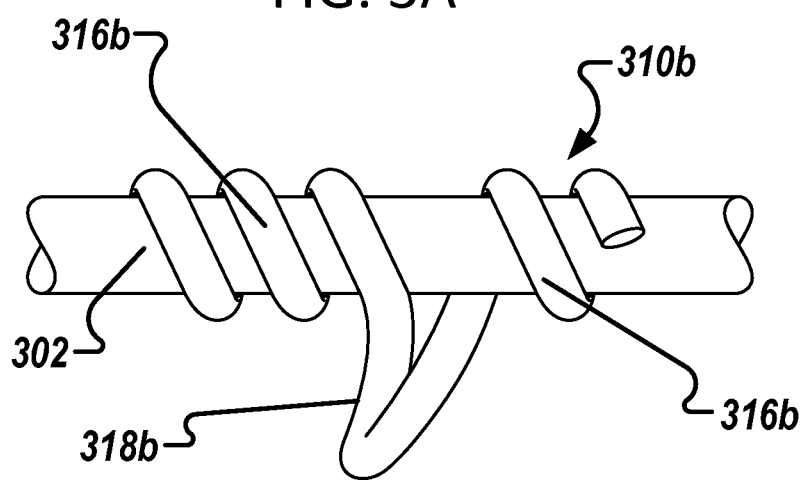
Figure 3C:
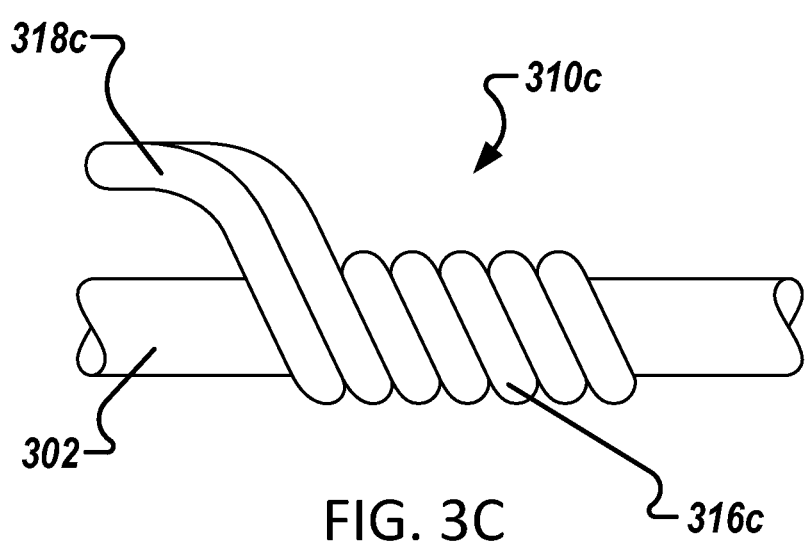

FIGS. 3A-3C are side views of example fixation anchors 310a, 310b, and 310c, respectively. Each of the anchors 310a, 310b, and 310c may be considered micro-coil anchors, and each includes a passive anchor portion 318. Each of the anchors 310a, 310b, and 310c comprises an elongate member, such as a wire, and includes an anchor portion 318 adapted for atraumatic contact with body tissue at a deployment site. Each of the frame attachment portions 316 of the fixation anchor wire are wrapped or coiled around a corresponding frame-defining elongate member 302 of a medical device. In some implementations, frame attachment portion 316 and/or the corresponding portion of the elongate member 302 can be coated with FEP or another appropriate adhesive material to secure the frame attachment portion 316 of the fixation anchor 310 to the elongate member 302 of the frame, and in some implementations the wire is coiled around the elongate member 302 without addition of FEP or other adhesive. In some examples, the anchors can be welded or soldered to the elongate members.

With reference to FIG. 3A, anchor portion 318a may comprise a protruding loop. In this example, each side or leg of the loop is located on the same side of elongate member 302. In some examples, the loop may be located on the radially outward-facing side of the elongate member 302, and in some examples the loop may be located on the radially inward-facing side of the elongate member 302. The anchor 310a includes first and second frame attachment portions 316a, one on each side of the anchor portion 318a. Anchor portion 318a may comprise a protruding loop.

Fixation anchor 310b of FIG. 3B also includes an anchor portion 318b that includes a protruding loop, but in this example the sides or legs of the loop are located on the opposite side of elongate member 302. The loop includes a backward-angled curve or bend, which may facilitate passive engagement with tissue at a deployment site. The anchor 310b includes first and second frame attachment portions 316b, one on each side of the anchor portion 318b.

Fixation anchor 310c of FIG. 3c also includes an anchor portion 318c that includes a protruding loop, but in this example the anchor portion 318c is at the end of the anchor rather than in the middle. That is, the frame attachment portion 316c is located to the right of (e.g., distal of) the anchor portion 318C in this example. In other examples, the frame attachment portion 316c may be located proximal of the anchor portion 318C. In some examples, the loop of anchor portion 318c is axially facing, and may engage axially and prevent migration in the axial direction. While each of the example anchors 310a, 310b, and 310c is shown as including anchor portions designed for atraumatic contact with body tissue, in other implementations a portion of the corresponding anchor feature could include a sharp tip or barb designed to penetrate body tissue, for example.

FIGS. 4A-4D are side views of example fixation anchors 410a, 410b, 410c, and 410d, respectively. Each of the anchors 410a, 410b, 410c, and 410d may be considered micro-coil anchors, and each includes an active anchor portion 418. Each of the anchors 410a, 410b, 410c, and 410d comprises an elongate member, such as a wire, and includes an anchor portion 418 adapted to pierce body tissue at a deployment site to anchor the device and minimize or prevent migration of the device following deployment. Each of the frame attachment portions 416 of the fixation anchor wire are wrapped or coiled around a corresponding frame-defining elongate member 302 of a medical device. In some implementations, frame attachment portion 416 and/or the corresponding portion of the elongate member 302 can be coated with FEP or another appropriate adhesive material to secure the frame attachment portion 416 of the fixation anchor 410 to the elongate member 302 of the frame, and in some implementations the wire is coiled around the elongate member 302 without addition of FEP or other adhesive. In some examples, the anchors can be welded or soldered to the elongate members.

Figure 4A:
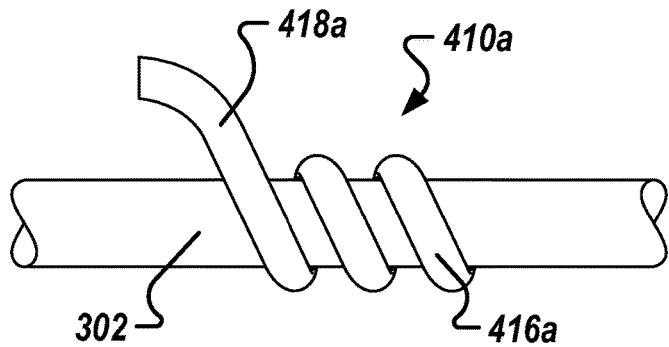
Figure 4B:
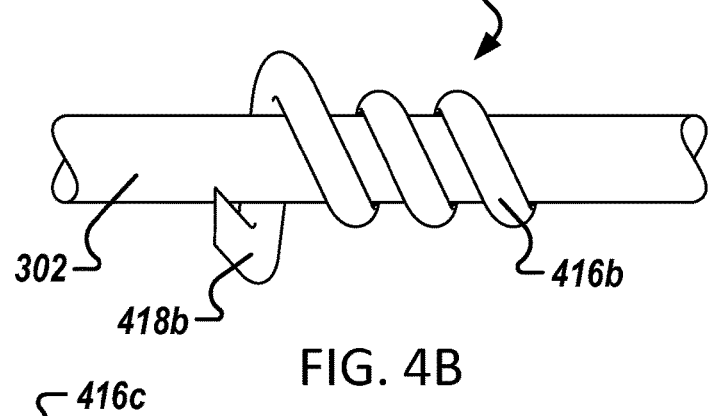
Figure 4C:
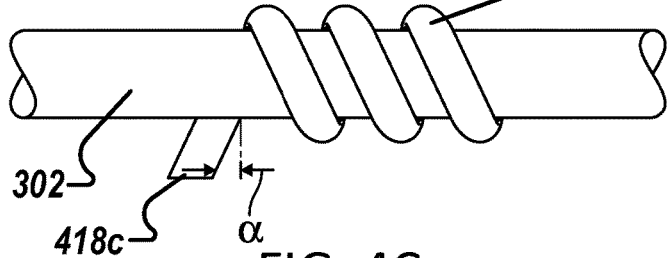
Figure 4D:
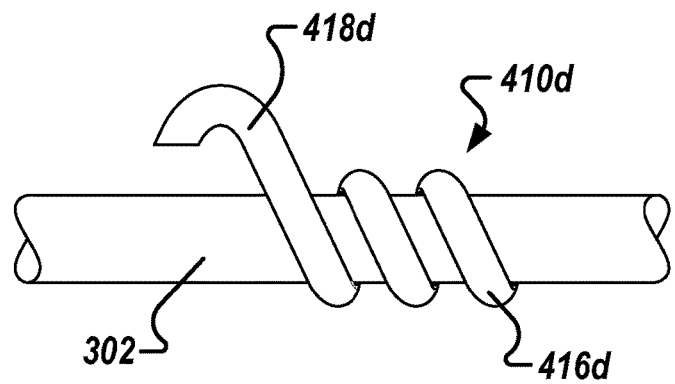

With reference to FIG. 4A, anchor portion 418a comprises an axial-facing barb. In some examples, the barb of anchor portion 418a is axially facing, and may engage axially and prevent migration in the axial direction. The anchor 410b of FIG. 4B includes a corkscrew-style anchor portion 418b. The corkscrew-style anchor portion 418c may engage tissue with a rotation of the frame of the device. The anchor 410c of FIG. 4C includes an anchor portion 418c that is skewed or angled from perpendicular by an angle alpha ($\alpha$), which may be adjusted based on desired engagement characteristics, for example. In some examples, angle $\alpha$ can range from zero to 45 degrees (e.g., 0 degrees, 10 degrees, 20 degrees, 30 degrees, 40 degrees, 45 degrees). The anchor portion 418c may engage tissue at a desired angle based on choice of $\alpha$, in some implementations. The anchor 410d of FIG. 4D includes an anchor portion 418d shaped generally like a "J" that is adapted to pierce through a tissue surface, extend a distance into the tissue, and then re-pierce the tissue surface, gathering tissue in the process. In some implementations, this may prevent further cutting or shearing of tissue, for example. In general, active anchor portions can be adapted to penetrate tissue to only a predetermined distance, for example.

FIGS. 5A-5D are side views of example fixation anchors 510a, 510b, 510c, and 510d, respectively. Each of the anchors 510a, 510b, 510c, and 510d may be considered micro-coil anchors, and each includes an active anchor portion 518 with multiple tissue piercing members. Each of the anchors 510a, 510b, 510c, and 510d comprises one or two elongate members, such as a wire(s), and includes an anchor portion 518 adapted to pierce body tissue at a deployment site to anchor the device and minimize or prevent migration of the device following deployment. Each of the frame attachment portions 516 of the fixation anchor wire are wrapped or coiled around a corresponding frame-defining elongate member 302 of a medical device. In some implementations, frame attachment portion 516 and/or the corresponding portion of the elongate member 302 can be coated with FEP or another appropriate adhesive material to secure the frame attachment portion 516 of the fixation anchor 510 to the elongate member 302 of the frame, and in some implementations the wire is coiled around the elongate member 302 without addition of FEP or other adhesive. In some examples, the anchors can be welded or soldered to the elongate members.

Figure 5A:
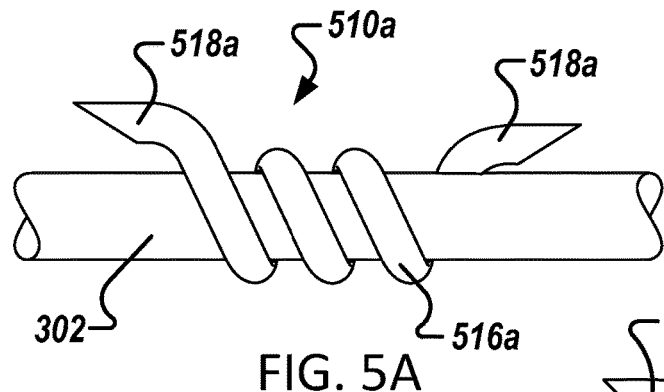
Figure 5B:
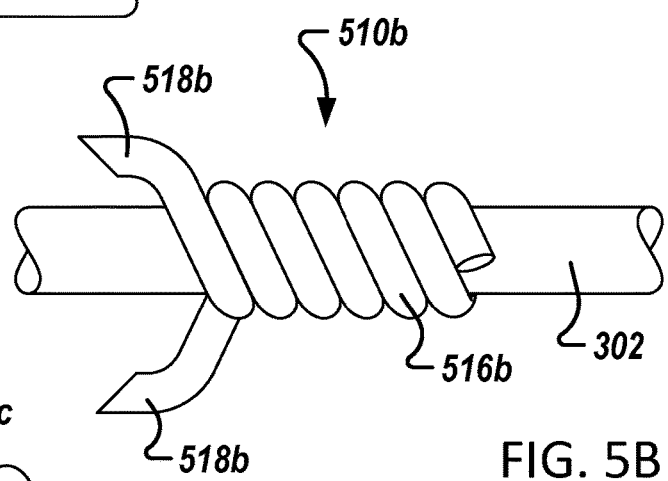

With reference to FIG. 5A, the anchor comprises a single anchor wire, and includes an anchor portion 518a that comprises two distinct barbs, one facing forward and the other facing backward along the elongate member 302. In some examples, the barbs of anchor portion 518a are axially facing in opposite directions (i.e., in axially opposed directions), and may engage axially and prevent migration in each direction of the axial dimension. The two barbs of anchor portion 518c may be the opposite ends of the single anchor wire. The anchor 510b of FIG. 5B includes two anchor wires, and includes an anchor portion 518b that comprises two distinct barbs, each facing axially in the same direction, and spaced generally about 180 degrees apart. Each of the anchor wires includes a frame anchor portion 516b. Anchor 510b may be considered a dual-filar anchor because it includes two anchor wires.

Figure 5C:
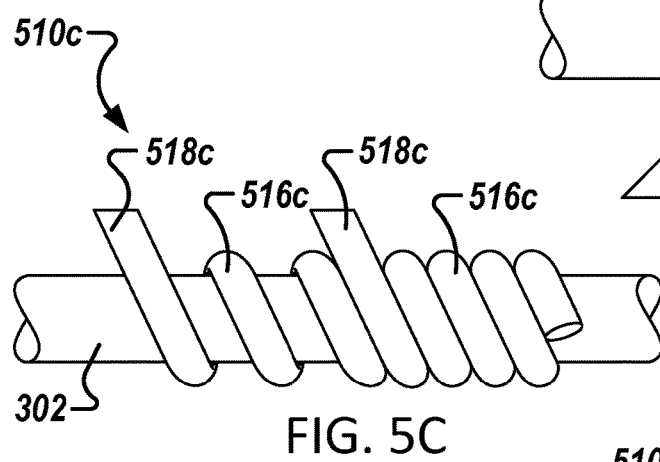
Figure 5D:
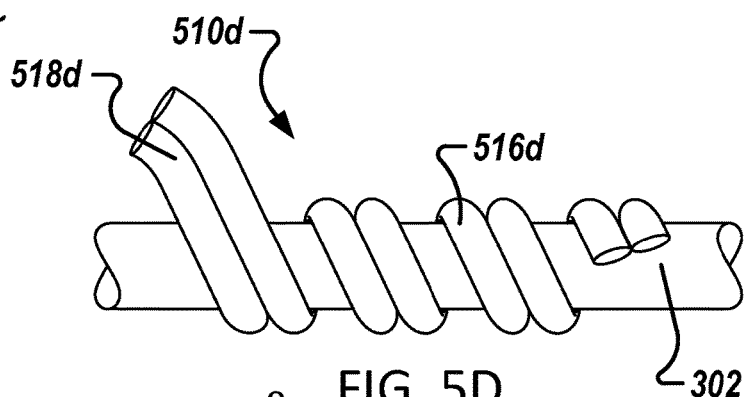

The anchor 510c of FIG. 5C includes two anchor wires, and includes an anchor portion 518c that comprises two distinct barbs, the two barbs located at different longitudinal locations along the elongate member 302. Anchor 510c may be a dual-filar, longitudinal release anchor. The anchor 510d of FIG. 5D includes two anchor wires that are paired or routed generally in contact with one another. This may increase stiffness of the anchor 510d while maintaining a low profile with the frame, in some implementations. Anchor portion 518d includes a bend, and the two wires may be welded or soldered together at the bend. The bend may be at various angles, and may be in the axial direction. In some implementations, anchor 510d may be formed to have a passive anchor portion, as by looping the paired wires in a similar fashion as the anchors depicted in FIGS. 3A-3C rather than terminating them in a barb. The frame attachment portion 516 of the paired wire embodiment includes an open pitch, which may facilitate adhesive attachment to the frame.

Figure 5E:
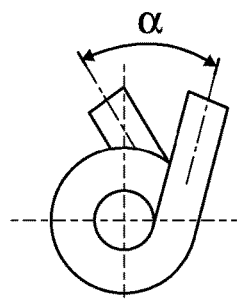
FIGS. 5E and 5F are end views of example fixation anchors.
Figure 5F:
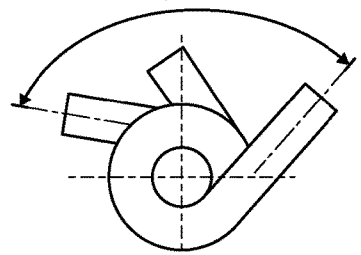

FIGS. 5E and 5F are end views of example fixation anchors, and illustrate that for anchor portions that include one, two, or three barbs, the barbs may be oriented at various angular positions. FIG. 5E illustrates a first angle $\alpha$ that separates two barbs of a representative anchor. FIG. 5F illustrates a second angle $\beta$ that separates two barbs of a representative anchor, where $\beta$ is larger than $\alpha$. A larger angle between barbs of an anchor may provide more anchor sweep or more anchor coverage, in some examples.

FIGS. 6A and 6B are side views of example anchor attachment portions 616a and 616b, respectively, of example fixation anchors. Anchor attachment portions 616a and 616b illustrate that the pitch of the anchor attachment portion for a given fixation anchor may be varied along the anchor attachment portion. The anchor attachment portion 616a includes a transition from a relatively tighter pitch to a relatively looser pitch, while anchor attachment portion 616b shows a transition from a relatively looser pitch to a relatively tighter pitch. In some examples, pitch tightening can improve attachment and may help prevent embolization of the anchor.

In general, anchor attachment portions for any of the micro-coil anchors discussed herein may be threaded with either a right-hand or left-hand direction. Also, the pitch of the micro-coil anchor attachment portion may be constant, in some embodiments, or may be varied in some embodiments as described above with reference to FIGS. 6A and 6B. An anchor with an anchor attachment portion having a tighter pitch may be less prone to fracture, in some implementations, and in some cases a smaller diameter anchor wire may be used for micro-coil anchors having tighter pitches. A looser or more open pitch may provide a looser fit to the frame, and can be easier to thread onto the frame in some cases. Pitch ranges for the attachment portion of the micro-coil anchor may generally range from about 0.006" to about 0.030" in some embodiments. One example of a relatively tighter pitch for the frame attachment portion of a micro-coil anchor is 0.008". One example of a relatively more open pitch for the frame attachment portion of a micro-coil anchor is 0.025". Diameters of the anchor frame wires may generally range from about 0.005" to about 0.010", for example, and in some embodiments the diameter of the anchor frame wires is approximately 0.008". Other anchor frame wire diameters can be used.

For active anchor portions that include one or more barbs, a barb length and a grind angle of the barb may be selected based on tissue penetration characteristics. FIG. 6C shows a barb with a flat grind, which can be advantageous for rotational fixation relative to the frame axis, in some implementations. FIG. 6D depicts an angled grind (regular cut in solid; reverse cut in dashed lines), which can be advantageous for straight in and out movement. FIG. 6E illustrates a bow cut, which can provide good anchoring capability while being relatively atraumatic.

In some embodiments, drug eluting material may be coated on fixation anchors. For example, a heparin or steroid eluting drug can be mixed with a polymer to attain an appropriate dosage of the drug. For active frame anchor portions that include a barb, for example, the tip of the barb may be dipped in the mixture. Alternatively, the entire micro-coil anchor may be dipped in the mixture, and then all but the tip of the barb may be covered with a capping layer. For example, a final polymeric mix could be applied over the anchor (except for the anchor barb tip in some implementations) to create the capping layer. In some embodiments, an ePTFE film (e.g., open porous) may be used to pre-wrap the frame anchor wire initially, for example, to create a scaffold for the drug mixture to adhere to.

In some embodiments, fixation anchors described herein may be compliant, non-compliant, or partially compliant and partially non-compliant. In some embodiments, a portion or the entire surface of the fixation anchor may be coated with one or more biocompatible materials including a fluoropolymer (e.g., ePTFE or PTFE), a polyester, a silicone, a urethane, or another suitable biocompatible material. In some embodiments, coated portions of the fixation anchors may provide a substrate that promotes tissue ingrowth around the fixation anchors. In some embodiments, the coated portions of the fixation anchors substantially prevent tangling of fixation anchors amongst each other. In some embodiments, the covered portions of the fixation anchors minimize friction between the fixation anchors and a surrounding catheter wall, thereby aiding deployment of the device at a delivery site, or retrieval of the device from the delivery site following implantation. In some examples, the covered portion of the fixation anchors may limit the extent to which the fixation anchors can penetrate a tissue. In some embodiments, the covered portions of the fixation anchors may be impregnated with one or more drug substances that are released in situ to promote wound healing or reduce tissue inflammation. In some embodiments, the drug substance may be a corticosteroid, a human growth factor, an anti-mitotic agent, an antithrombotic agent, or dexamethasone sodium phosphate. In certain embodiments, the covered portions of the fixation anchors may provide texture that aids in securing the device to the surrounding tissue.

Fixation wire anchors may have any appropriate cross-sectional shape (e.g., circle, rectangle, semi-circle, triangle, oval, trapezoid, diamond, generally flat profile, and others). In some examples, the anchor wire may have a generally flat profile, as shown in FIG. 6F, or may have a shaped profile, such as a "D" shape, as shown in FIG. 6G. The wires used for the fixation wire anchors may be of the same or similar type to the elongate member or wire types described in any of the examples above.

FIGS. 7A-7E are views of example fixation anchors 710a-710e, respectively. Each of the example fixation anchors 710a-710e includes one or more fixation anchor wire that includes a generally spherical or ball end element 719. Each of the anchors 710a, 710b, 710c, 710d, and 710e may be considered micro-coil anchors, and each includes one or more passive anchor portions 718 that include a ball end 719, or generally spherically shaped end member, adapted for atraumatically engaging body tissue and securing the device in place, for example by friction, pressure, or entanglement. In some examples, the ball ends 719 may be formed on the end of the fixation anchor wire by laser welding. The ball ends 719 may provide anchoring and may reduce a potential for perforation or pericardial effusion, in some implementations. In general, the ball ends 719 or other passive anchor features discussed herein may cause less friction on an inside surface of a delivery sheath as compared to some active anchor elements with sharp edges, in some implementations, which may reduce particulation with respect to the delivery system in some cases.

In some embodiments, a diameter of the ball ends 719 may be about two times the diameter of the frame anchor wire. In some examples, the diameter of the ball end 719 may range from about 1× (with just a round wire end) to about 2× or 2.5× the diameter of the frame anchor wire, for example, the diameter may be about 1.5× the diameter of the frame anchor wire, or about 1.6×, 1.7×, 1.8×, or 1.9× the diameter of the frame anchor wire. The ball end may be created by applying a laser pulse to the end of the frame anchor wire, for example. For example, in some embodiments, spherical members or ball ends may be formed directly on ends of the frame anchor wires using a precision laser weld technique (e.g., using an Nd:YAG laser).

Each of the anchors 710a, 710b, 710c, 710d, and 710e comprises one or two elongate members, such as a wire(s). Each of the frame attachment portions 716 of the fixation anchor wire are wrapped or coiled around a corresponding frame-defining elongate member 702 of a medical device. In some implementations, frame attachment portion 716 and/or the corresponding portion of the elongate member 702 can be coated with FEP or another appropriate adhesive material to secure the frame attachment portion 716 of the fixation anchor 710 to the elongate member 702 of the frame, and in some implementations the wire is coiled around the elongate member 702 without addition of FEP or other adhesive. In some examples, the anchors can be welded or soldered to the elongate members.

Figure 7A:
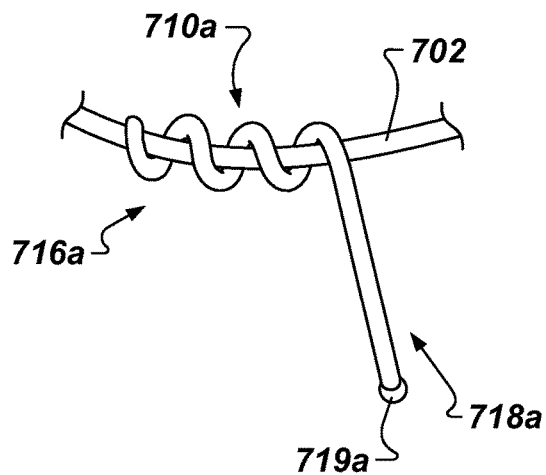
FIGS. 7A-7E are perspective views of example fixation anchors.
Figure 7B:
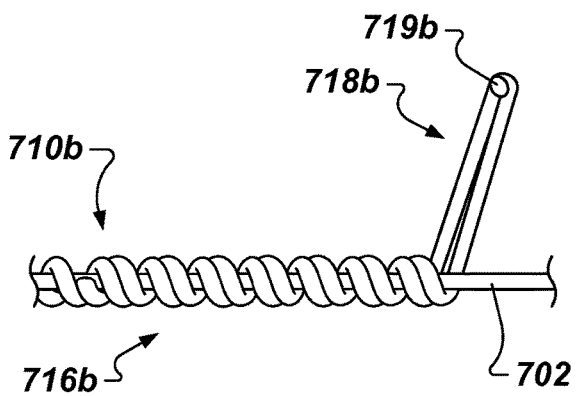
Figure 7C:
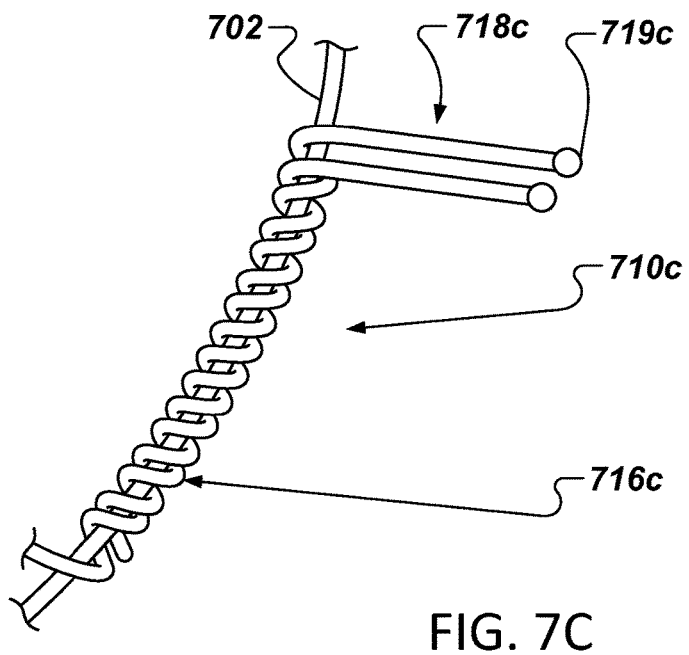
Figure 7D:
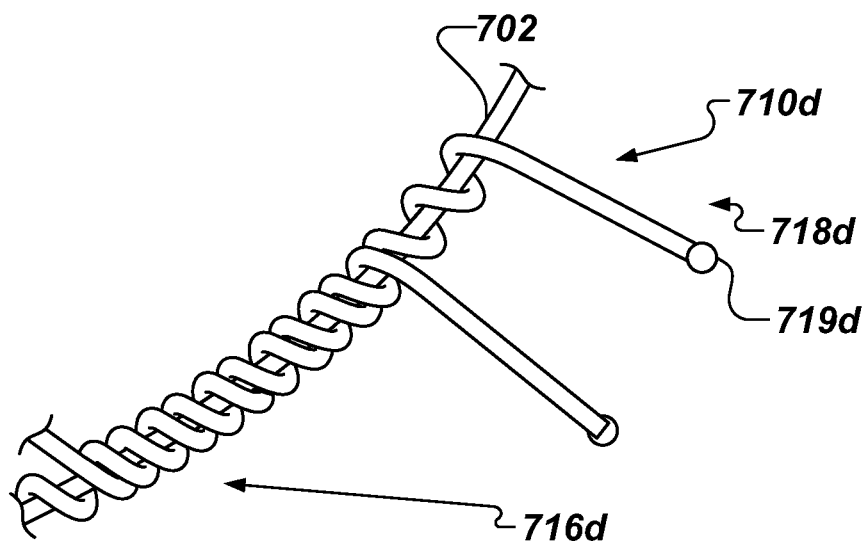
Figure 7E:
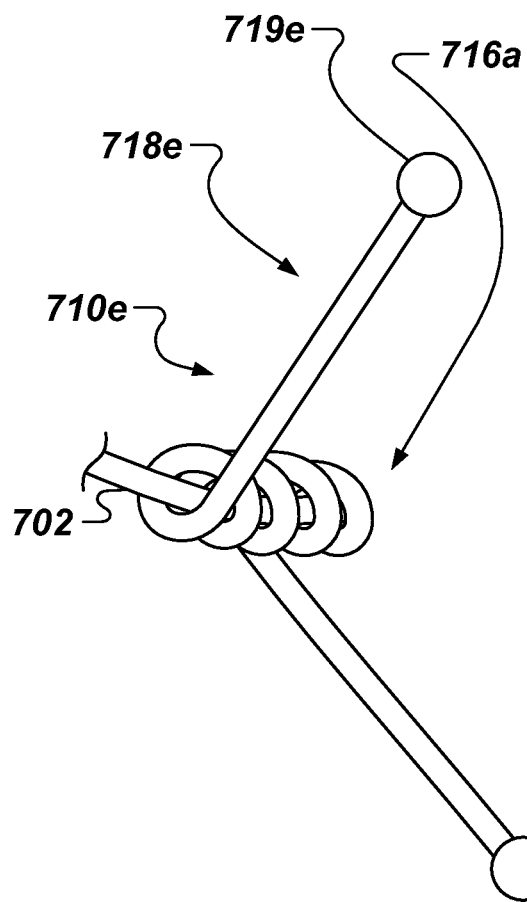

With reference to FIG. 7A, fixation anchor 710a includes a single fixation anchor wire, a portion of which forms the frame attachment portion 716a and a portion of which forms the anchor portion 718a, which includes a ball end 719a. Anchors 710b-710e of FIGS. 7B-7E, respectively, each include two frame anchor wires, and each includes two frame anchor portions 718 with ball ends. As can be seen with reference to FIGS. 7B, 7C, and 7D, longitudinal spacing of the two anchor portions 718 can be varied: the two anchor portions 718b of anchor 710b are generally in contact with one another, and in some cases can be welded or soldered together (e.g., at the ball ends 719b and/or at another portion of the anchor portions 718b) to provide added stiffness to the anchor 710b; the two anchor portions 718c of anchor 710c are spaced apart from one another a short longitudinal distance along the elongate member 702, providing a generally tight spacing of the frame anchor portions 718c; and the two anchor portions 718d of anchor 710d are spaced apart a greater longitudinal distance along the elongate member 702. Other spacing options can similarly be used. While the anchor portions 718b, 718c, and 718d generally extend parallel with one another, anchor 710e of FIG. 7E demonstrates that the two anchor portions 718e may include an angle between them.

Figure 8A:
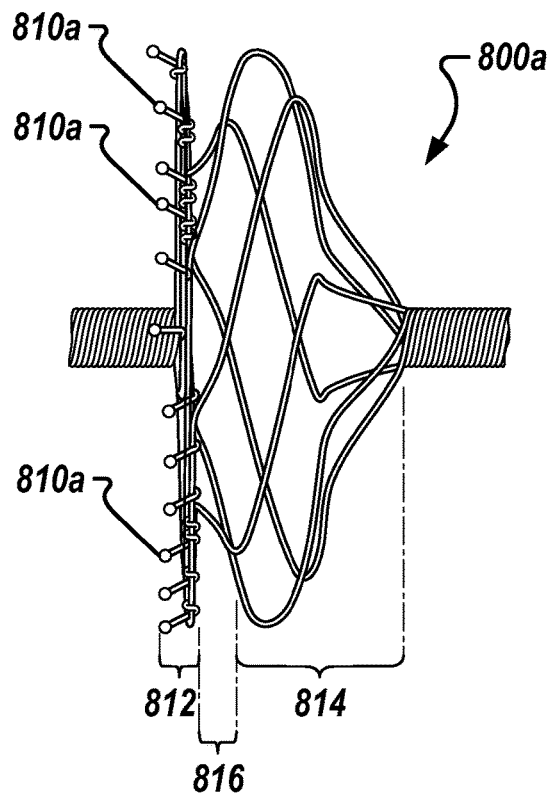
FIGS. 8A-8C are side views of example occlusion devices, and illustrate various example anchor locations.
Figure 8B:
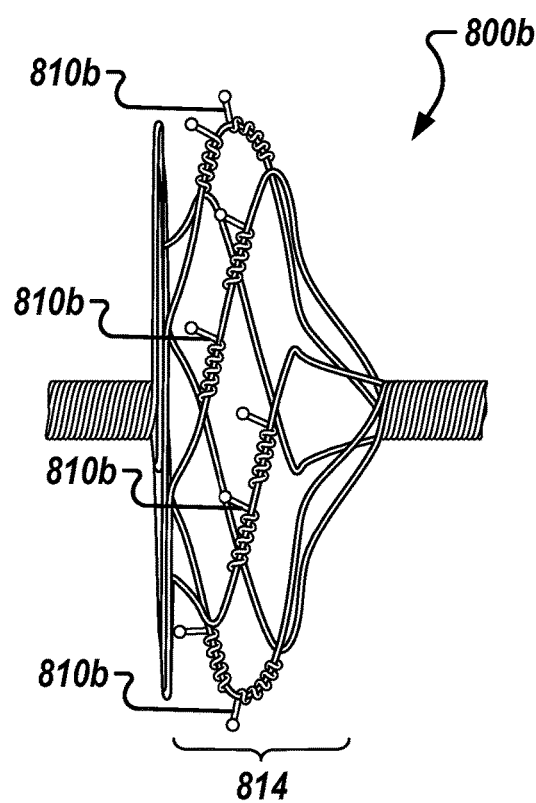
Figure 8C:
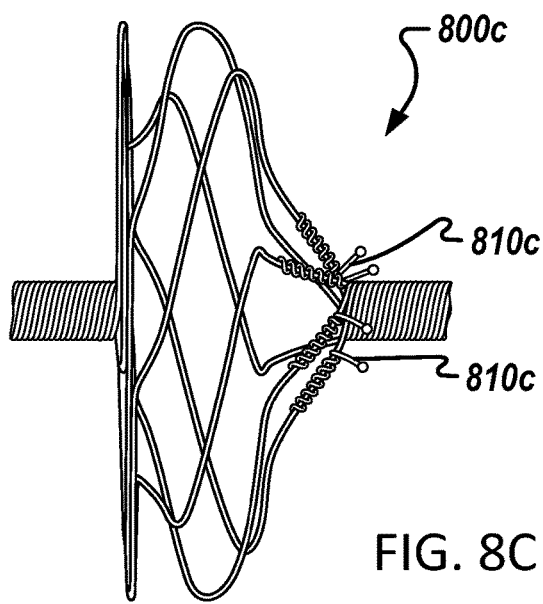

FIGS. 8A-8C are side views of an example occlusion device 800a-800c, respectively, and illustrate various example anchor locations. The anchors 810 may generally represent any of the anchors discussed herein. Device 800a of FIG. 8A includes anchors 810a positioned on a proximal disc of the device, within a proximal region 812 of the device. In some examples, the anchors 810a may be located on a proximal face of the proximal disc, or at a periphery of the proximal face, for example. The location of anchors 810a may facilitate anchoring to the ostium of the LAA, in some implementations. An angle at which the anchors extend from the frame can be varied as desired.

Device 800b of FIG. 8B includes anchors 810b positioned on a support portion of the device, within a distal region 814 of the device. The location of anchors 810b may facilitate anchoring deeper into the LAA, in some implementations, or deeper into a vessel for applications intended to occlude a vessel. Device 800c of FIG. 8C includes anchors 810c positioned near the distal end of the support portion of the device in the distal region 814 of the device. The location of anchors 810c may facilitate early anchoring at a deployment site as the device 800c is deployed from a delivery system in implementations where the distal end of the device is deployed first. This may increase the chance of holding the device in the desired position as it deploys, improve accuracy, and reduce the possibility or migration of the device. The location of anchors 810c may also facilitate anchoring even deeper into the LAA, in some implementations, or even deeper into a vessel for applications intended to occlude a vessel. Anchors 810c may also provide added stiffness to the frame of the device.

As can be seen with reference to the example occlusion devices 800a, 800b, and 800c, the frame of the device may generally have shapes, such as a "bell" shape, a cylindrical shape, a tapered shape, or other appropriate shape-filling shape. The proximal disc may have a generally planar shape in some embodiments, and in some embodiments may have a concave shape or a convex shape. I.e., the proximal disc may be "cupped" in the distal direction, or in the proximal direction. In some examples, wire portions that extend radially from an eyelet to a rim of the device may include a looped shape, such as generally an "S-shape" or other appropriate looped shape. The proximal disc may seal to the ostium of the LAA and may prevent leakage of fluid or material from within the LAA to the left atrial heart chamber.

Figure 8D:
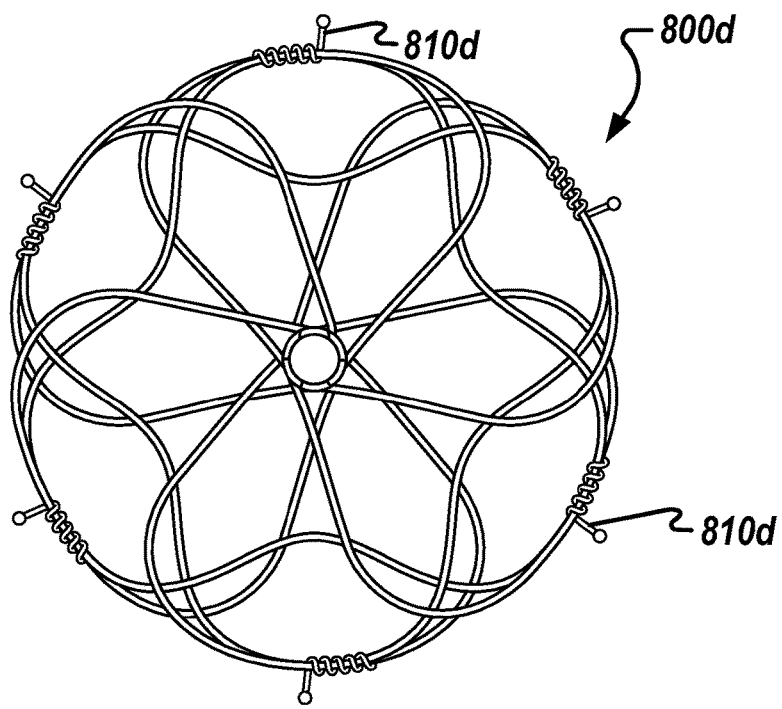
FIGS. 8D and 8E are proximal-end views example occlusion devices, and illustrate various example anchor locations.
Figure 8E:
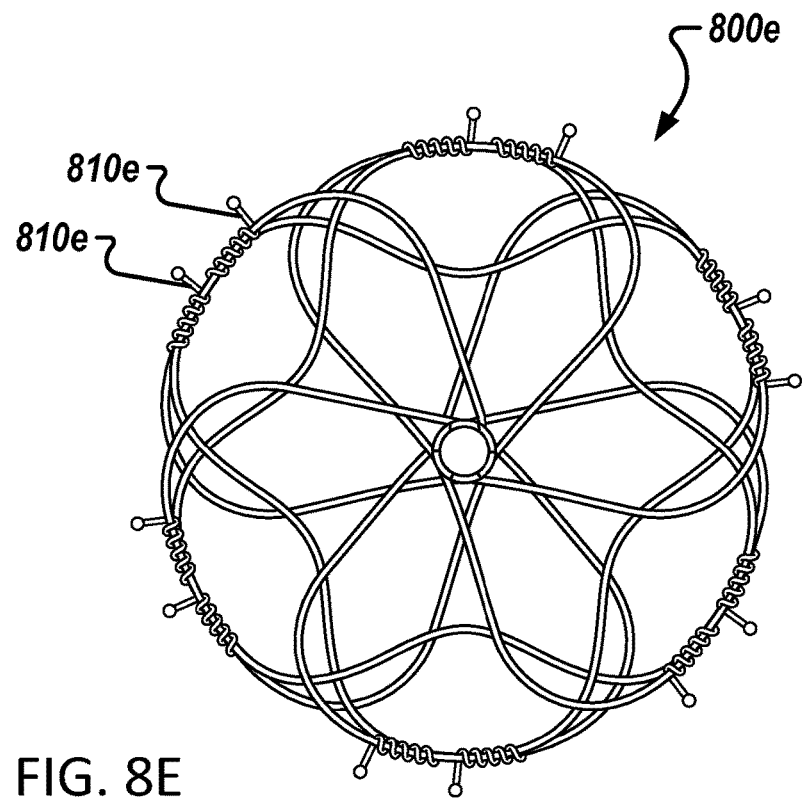

FIGS. 8D and 8E are proximal-end views of example occlusion devices 800d and 800e, respectively, and illustrate various example anchor locations. The anchors 810 may generally represent any of the anchors discussed herein. Device 800d of FIG. 8D includes anchors 810d positioned on a proximal disc of the device, and includes one anchor 810d per petal of the proximal disc. Device 800e of FIG. 8E includes anchors 810e positioned on a proximal disc of the device, and includes two anchors 810e per petal of the proximal disc. In other examples, three or more anchors 810 may be included per petal of the disc. In some examples, one or more petals of the disc does not include an anchor 810.

In general, spacing of anchors with respect to one another, or with respect to features of the device frame, may be uniform or non-uniform. In general, the anchors describe herein, and in particular frame attachment portions of the anchors described herein, may be located across a bend in the frame-defining elongate member to which the frame attachment portion is attached. Such a bend can be located on any portion of the device, such as the occlusive portion or the support portion, for example.

Figure 9:
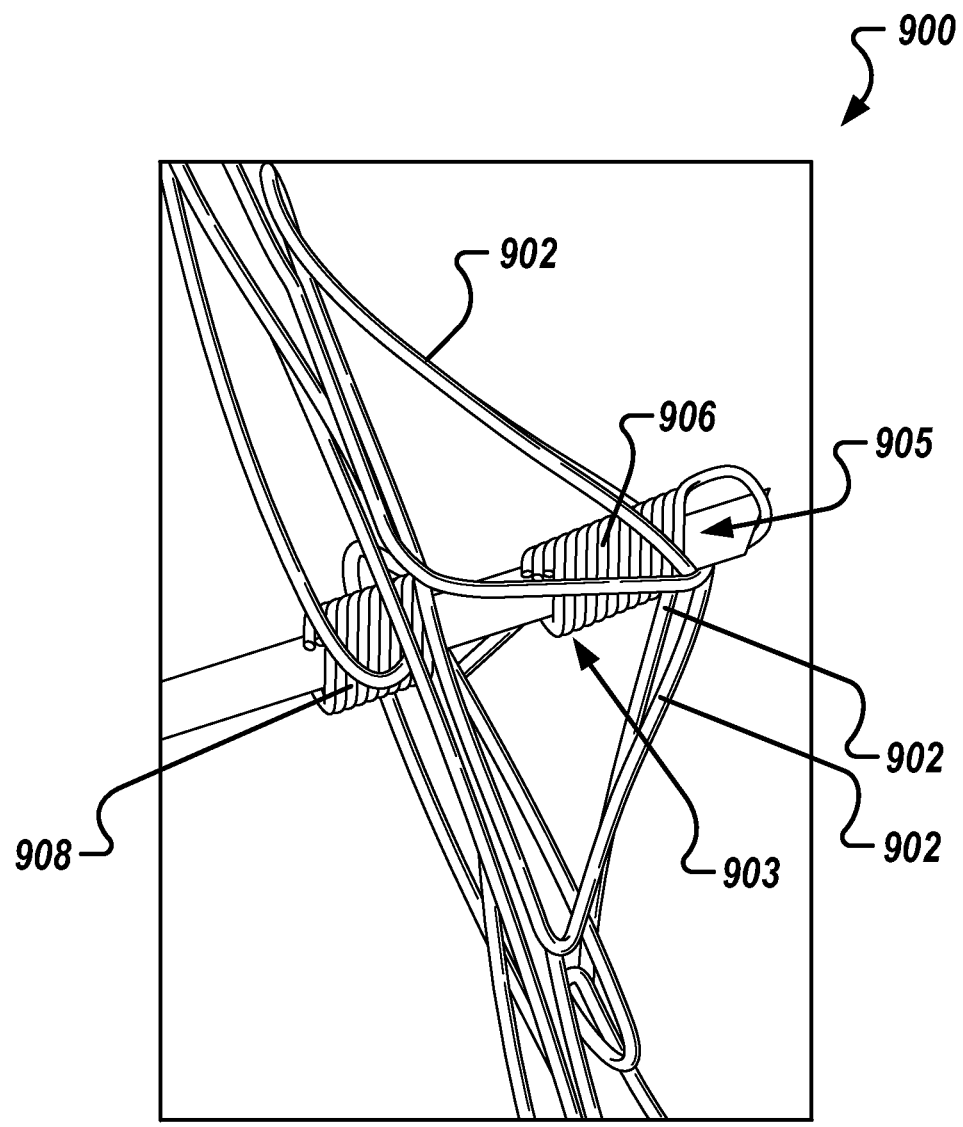
FIG. 9 is a side view of an example occlusion device frame that includes an inverted eyelet.

FIG. 9 is a side view of an example occlusion device frame 900 that includes an inverted eyelet 906. In this example, the distal eyelet 906 is inverted, and is located between a distal end of the frame portion of the device and the proximal eyelet 908. For example, inverted distal eyelet 906 does not protrude distally of the frame of the device, but rather is positioned within a space defined by the support portion of the frame of the device 900. Inverted distal eyelet 906 may reduce or eliminate pressure or force on the endocardium where the distal disc interfaces with the heart wall in LAA occlusion applications, for example, as compared to distally extending eyelets, in some implementations. This can reduce or eliminate abrasion to the pericardium or other surrounding cardiac structures, for example. In general, the inverted eyelet 906 may be substituted for any of the distal eyelets discussed with any of the frames or devices discussed herein. In some examples, an inverted eyelet can be used to replace a proximally-extending proximal eyelet. An inverted proximal eyelet (not shown) would not protrude proximally of the frame of the device, but rather would be positioned within a space defined by the frame of the device. An inverted proximal eyelet may be oriented toward a center region of the device, for example. In embodiments that include an inverted proximal eyelet, blood flow disturbance may be minimized or eliminated by reducing or eliminating eyelet extension in the proximal direction beyond the generally planar proximal occlusion disc. This may act to eliminate a source for thrombus formation, for example.

Devices that include an inverted eyelet, such as eyelet 906, can be wound differently than devices that do not include an inverted eyelet. For example, in the case of an inverted distal eyelet, frame-defining elongate elements 902 of the device may be used to wind the inverted eyelet downwards, or in a distal direction, rather than upwards, or in a proximal direction. That is, first ends of the elongate members 902 may be wrapped or coiled around a rod or mandrel, where the elongate member end portions generally form the proximal end 903 of the inverted eyelet 906 initially. When a desired length of the inverted eyelet 906 has been reached, the elongate members may be fanned out from the distal end 905 of the inverted eyelet 906. In this manner, the elongate members 902 may extend from the inverted eyelet 906 from the distal-most end 905 of the inverted eyelet 906, and may not extend from the proximal end 903 of the distal eyelet, according to some implementations.

Frame 900 includes two eyelets, where eyelet 906 is wound downward or in a distal direction, and eyelet 908 is wound upwards or in a proximal direction. As such the eyelets 906 and 908 are wound in opposite directions. Also, inverted eyelet 906 is wound such that it occupies a space interior of the frame, without having to be pushed into the interior space after having been wound outside of the space interior of the frame, for example.

When deploying or elongating the frame 900, inverted eyelet 906 is maintained in compression (without being urged to elongate by the applied force), in contrast to a traditional external distal eyelet where, when the frame is elongated, the force involved in elongating the device also acts to elongate the traditional external distal eyelet. In some implementations, this may encourage device integrity, for example.

After the inverted eyelet 906 has been formed, one or more features of a first region (e.g., the distal region) may be wound; one or more features of a second region (e.g. the proximal region) may be wound; and a second eyelet (e.g., the proximal eyelet) may be wound. In some examples, one or more features of a third region (e.g., the transitional region) may involve an additional winding step, and in the example above the additional winding step could occur after the step of winding the feature of the first region. In general, winding steps for devices that include an inverted distal eyelet may be similar to those steps for devices that do not include an inverted distal eyelet, except that the inverted eyelet may be wound down, or in a distal direction, rather than in an up or proximal direction. Stated another way, the inverted eyelet may be wound in a direction away from an interior of the device.

Figure 17:
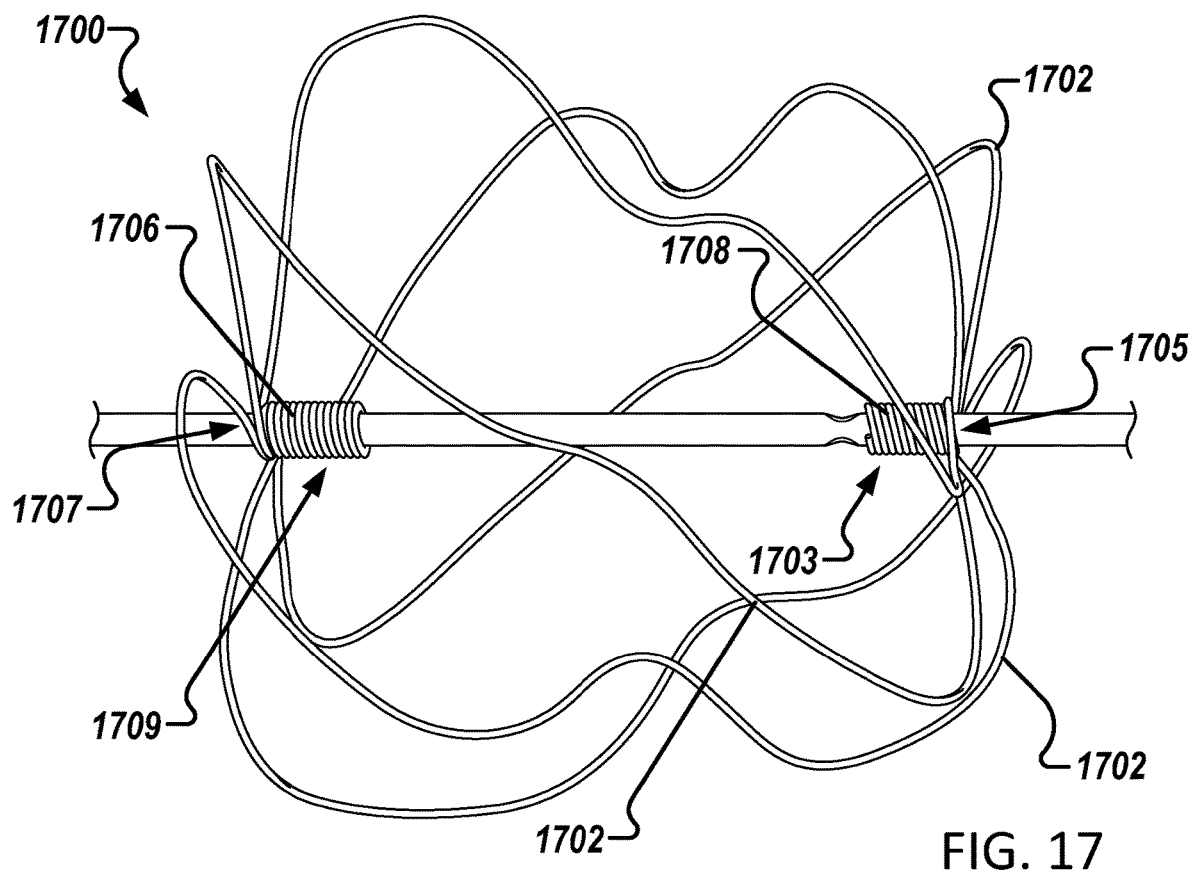
FIG. 17 is a view of an example occlusion device frame that includes two inverted eyelets.

FIG. 17 is a view of an example occlusion device frame 1700 that includes two inverted eyelets 1706 and 1708. In this example, both the distal eyelet 1708 and the proximal eyelet 1706 are inverted. Each of the distal eyelet 1708 and the proximal eyelet 1706 are located in a space defined by the frame-defining elongate members 1702 of the frame 1700. Each of the distal eyelet 1708 and the proximal eyelet 1706 are located between a distal end of the frame portion of the device and a proximal end of the frame portion of the device. For example, inverted distal eyelet 1708 does not protrude distally of the frame of the device, but rather is positioned within a space defined by the support portion of the frame of the device 1700. Similarly, inverted proximal eyelet 1706 does not protrude proximally of the frame of the device, but rather is positioned within a space defined by the occlusion portion of the frame of the device 1700. The elongate members 1702 may extend from the inverted distal eyelet 1708 from the distal-most end 1705 of the inverted eyelet 1708, and may not extend from the proximal end 1703 of the distal eyelet 1708, according to some implementations. Similarly, the elongate members 1702 may enter the inverted proximal eyelet 1706 from the proximal-most end 1707 of the inverted proximal eyelet 1706, and may not enter from the distal end 1709 of the proximal eyelet 1706, according to some implementations. The inverted eyelets of frame 1700 may provide the same or similar benefits as described above with reference to the frame 900, for example.

Frame 1700 can be wound similarly to frame 900, except that proximal eyelet 1706 can be wound downwards, or in a distal fashion (where non-inverted proximal eyelet 908 of frame 900 was wound upwards or in a proximal direction). As such the eyelets 1706 and 1708 are wound in the same directions. Also, each of inverted eyelets 1706 and 1708 is wound such that it occupies a space interior of the frame, without having to be pushed into the interior space after having been wound outside of the space interior of the frame, for example. When deploying or elongating the frame 1700, the inverted eyelets 1706 and 1708 are maintained in compression (without being urged to elongate by the applied force), which may improve device integrity, for example.

Figure 10A:
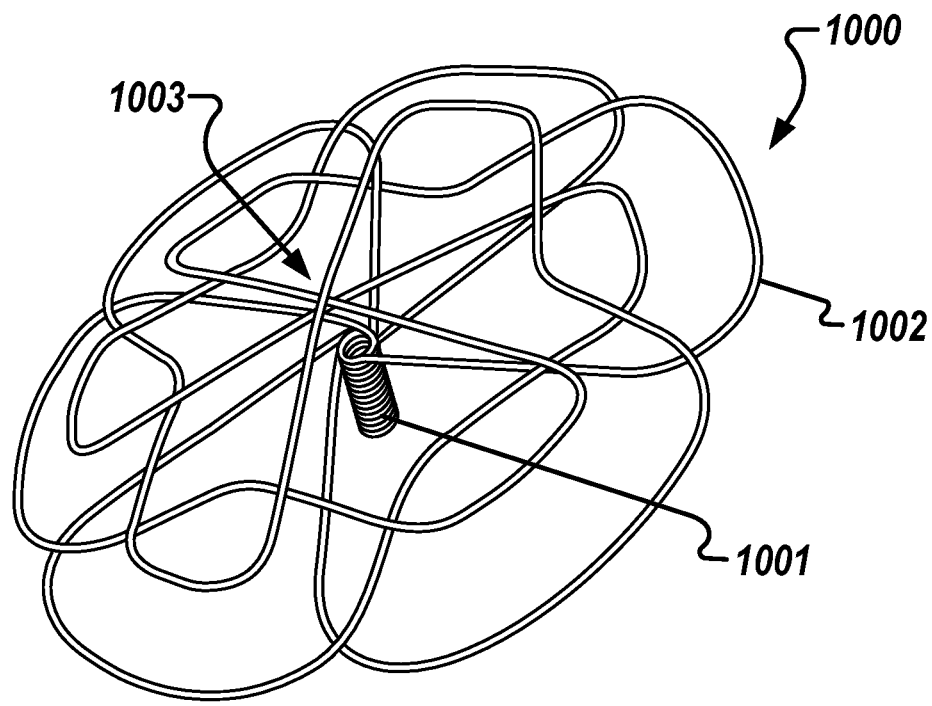
FIGS. 10A and 10B are perspective views of example occlusion device frames that include a single eyelet.

FIG. 10A is a perspective view of an example occlusion device frame 1000 that includes a single eyelet 1001. Eyelet 1001 may represent a proximal eyelet, in some implementations, and device 1000 does not include a distal eyelet. This device implementation may enjoy the same potential benefits as a device that employs an inverted distal eyelet, including reduced tissue contact pressure at the interface between the distal disc and heart tissue, for example. Frame 1000 is a three-wire device in this example, and the six wire ends (two ends for each wire) all terminate at the single eyelet 1001. That is, the wire ends for all frame-defining elongate elements 1002 terminate at a single eyelet 1001. In other examples frames including more or fewer than three wires can include a single eyelet, and all wire ends may terminate at the single eyelet.

Device 1000 may be wound differently than other devices described herein. For example, approximate midpoints of each of the elongate members 1002 may be aligned vertically at an aggregation point 1003, with the elongate members spaced by about 120 degrees from one another. Features of a first region (e.g., the distal region) may be wound where a single elongate member may now define two features in the first region (on either side of the approximate midpoint of the elongate member); next, features of a second region (e.g., the proximal region) may be wound, where again each elongate member may now define two features in the second region; next, both end portions of each elongate member may be wrapped or coiled around a bar or mandrel to form the single eyelet 1001.

Figure 10B:
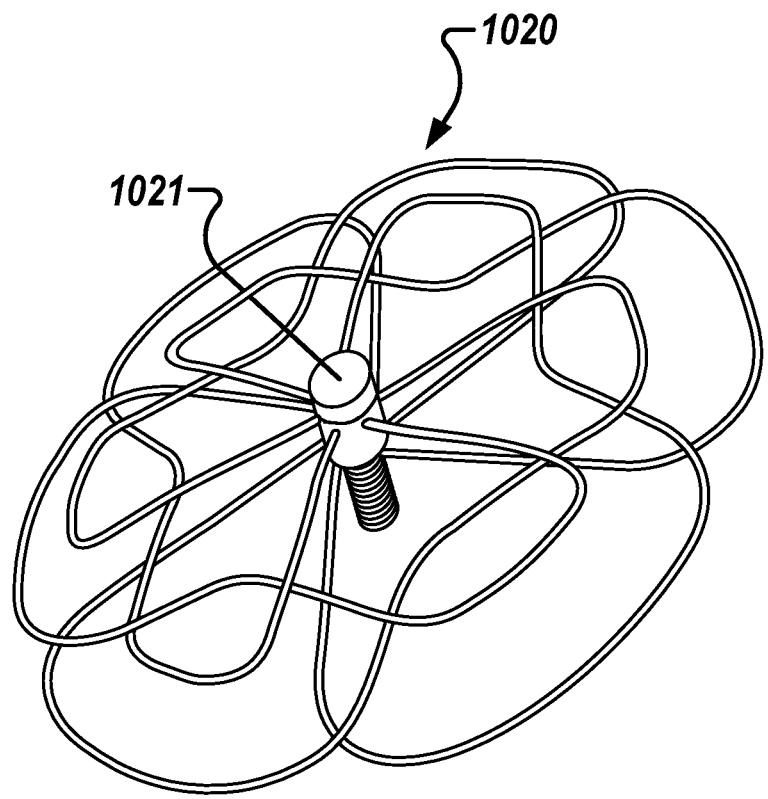

Frame 1020 of FIG. 10B is similar to frame 1000, but includes an engagement member 1021 that can engage the elongate members 1002 of the frame at or near the aggregation point 1003 (see FIG. 10A) while permitting the elongate members 1002 to pass through the engagement member 1021. The engagement member 1021 may provide stability to the frame in some implementations, and may provide an attachment point for a component of the delivery system, which may provide better control of the device during deployment. In general, the engagement member 1021 may sandwich the elongate members 1002, which may be tack-welded or soldered at an engagement point, for example. The engagement member 1021 may also encourage pivoting of the elongate members at the engagement member 1021, in some implementations.

Figure 10D:
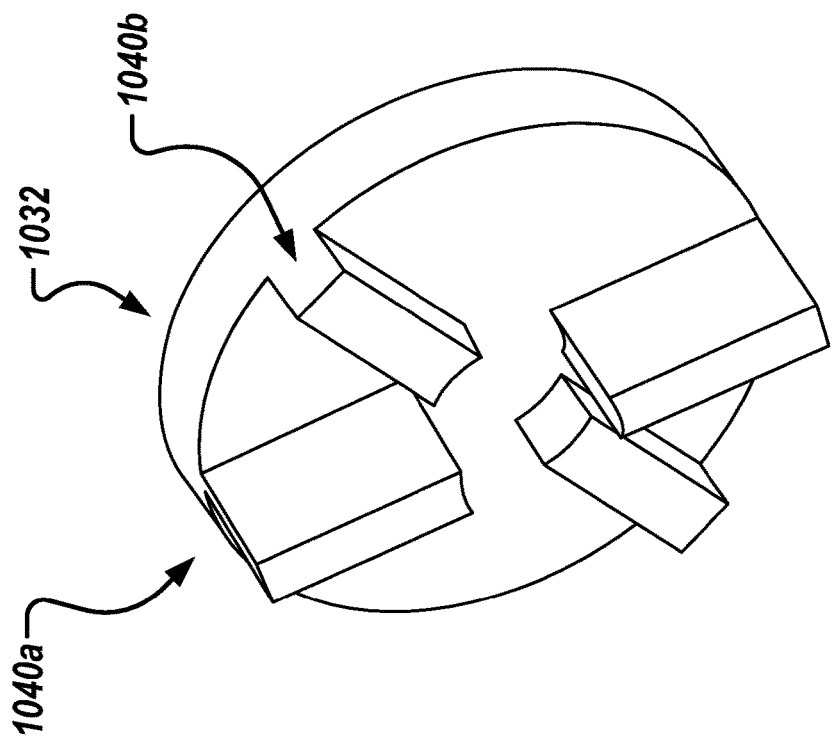
FIGS. 10C and 10D are views of example components that together comprise an engagement member of FIG. 10b.
Figure 10C:
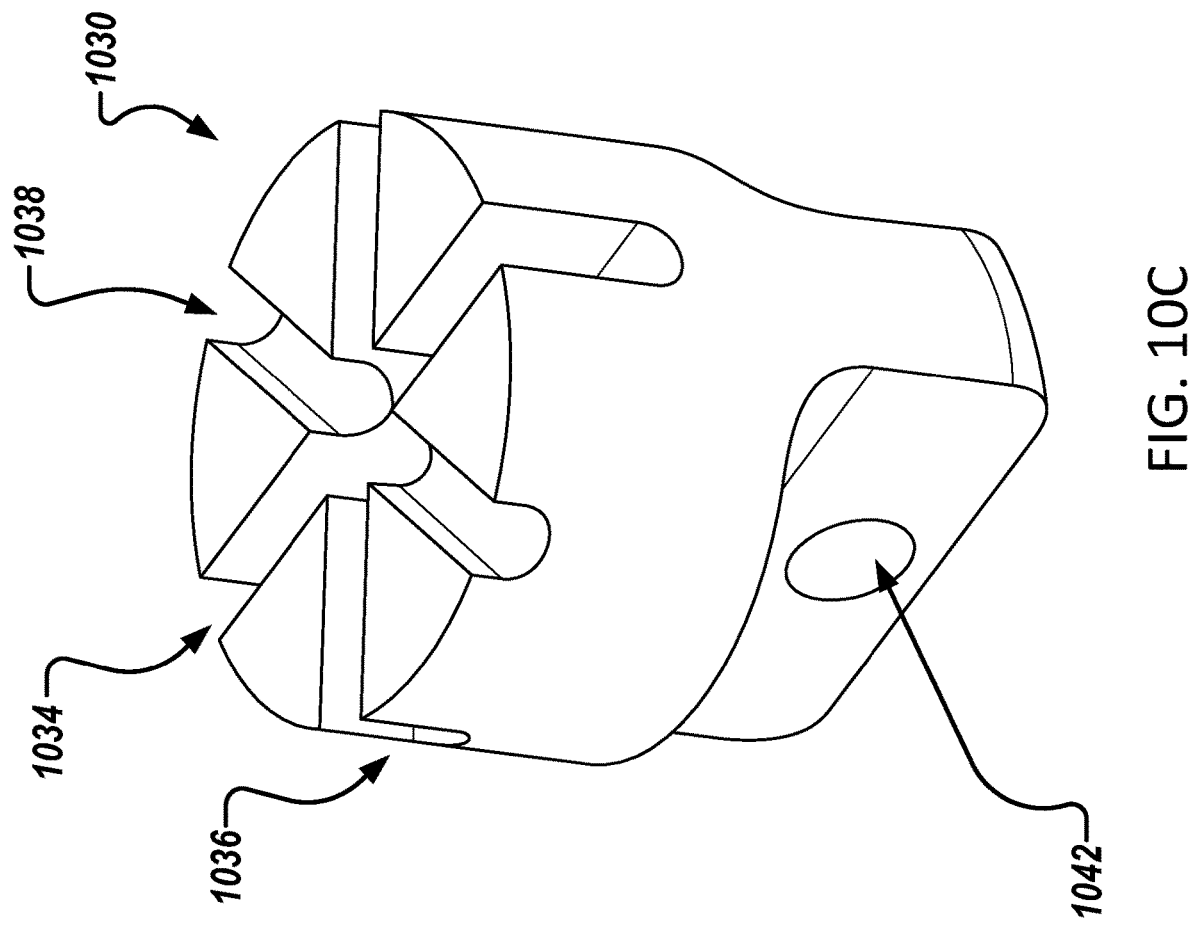

FIGS. 10C and 10D are views of example components 1030 and 1032, respectively, that together comprise the engagement member 1021 of FIG. 10B. As described above, device 1000 is a three-wire device, and component 1030 includes a first channel 1034, a second channel 1036, and a third channel 1038. The first channel 1034 can house a portion of a first wire of the three-wire device 1000; the second channel 1036 can house a portion of a second wire of the three-wire device 1000; and the third channel 1038 can house a portion of a third wire of the three-wire device 1000. As can be seen in FIG. 10C, the three channels 1034, 1036, and 1038 are arranged at different depths within the component 1030. The first channel 1034 is at a relatively deep depth within the component 1030; the third channel 1038 is at a relatively shallow depth within the component 1030, and the second channel 1036 is at a depth between the depths of the first channel 1034 and the third channel 1038. After portions of the three wires 1002 are located in the respective channels 1034, 1036, and 1038 of the component 1030, component 1032 is placed on top of component 1030, and the components 1030 and 1032 can be welded (e.g., tack-welded) together, or otherwise attached to one another. As can be seen in FIG. 10D, component 1032 includes one or more alignment members 1040, which can be aligned with the channels of component 1030. Components 1030 and 1032 can engage the wires 1002, and can permit stacking the wires 1002 at different heights, which can prevent or minimize interference among the wires 1002 or kinking of the wires 1002. Component 1030 includes an attachment feature 1042, to which a component of the delivery system may releasably attach in some implementations. In some embodiments, attachment feature 1042 may be located on the bottom of component 1030. In other embodiments, components 1030 and 1032 can be combined into a single component. In some embodiments, component 1030 could include fewer (e.g., two) or more (e.g., four, five, six, seven, eight, nine, ten, or more) channels, so that frames having any appropriate number of wires could be accommodated.

Figure 11A:
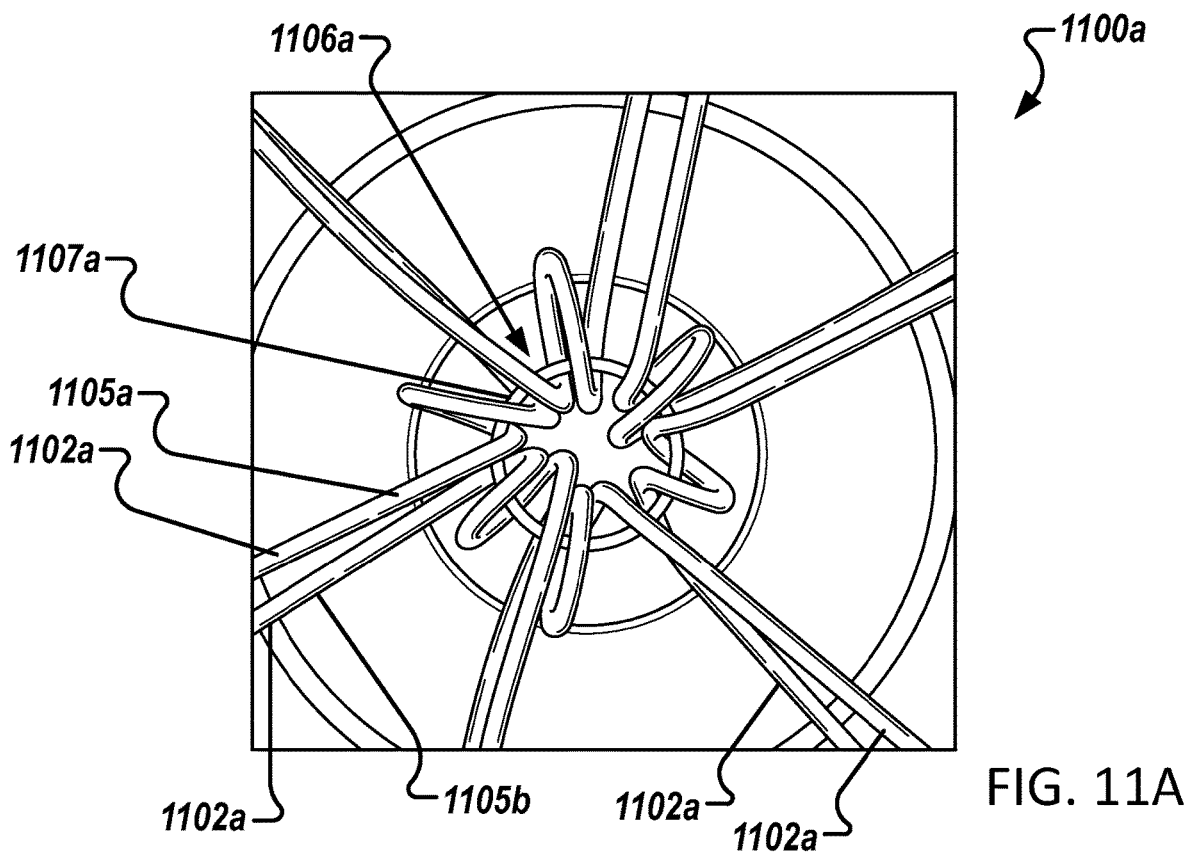
FIGS. 11A and 11B are views of portions of example occlusion device frames that include a hub feature in place of an eyelet.
Figure 11B:
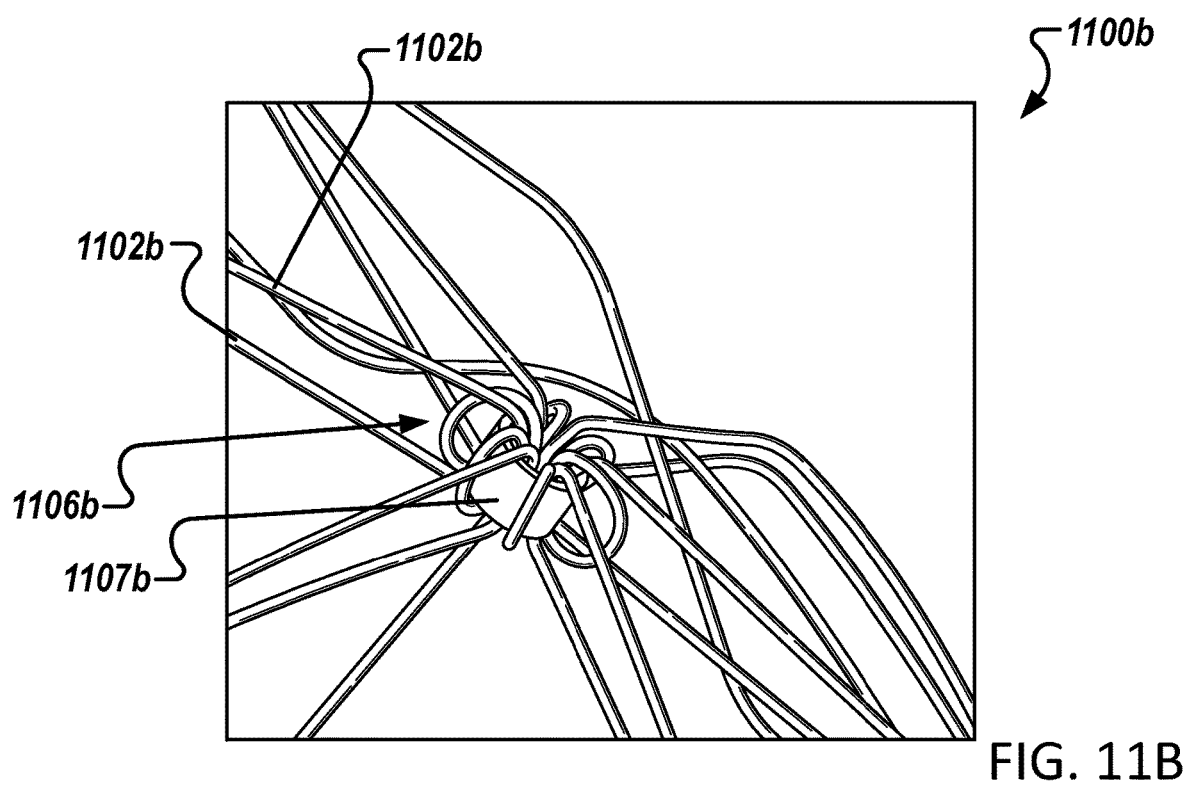

FIGS. 11A and 11B are views of portions of example occlusion device frames 1100a and 1100b that each include a hub feature 1106a and 1106b, respectively, instead of a distal eyelet. For example, the hub feature 1106 may replace a traditional distal eyelet on the occlusion device frame. With reference first to FIG. 11A, the hub feature 1106a includes a generally donut-shaped member 1107a, through which the elongate members 1102a of the frame 1100a are looped. For example, frame 1100a includes six elongate members 1102a, and each elongate member 1102a is passed through an interior space of the donut-shaped member 1107a twice. In assembling the frame 1100a, first ends of each of the elongate members 1102a may be passed through the interior space defined by the donut-shaped member 1107a, and then may be looped around the exterior of the donut-shaped member and passed through the interior space a second time. As can be seen with reference to FIG. 11A, a first portion 1105a and a second portion 1105b of each elongate member 1102a extends from the donut-shaped member 1107a. The first portion 1105a and the second portion 1105b of a given elongate member 1102a can then be wound to create a feature in a first region (e.g., the distal region) of the frame, and can next be wound to create a feature in a second region (e.g., the proximal region) of the frame. End portions or each of the first portion 1105a and the second portion 1105b may then be wrapped or coiled around a bar or mandrel to form an eyelet (e.g., the proximal eyelet).

The elongate members 1102a may generally pivot on or around the donut-shaped member 1107a, which may facilitate collapsing and expanding the frame 1100a, for example, for loading and deploying the device to/from a delivery system. For example, each of the elongate members 1102a may generally pivot around the donut shaped member 1107a.

In some implementations, each elongate member 1102a may pass through the interior space of the donut shaped member one time. In some implementations, each elongate member 1102a may pass through the interior space of the donut shaped member three times. In some implementations different elongate members 1102a may pass through the interior space of donut shaped member 1107a a different number of times (e.g., half of the elongate members pass through once and the other half of the elongate members pass through twice).

In some examples, the donut-shaped member has a rounded profile. For example, a cross-section of the donut-shaped member may be a circle, an oval, or an ellipse, in some embodiments. For implementations where the donut-shaped member has an elliptical cross-sectional shape, the long-radius of the ellipse may be oriented either generally radially or generally longitudinally with respect to the overall device, for example. In some examples, the donut-shaped member 1107a may include grooves, ridges, or slots, and the elongate members 1102a may generally be positioned within the grooves, ridges, or slots.

In some implementations, the donut shaped member has a partially round and partially flat profile, so that the elongate member can pivot a predetermined amount on a round profile portion of the donut shaped member and then be prevented from further pivoting by contacting a flat profile portion of the donut shaped member. In this manner, an angle or amount of pivoting may be controlled.

Frame 1100a may be considered a two-filar frame, because two wire portions (portions 1105a and 1105b) are used to make the features of the device. That is, for a given feature (e.g., a petal of the proximal disc or a support feature of the distal region of the frame), first and second elongate wire portions 1105a and 1105b are used to form the feature. In some implementations, two-filar frames can offer good fatigue resistance, for example. Moreover, frame 1100a may generally be considered a parallel two-filar frame, because the first and second elongate wire portions 1105a and 1105b generally run approximately parallel with one another.

In some implementations, each elongate member 1102a is passed once through the interior of donut shaped member 1107a, and then twisted one or more (e.g., one, two, three, or more) times by crossing the first portion 1105a and the second portion 1105b or the elongate member, before winding the device as described above. In some implementations, the one or more twists occur at various points along the device (e.g., at the donut-shaped member 1107a, in the distal region of the device, in the transitional region of the device, or in the proximal region of the device.

An interior diameter of the donut shaped member 1107a may be selected so that the various elongate member portions that pass through the interior region of the donut shaped member 1107a may generally be snugly positioned therein. For instance, the interior diameter of the donut shaped member may be selected so that the wire portions may remain generally uniformly spaced around the donut shaped member without gathering or bunching in a particular area of the donut shaped member, or separating and isolating in a particular area of the donut shaped member.

In some embodiments, the donut shaped member 1107a includes one or more through holes. Elongate members 1102a may individually pass through one or more through holes, for example, and the through holes may facilitate locking a portion of the elongate member in a particular orientation.

In some implementations, a twisted wire pair may be substituted for one or more of elongate members 1102a. One wire of the twisted pair may be used to follow the path of the device frame, while the other wire of the twisted pair may be used to create one or more fixation or anchor features for the device. For example, a fixation or anchor feature may be created in a distal region of the device using one wire of a twisted pair of wires. In some examples, the twisted pair wire used to make the fixation or anchor feature may terminate at the fixation or anchor feature, while in other examples it may re-join the other wire of the twisted pair on the frame path after forming the fixation or anchor feature.

FIG. 11B shows another example of a frame 1100b with a hub feature 1106b that replaces a distal eyelet. Alternatively, the hub feature 1106b may replace a proximal eyelet. The hub feature 1106b includes a generally donut-shaped member 1107b, through which the elongate members 1102b of the frame 1100b are looped.

Figure 11C:
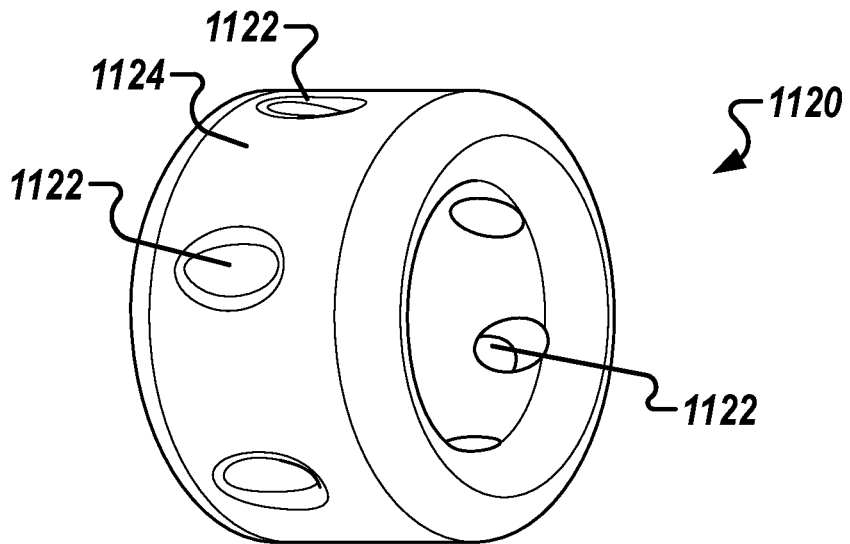
FIG. 11C is a view of another example hub feature.

FIG. 11C is a view of another example hub feature 1120. In general, hub feature 1120 can replace an eyelet (e.g., a distal eyelet or a proximal eyelet) in any of the example devices discussed herein. The example hub feature 1120 includes slanted or angled slots 1122 (or apertures) in a side wall 1124 of the hub feature 1120. The angled slots 1122 pass from an outside surface of the side wall 1124 to an inside surface of the side wall 1124, and pass through the side wall at an angle such that the slot is not orthogonal with the side wall 1124. In some examples, the slots 1122 may pass through the side wall 1124 at an angle of about 45 degrees with respect to the side wall 1124, or at another appropriate angle (e.g. about 30, 35, 40, 50, 55, 60, 65, 70, or 75 degrees). As will be described more fully below, the angled slots 1122 are used to locate wires of the frame in a particular orientation with respect to the hub feature 1120. Hub feature 1120 is sized for a six-wire device, but in other examples could be sized for devices having more (e.g., seven, eight, nine, ten, eleven, twelve, or more) or fewer (e.g., five, four, three, two) wires.

Figure 11D:
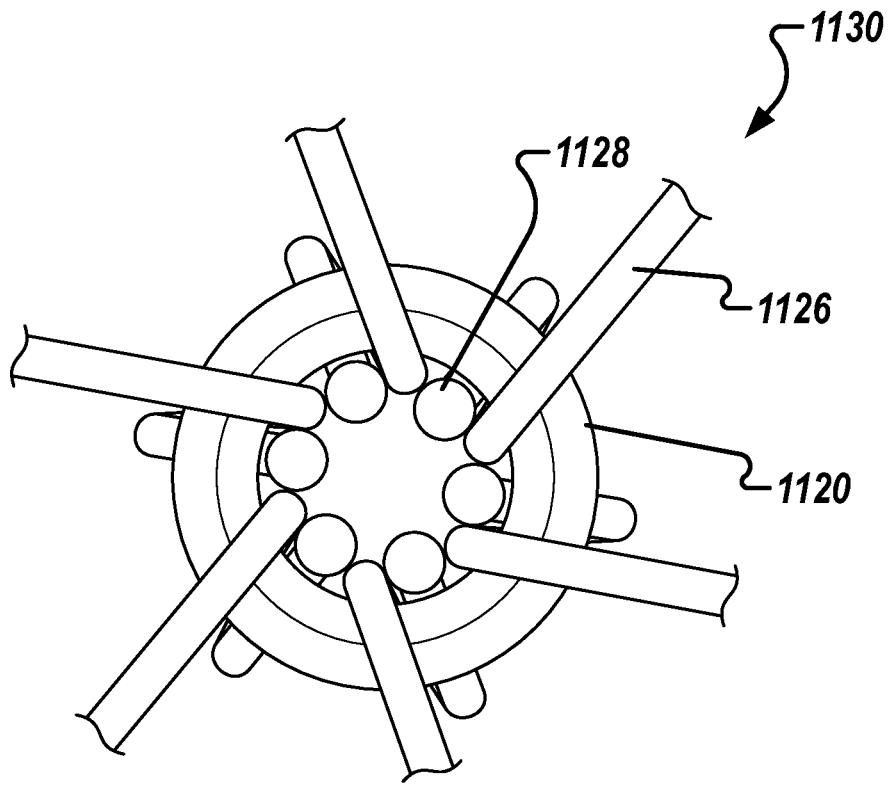
FIGS. 11D and 11E are views of a portion of an example frame that includes the example hub feature of FIG. 11C.
Figure 11E:
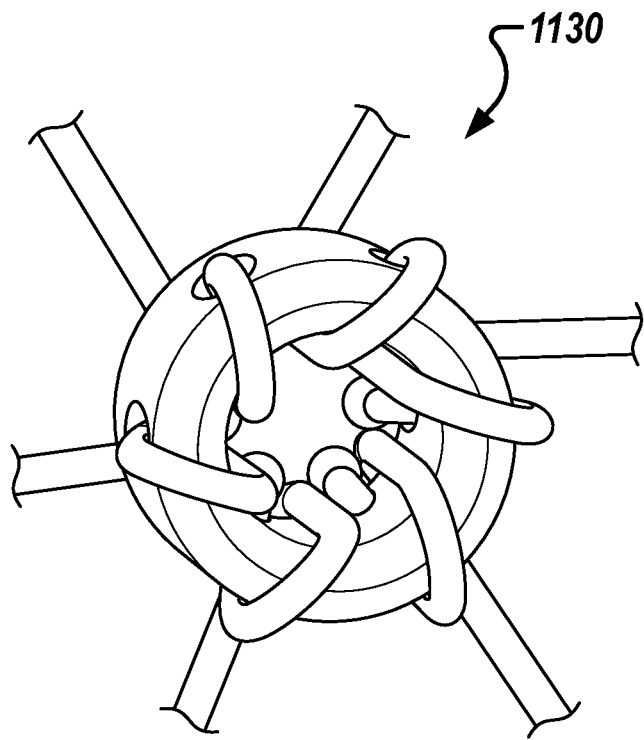

FIGS. 11D and 11E are views of a portion of an example frame 1130 that includes the example hub feature 1120 of FIG. 11C. As can be seen in FIG. 11D, wires 1126 of the frame 1130 are respectively passed through an angled slot 1122 from the space interior of the hub feature 1120 to the exterior of the hub feature 1120, and are then wrapped around the side wall 1124 and around the opposite longitudinal end of the side wall 1124. In the depicted example, the wire 1126 has a ball end 1128 that may be formed on the end of the wire 1126 by a welding process or other heating process, or may be attached to the end of the wire. The ball end 1128 can be sized larger than the angled slot 1122 to prevent the end of the wire 1126 from pulling through the angled slot 1122, and to couple the wire 1126 to the hub feature 1120.

Figure 11F:
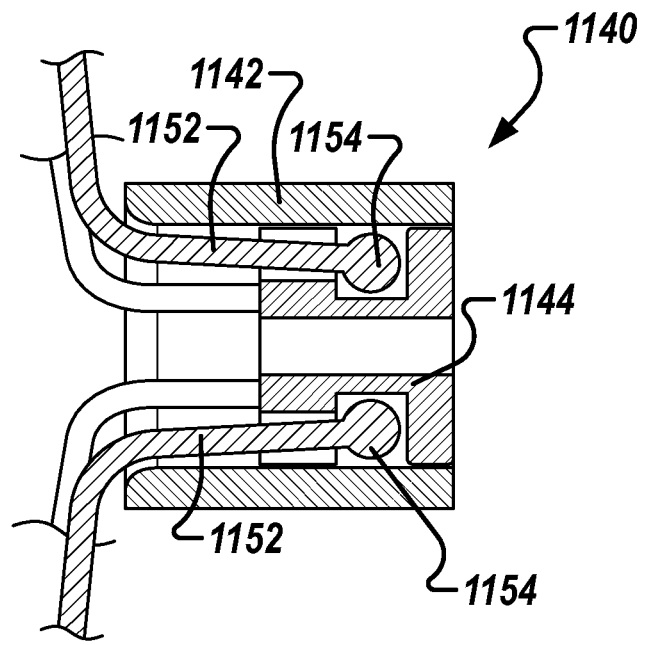
FIG. 11F is a cutaway view of another example hub feature.
Figure 11G:
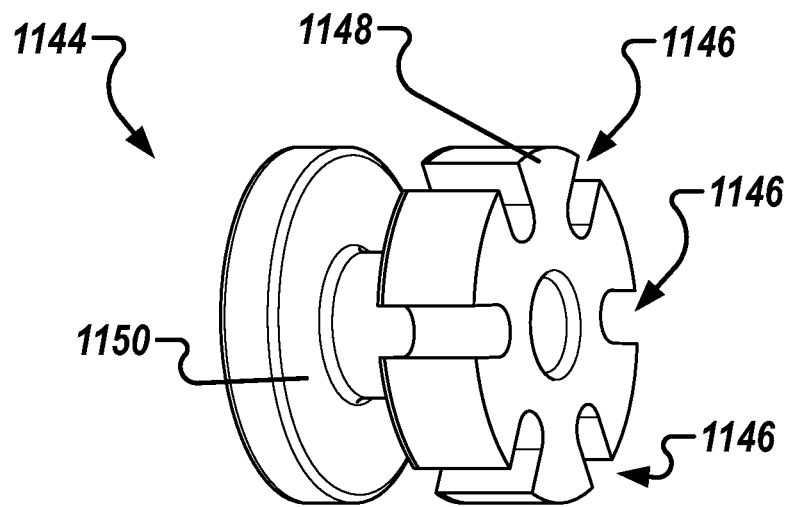
FIG. 11G is a perspective view of an inner component of the hub feature of FIG. 11F.

FIG. 11F is a cutaway view of another example hub feature 1140. In general, hub feature 1140 can replace an eyelet (e.g., a distal eyelet or a proximal eyelet) in any of the example devices discussed herein. Hub feature 1140 includes an outer component 1142 and an inner component 1144 that is disposed within, and attached to, the outer component 1142. FIG. 11G is a perspective view of the inner component 1144. In this example, inner component 1144 includes slots 1146 in a retaining member 1148 of the inner component 1144. A base member 1150 is disposed at an end of the inner component 1144.

Figure 11H:
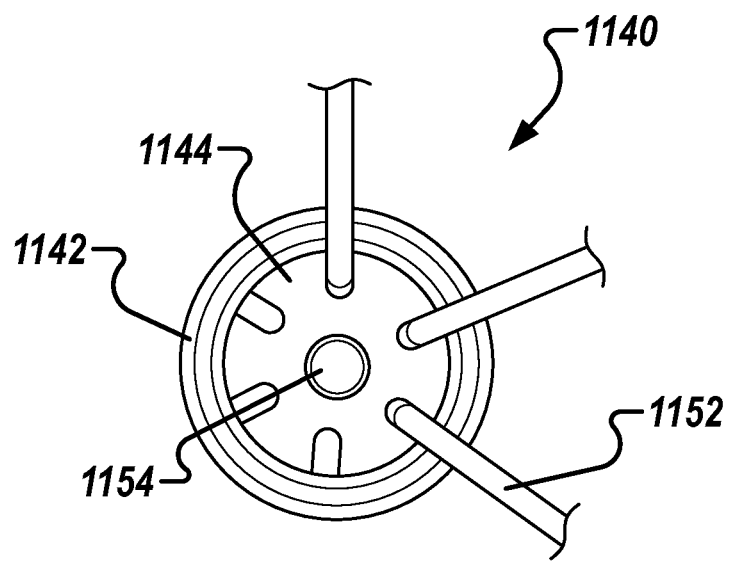
FIG. 11H is an end view of the hub feature of FIG. 11F.

As can be seen in FIG. 11F a ball end 1154 of a wire 1152 is disposed between the base member 1150 and the retaining member 1148 of the inner component 1144, and the wire 1152 passes through a slot 1146 of the inner component 1144. The wire 1152 then passes from an interior region of the outer component 1142 and over the side wall of the outer component 1142. FIG. 11H is an end view of the hub feature 1140 (only three of six frame wires 1152 are shown for simplicity). In the depicted example, inner component 1144 disposed within outer component 1142 so that the retaining member 1148 is a distance from an edge of the outer component 1142, so that wires 1152 are provided some strain relief before exiting the interior of the outer component 1142. In other embodiments, the retaining member 1148 may be flush with an edge of the outer component 1142. Inner component 1144 may define an attachment feature 1154 that may be used to releasably couple with a component of a delivery system, for example. The examples of FIGS. 11F-11H show a hub feature 1140 for a six-wire device, but alternative hub features may be sized for devices having more (e.g., seven, eight, nine, ten, eleven, twelve, or more) or fewer (e.g., five, four, three, two) wires.

Figure 11I:
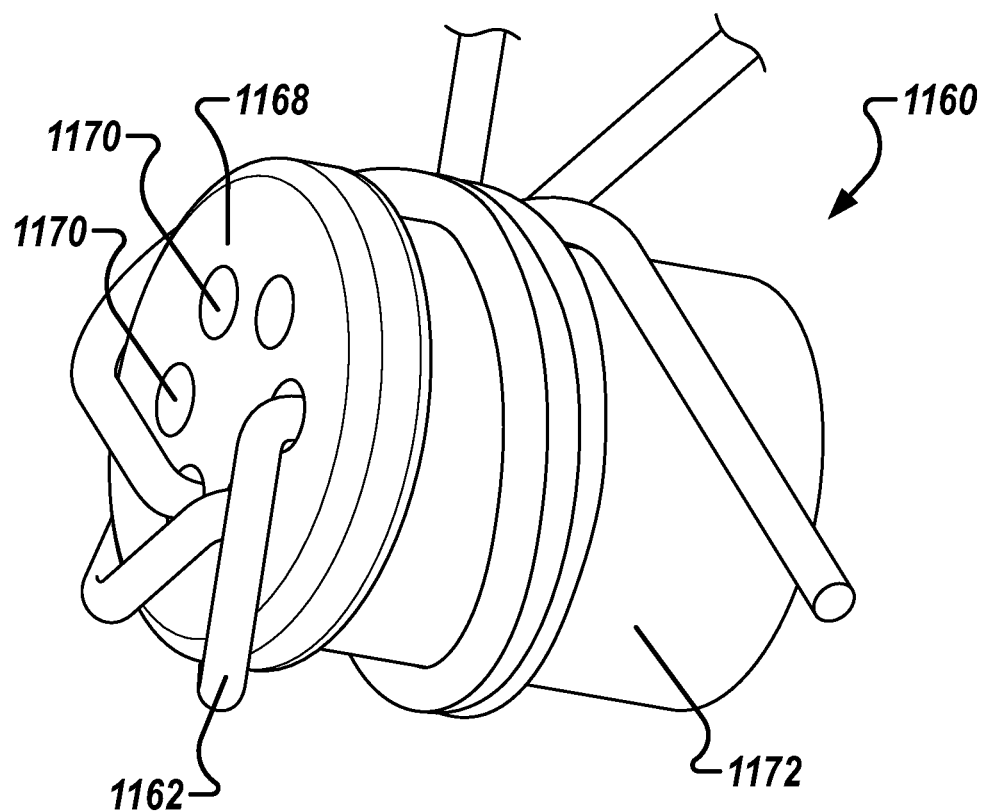
FIGS. 11I and 11J are perspective and cutaway views, respectively, of another example hub feature.
Figure 11J:
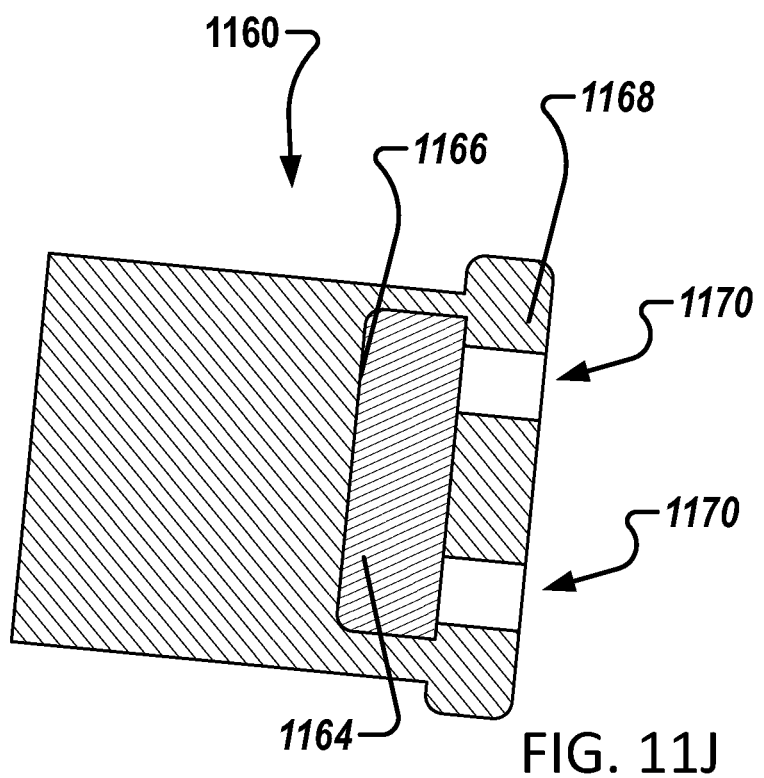
Figure 11K:
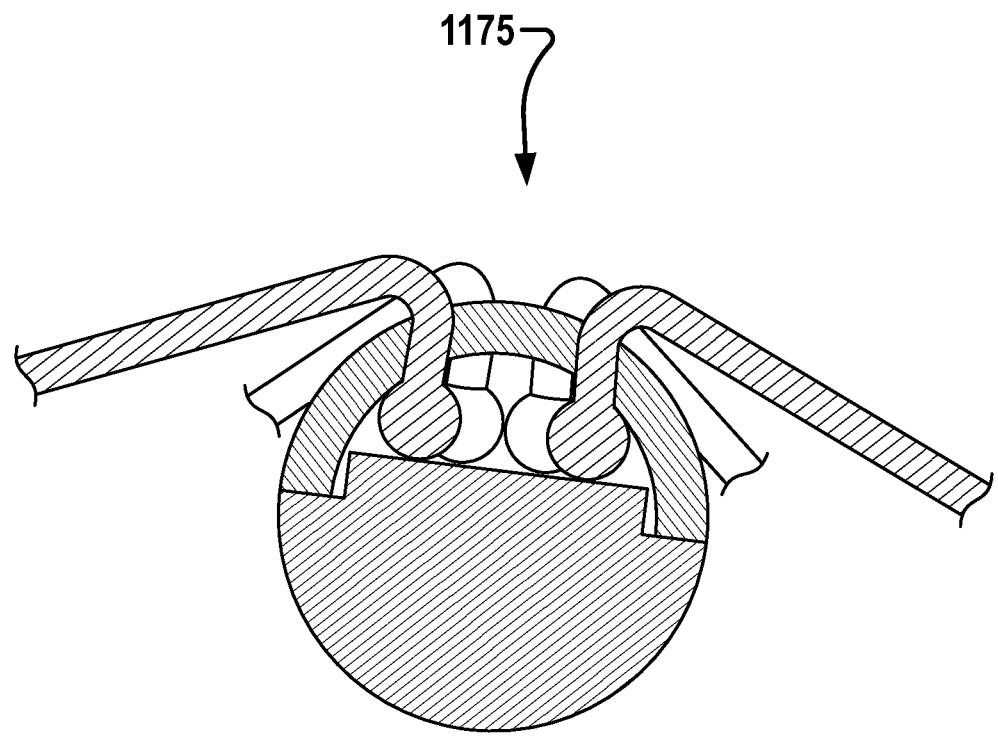
FIG. 11K is a cutaway view of another example hub feature.

FIGS. 11I and 11J are views of another example hub feature 1160. Hub feature 1160 is similar to hub feature 1140 in that ball ends of wires 1162 are contained within a region 1164 defined by a body 1172 of the hub feature. In particular, ball ends of wires 1162 are contained between a stopping surface 1166 of the hub feature 1160 and a cap 1168 of the hub feature, where the cap 1168 defines apertures 1170 through which the wires 1162 pass. The cap 1168 may be welded or otherwise attached to the body 1172 of the hub feature 1160. The wires 1162 are then wrapped around the body 1172 of the hub feature 1160 one or more times. Strain relief may be provided by wrapping the wires 1162 around the body 1172 of the hub feature, in some implementations. In some examples, the body 1172 of the hub feature may include grooves or channels in the exterior surface of the body 1172 to guide the wires 1162, for example. The example of FIG. 11I show a hub feature 1160 for a six-wire device, but alternative hub features may be sized for devices having more (e.g., seven, eight, nine, ten, eleven, twelve, or more) or fewer (e.g., five, four, three, two) wires. FIG. 11K is a cutaway view of another example hub feature 1175 that is similar to hub features 1140 and 1160, but where wires with ball ends are trapped within a ball-shaped hub feature.

Figure 11L:
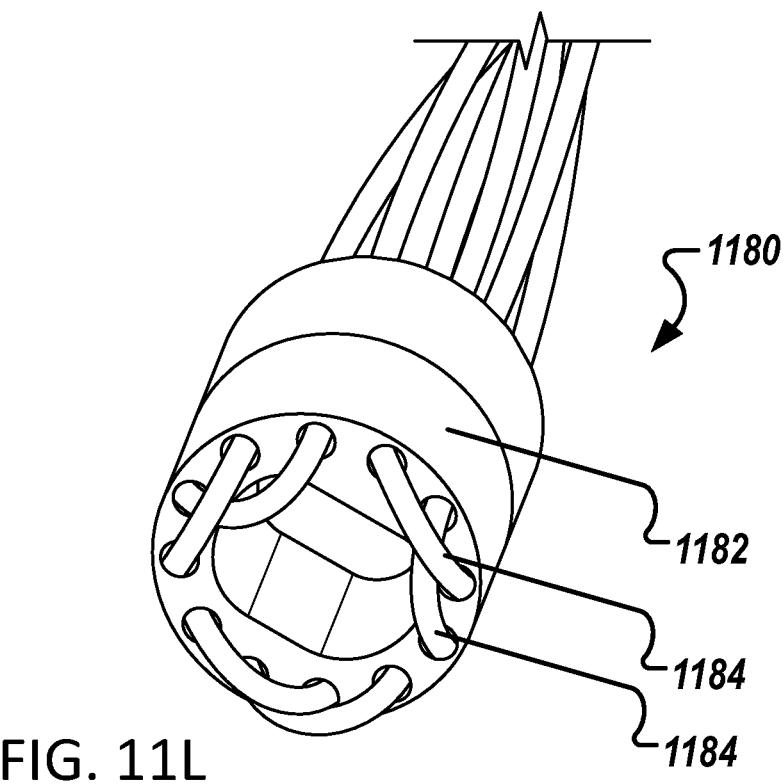
FIG. 11L is a perspective view of another example hub feature.

FIG. 11L is a perspective view of another example hub feature 1180. In the depicted example, hub feature 1180 includes a generally ring-shaped body portion 1182, which includes twelve apertures 1184 that are disposed longitudinally through a wall of the ring-shaped body portion 1182. In some examples, hub feature 1180 can be used with two-filar devices that include six wires, and in some examples the hub feature 1180 can be used with single-filar devices that include twelve wires.

The apertures 1184 may be laser-cut through the wall of the body portion 1180, in some examples. In some examples, some of the apertures 1180 may have a first diameter, and some of the apertures 1180 may have a second, different, diameter. In some examples, the apertures 1180 all have the same diameter. In general, the apertures 1180 may be equidistantly spaced around the circumference of the body member 1182.

FIG. 11L shows that six wires are used with hub feature 1180, where each of the six wires respectively passes through a first aperture 1184 of the hub feature 1180 in a first longitudinal direction, and then passes back through the hub feature 1180 in the opposite longitudinal direction via a second aperture 1184, where the second aperture 1184 is not adjacent to the first aperture 1184, but rather is offset by one aperture from the first aperture. For example, if the twelve apertures are consecutively numbered 1-12 in a clockwise direction around the body portion 1182, a first wire passes (in different directions) through apertures 1 and 3; a second wire passes (in different directions) through apertures 2 and 4; a third wire passes (in different directions) through apertures 5 and 7; a fourth wire passes (in different directions) through apertures 6 and 8; a fifth wire passes (in different directions) through apertures 9 and 11; and a sixth wire passes (in different directions) through apertures 10 and 12. In some examples some of the wires may have different sizes. For example, the first, third, and fifth wires may have a first diameter (e.g., 0.009"), and the second, fourth, and sixth wires may have a second diameter (e.g., 0.007"). This may allow, for examples certain features of the device to be formed by wires of the first diameter and other features of the device to be formed by wires of the second diameter. In some examples, the structural features of a device may be created with the larger wire and, for example, anchor features of the device may be created with the smaller wire.

Figure 11M:
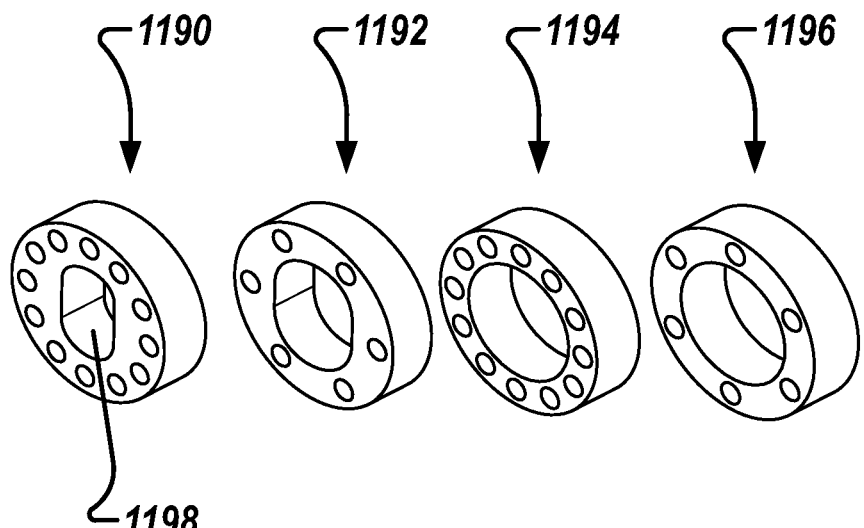
FIG. 11M is a view of various example hub components.

FIG. 11M is a view of various example hub components 1190, 1192, 1194, and 1196. Each of the hub components 1190-1196 has a generally ring-shaped body and defines apertures longitudinally though a wall of the ring-shaped body. Components 1190 and 1192 include a center lumen having a non-circular shape, and components 1194 and 1196 include a center aperture having a circular shape. Components 1190 and 1192 may be considered "keyed" components because of the non-circular shape of the center lumen, for example. The central lumen can be used for device deployment, device maneuverability, and maintaining device alignment during deployment, for example, as by coupling with a component of a delivery system.

Figure 11N:
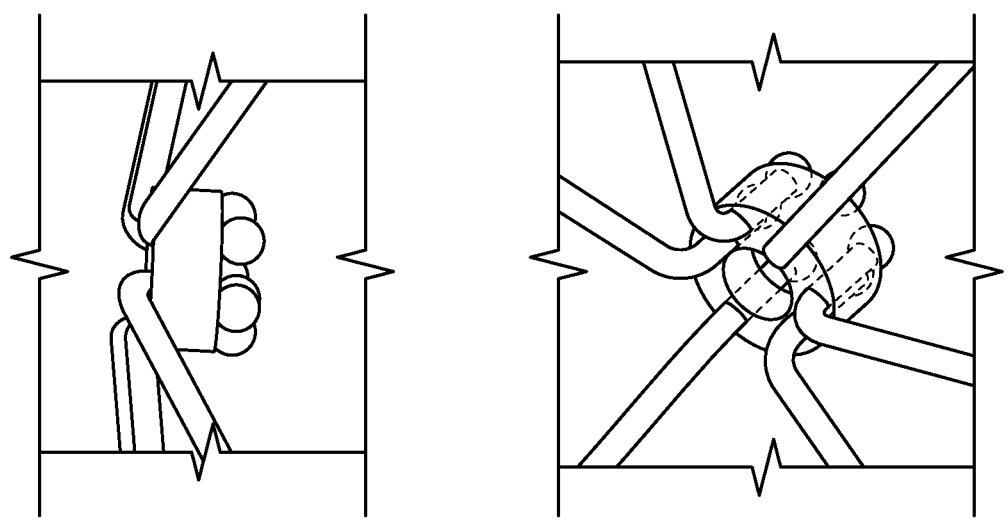
FIG. 11N is a view of various example applications for the hub components of FIG. 11L.

In various examples, the components 1190-1196 can have different heights or longitudinal lengths, and in some cases two or more components may be stacked, one on top of the other. In some examples, wires having a ball end may couple with a component of FIG. 11M (or of FIG. 11L), where the wire passes through an aperture of the component and the ball end prevents the end of the wire from passing through the aperture. FIG. 11N shows views of various applications of the components 1190-1196 of FIG. 11M (or FIG. 11L), and shows examples of how wires with ball ends can be terminated by the components. The balls can be formed by melting the wire ends or by other means of manipulating the wire ends.

Figure 12A:
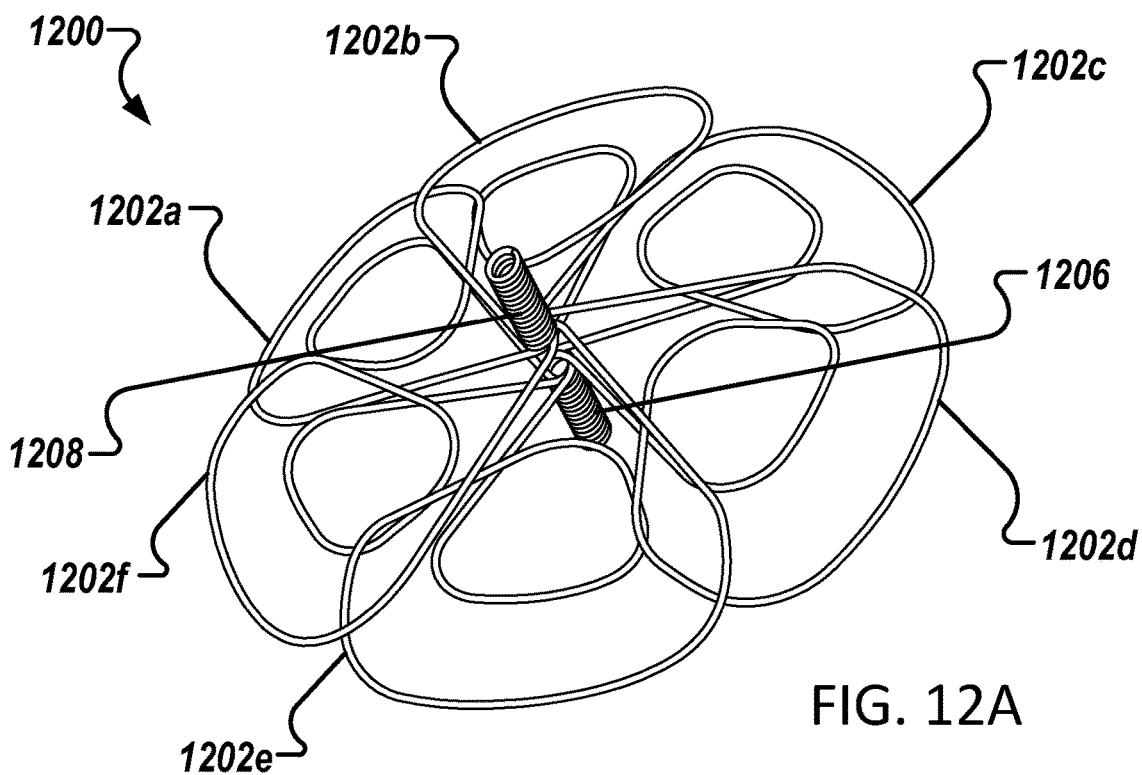
FIGS. 12A and 12B are perspective and proximal-end views, respectively, of an example occlusion device frame.
Figure 12B:
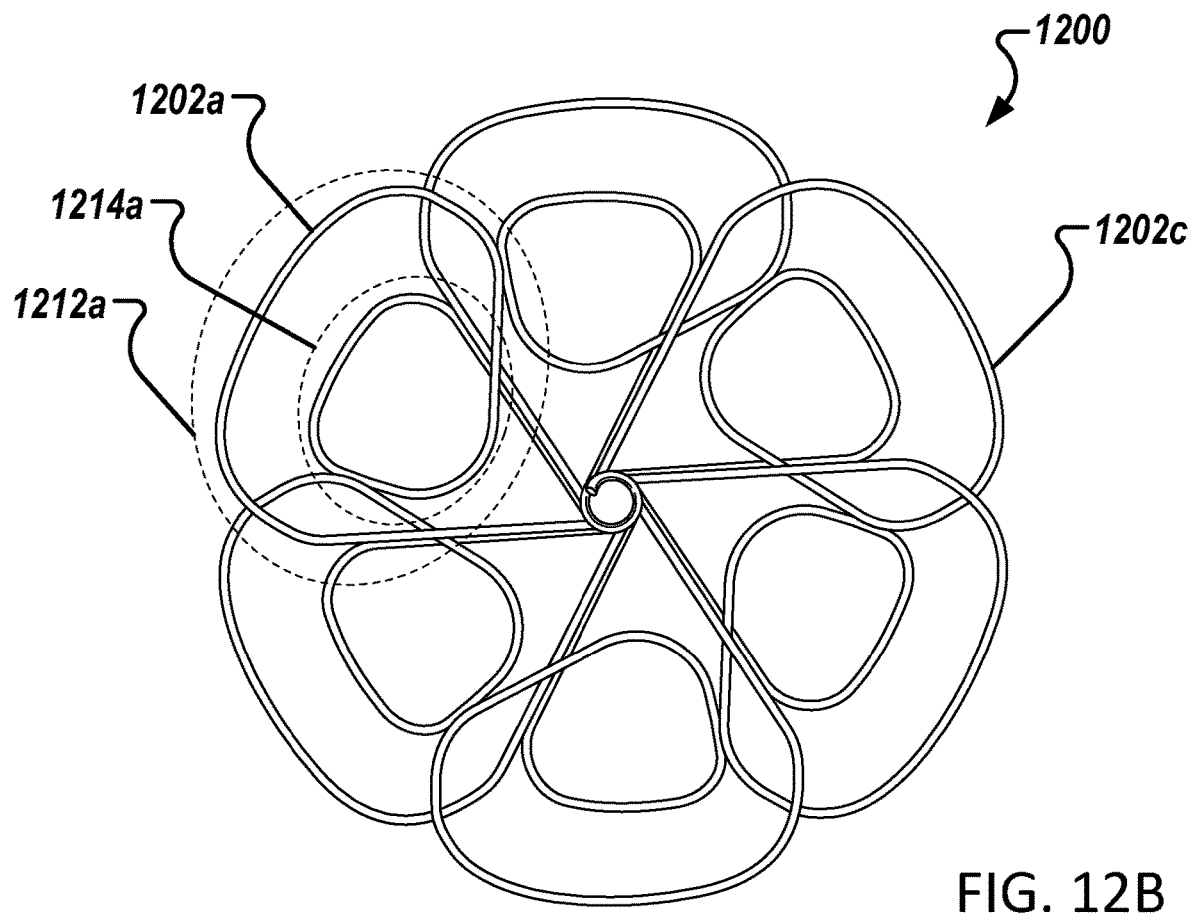

FIGS. 12A and 12B are perspective and proximal-end views, respectively, of an example occlusion device frame 1200. The frame 1200 includes six elongate members 1202, labeled 1202a, 1202b, 1202c, 1202d, 1202e and 1202f. A first end portion of each of the six elongate members 1202a-1202f forms the proximal eyelet 1208, and a second end portion of each of the elongate members 1202a-1202f forms the distal eyelet 1206. Between the eyelets 1208 and 1206, in this example, are the features of the proximal region and the distal region. With reference to elongate member 1202a, the elongate member 1202a extends from the proximal eyelet 1208 and forms a proximal feature 1212a. The proximal feature 1212a may generally be referred to as a "petal" of the device, and may generally be located in a proximal region of the device. After passing through a transition region of the device, the elongate member 1202a forms a distal feature 1214a, which may be generally located in a distal region of the device. As can be seen with reference to the proximal-end view of FIG. 12B, for a given elongate member 1202a, the distal feature 1214a formed by the elongate member 1202a is longitudinally aligned with the proximal feature 1212a formed by the same elongate member 1202a. As can also be seen with reference to FIG. 12B, elongate member exit features (e.g., exit location and exit angle) from the proximal eyelet and entry features (e.g., entry location and entry angle) at the distal eyelet may be considered. For example, elongate member 1202c exits the proximal eyelet at about the 12 o'clock position at an angle of about 30 degrees from vertical, and enters the distal eyelet at about the 12 o'clock position at an angle of about 90 degrees from vertical. By aligning the angle elongate member of exit from the proximal eyelet with the angle of entry into the distal eyelet within plus or minus about 90 degrees, the frame of the device may achieve a more torsionally balanced state, for example. In some cases, when the device is loaded into a collapsed or elongated or constrained configuration and then deployed and allowed to expand to an expanded configuration, there may be less torque tendency for one eyelet with respect to the other.

Similarly, each of the elongate members 1202b-1202f extends from the proximal eyelet 1208 and forms a respective proximal feature in the proximal region of the device, passes through the transition region of the device, and forms a respective distal feature in the distal region of the device. As can be seen with reference to FIG. 12B, the six proximal features or petals are generally spaced equidistantly around the proximal eyelet 1208, and in aggregate the six proximal features form an occlusion feature of the frame 1200 (e.g., when the frame or a portion of the frame is covered by a membranous covering). When the proximal features of the frame are covered by a membranous covering, for example, the occlusion feature may be used to occlude an LAA, or other space, hole, defect, aperture, appendage, vessel or conduit within a body of a patient. Similarly, the six distal features are generally spaced equidistantly around the distal eyelet 1206, and in aggregate the six distal features form a support feature of the frame 1200. In some examples, one or more of the distal features 1214 (or proximal features 1212) may include a micro-coil anchor, or may include an integrated anchor feature (see discussion of FIGS. 14C and 14D below).

Figure 13A:
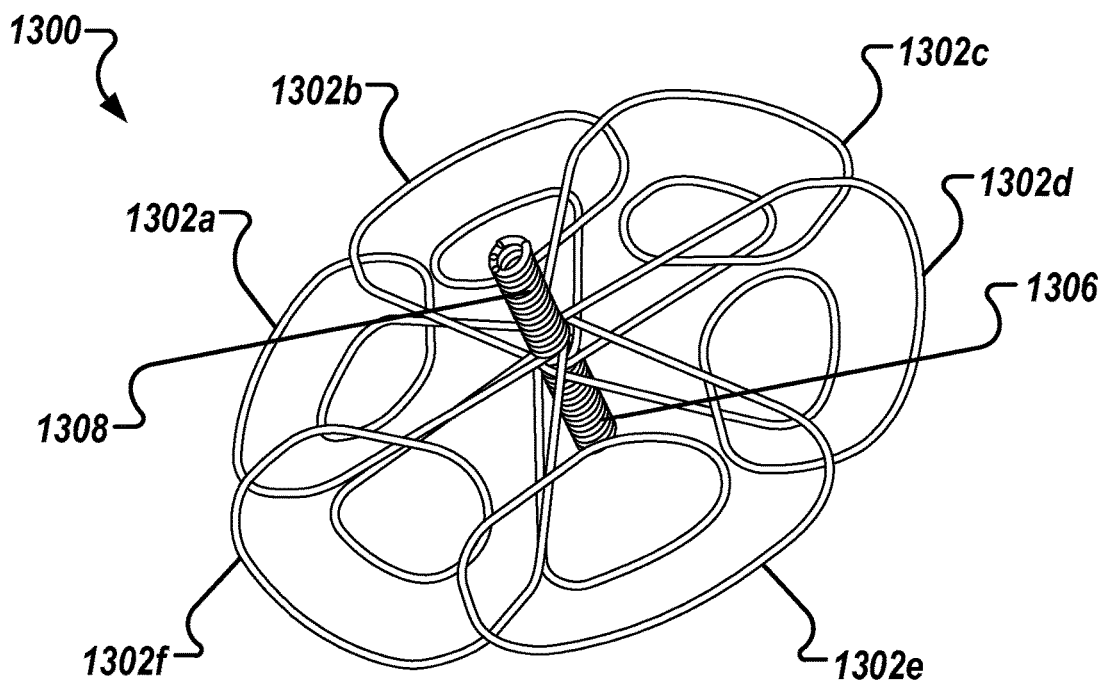
FIGS. 13A and 13B are perspective and proximal-end views, respectively, of another example occlusion device frame.
Figure 13B:
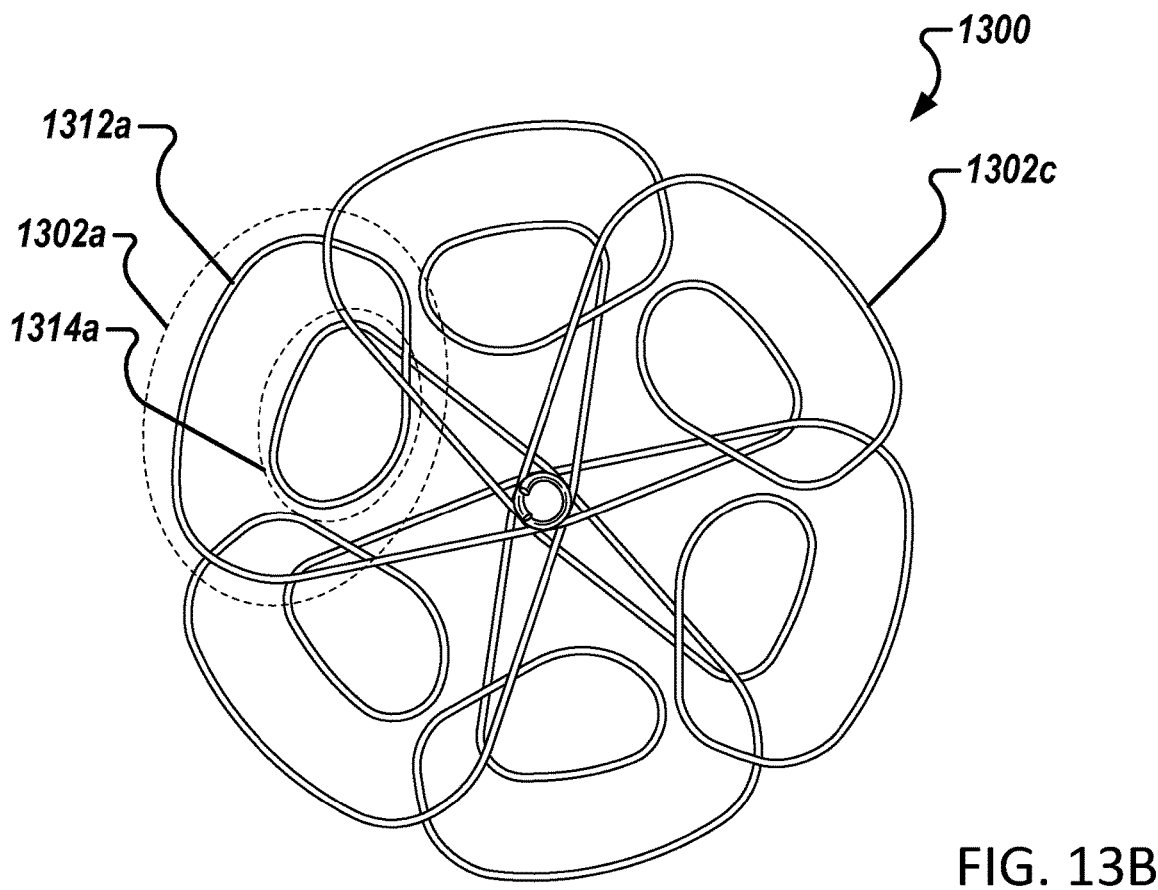

FIGS. 13A and 13B are perspective and proximal-end views, respectively, of an example occlusion device frame 1300. The frame 1300 includes six elongate members 1302, labeled 1302a, 1302b, 1302c, 1302d, 1302e and 1302f. A first end portion of each of the six elongate members 1302a-1302f forms the proximal eyelet 1308, and a second end portion of each of the elongate members 1302a-1302f forms the distal eyelet 1306. Between the eyelets 1308 and 1306, in this example, are the features of the proximal region and the distal region. With reference to elongate member 1302a, the elongate member 1302a extends from the proximal eyelet 1308 and forms a proximal feature 1312a. The proximal feature 1312a may generally be referred to as a "petal" of the device, and may generally be located in a proximal region of the device. After passing through a transition region of the device, the elongate member 1302a forms a distal feature 1314a, which may be generally located in a distal region of the device. As can also be seen with reference to FIG. 13B, elongate member 1302c exits the proximal eyelet at about the 12 o'clock position at an angle of about 20 degrees from vertical, and enters the distal eyelet at about the 4 o'clock position at an angle of about 60 degrees from vertical.

Similarly, each of the elongate members 1302b-1302f extends from the proximal eyelet 1308 and forms a respective proximal feature in the proximal region of the device, passes through the transition region of the device, and forms a respective distal feature in the distal region of the device. As can be seen with reference to FIG. 13B, the six proximal features or petals are generally spaced equidistantly around the proximal eyelet 1308, and in aggregate the six proximal features form an occlusion feature of the frame 1300 (e.g., when the frame or a portion of the frame is covered by a membranous covering). When the proximal features of the frame are covered by a membranous covering, for example, the occlusion feature may be used to occlude an LAA, or other space, hole, defect, aperture, appendage, vessel or conduit within a body of a patient. Similarly, the six distal features are generally spaced equidistantly around the distal eyelet 1306, and in aggregate the six distal features form a support feature of the frame 1300.

As compared to the frame 1200 shown in FIGS. 12A and 12B, the frame 1300 of FIGS. 13A and 13B has distal features 1314 that are generally "egg-shaped," while frame 1200 has distal features 1214 that are generally more cone-shaped. Frame 1300 includes a shallower transition or waist region (the region where the elongate members transition from the proximal feature to the distal feature) than frame 1200, which has a deeper transition or waist region. With a deeper transition region, the elongate members 1202 through the transition region may be closer to a longitudinal axis of the frame 1200 defined by the eyelets 1206 and 1208. By contrast, the elongate members 1302 through the transition region are farther away from the longitudinal axis of the frame 1300 defined by the eyelets 1306 and 1308. The deeper transition or waist region of frame 1200 can be formed, for example, by wrapping the wind closer to the center of the jig when transitioning between distal and proximal discs, for example. In some examples, one or more of the distal features 1314 (or proximal features 1312) may include a micro-coil anchor, or may include an integrated anchor feature (see discussion of FIGS. 14C and 14D below).

Figure 14A:
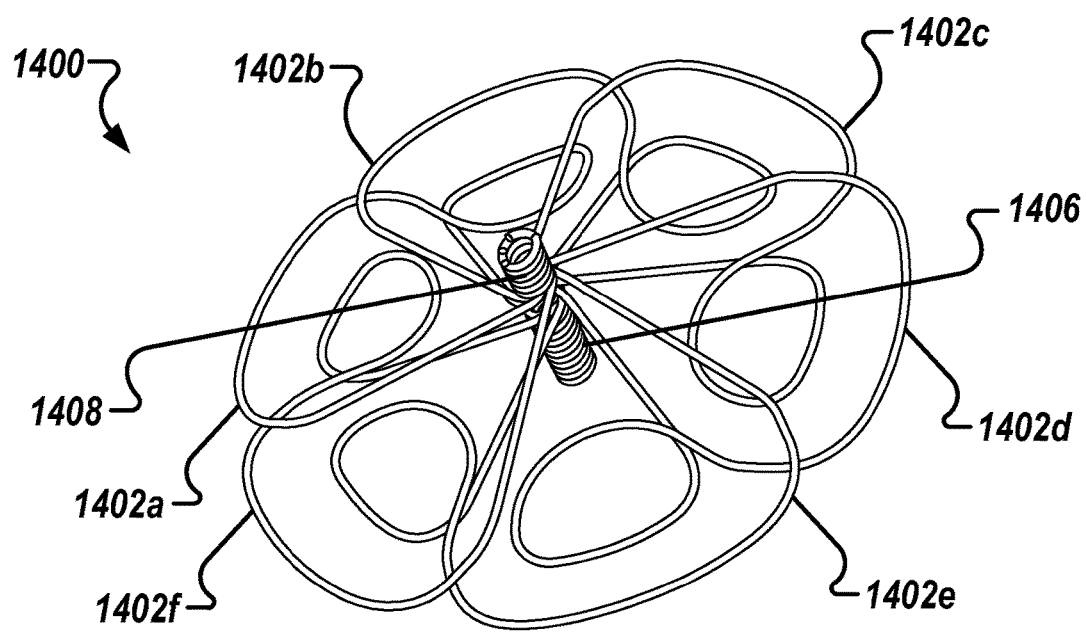
FIGS. 14A and 14B are perspective and proximal-end views, respectively, of another example occlusion device frame.
Figure 14B:
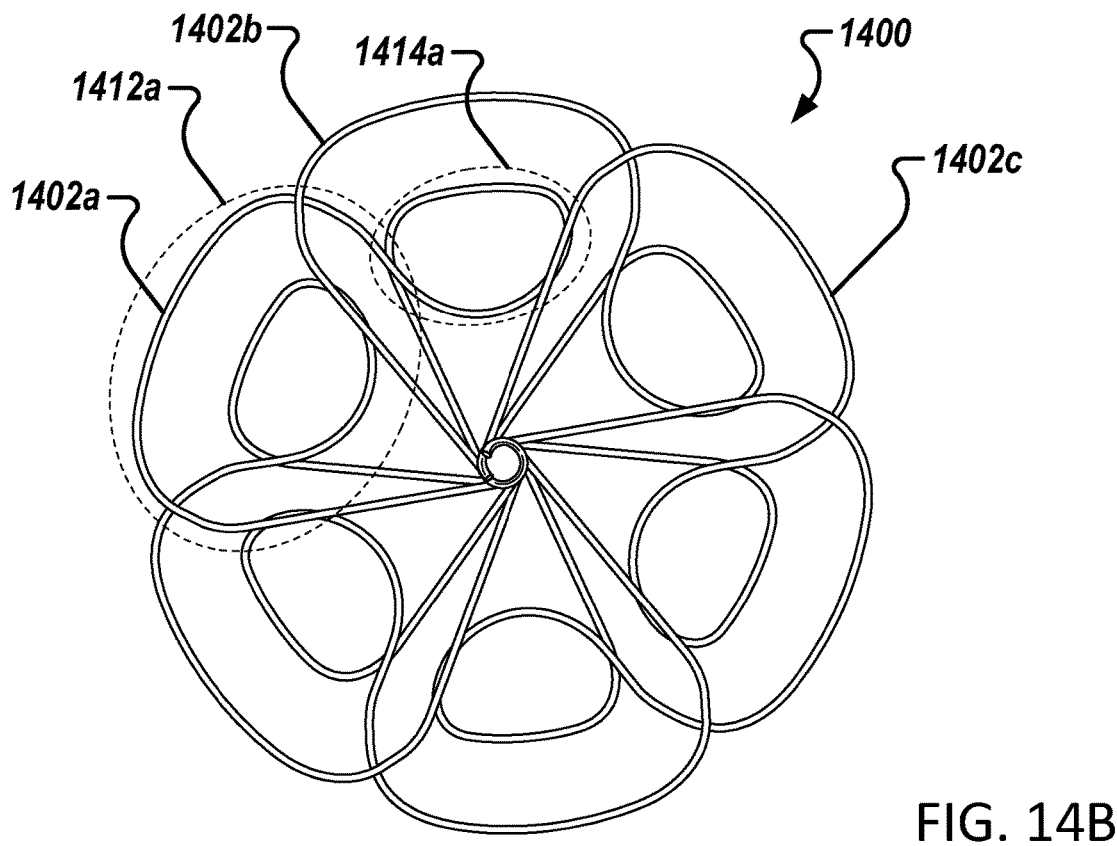

FIGS. 14A and 14B are perspective and proximal-end views, respectively, of an example occlusion device frame 1400. The frame 1400 includes six elongate members 1402, labeled 1402*a*, 1402*b*, 1402*c*, 1402*d*, 1402*e* and 1402*f*. A first end portion of each of the six elongate members 1402*a*-1402*f* forms the proximal eyelet 1408, and a second end portion of each of the elongate members 1402*a*-1402*f* forms the distal eyelet 1406. Between the eyelets 1408 and 1406, in this example, are the features of the proximal region and the distal region. With reference to elongate member 1402*a*, the elongate member 1402*a* extends from the proximal eyelet 1408 and forms a proximal feature 1412*a*. The proximal feature 1412*a* may generally be referred to as a "petal" of the device, and may generally be located in a proximal region of the device. After passing through a transition region of the device, the elongate member 1402*a* forms a distal feature 1414*a*, which may be generally located in a distal region of the device. As can be seen with reference to the proximal-end view of FIG. 14B, for a given elongate member 1402*a*, the distal feature 1414*a* formed by the elongate member 1402*a* is formed generally offset in a clockwise direction from the proximal feature 1412*a* formed by the same elongate member 1402*a*. For example, the distal feature 1414*a* is generally longitudinally aligned with the proximal feature formed by the adjacent elongate member in the clockwise direction (elongate member 1402*b* in this example) when viewed from the proximal end of the device. As can also be seen with reference to FIG. 14B, elongate member 1402*c* exits the proximal eyelet at about the 12 o'clock position at an angle of about 20 degrees from vertical, and enters the distal eyelet at about the 12 o'clock position at an angle of about 75 degrees from vertical.

As can further be seen with reference to FIG. 14B, as a given elongate member 1402 passes through a transition region of the device, the elongate member 1402 reverses a wire winding direction. For example, proximal feature 1412*a* can be seen to be wound in a generally clockwise direction, while the distal feature 1414*a* formed by the same elongate member 1402*a* is wound in a generally counter-clockwise direction. The same is true for the other elongate members 1402*b*-1402*f*. As such, frame 1400 may be considered a balanced frame, as reversing the wind direction may balance or remove an amount of torsional bias with the elongate member. For example, by reversing the winding direction between the proximal and distal features, some of the torque associated with the wound wires may beneficially be canceled.

Similarly, each of the elongate members 1402*b*-1402*f* extends from the proximal eyelet 1408 and forms a respective proximal feature in the proximal region of the device, passes through the transition region of the device, and forms a respective distal feature in the distal region of the device. As can be seen with reference to FIG. 14B, the six proximal features or petals are generally spaced equidistantly around the proximal eyelet 1408, and in aggregate the six proximal features form an occlusion feature of the frame 1400 (e.g., when the frame or a portion of the frame is covered by a membranous covering). When the proximal features of the frame are covered by a membranous covering, for example, the occlusion feature may be used to occlude an LAA, or other space, hole, defect, aperture, appendage, vessel or conduit within a body of a patient. Similarly, the six distal features are generally spaced equidistantly around the distal eyelet 1406, and in aggregate the six distal features form a support feature of the frame 1400.

Figure 14C:
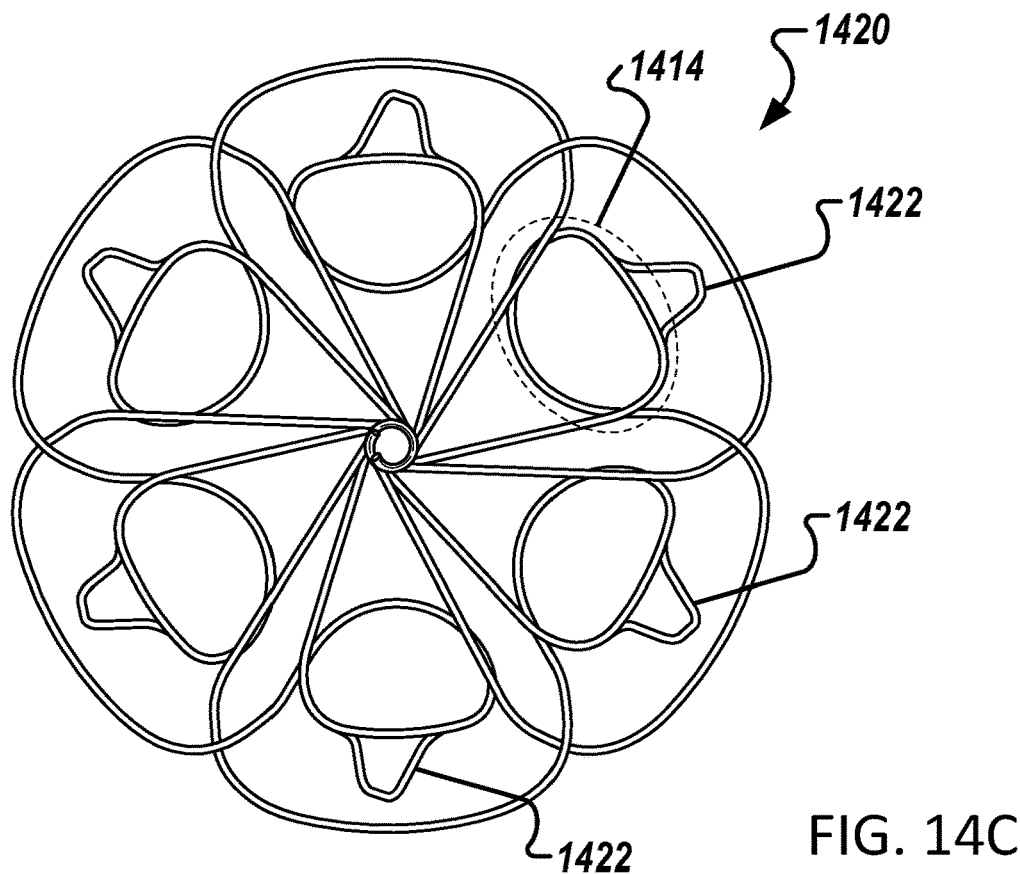
FIG. 14C is an end view of another example occlusion device frame.

FIG. 14C is an end view of another example occlusion device frame 1420. Frame 1420 is similar to frame 1400 of FIGS. 14A and 14B, and generally includes the same or similar proximal features 1412 and distal features 1414 that frame 1400 includes (except that the proximal and/or distal features 1412 and 1414, or portions thereof, can in some cases be formed by two wires rather than one), but additionally includes, for each distal feature 1414 of the frame 1420, an integrated anchor feature 1422. In this example, the integrated anchor feature 1422 includes a loop or fin adapted to atraumatically contact tissue and minimize or prevent migration of the frame 1420 at a deployment site. In some examples, one or more of the distal features 1414 (e.g., every other distal feature, or every third distal feature) does not include an integrated anchor feature 1422. While the integrated anchor features 1422 are shown at the distal features 1414 of the frame, in some alternative embodiments the integrated anchor features 1422 may be included with one or more proximal features 1412 of the frame, or with both proximal and distal features of the frame.

In various examples, frame 1420 (or a portion of frame 1420) may be a two-filar frame or portion of the frame. For example, each proximal feature 1412 may be formed by two wires running generally parallel with one another, and a portion of each distal feature 1414 may be formed by the two wires. A second of the two wires forms the integrated anchor feature 1422 and then returns to generally follow the path of the first wire of the two wires. In some examples, the second wire may terminate after forming the integrated anchor feature 1422. More particularly, in some examples twelve wire ends are used to form a distal eyelet, and the twelve wires are fanned out as six pairs of wires to form the (six) distal features 1414. A first wire of each pair forms the distal feature 1414, and a second wire of each pair forms the integrated anchor feature 1422. In some examples, the pairs are a twisted pair of wires along the wire path except where the integrated anchor feature 1422 is formed. In some examples, the second wire of each pair terminates after forming the integrated anchor feature 1422. In some examples, the second wire of each pair continues on the same path as the first wire of each pair and together they form the proximal feature 1412, and terminate at the proximal eyelet. In manufacturing the frame 1420, the winding jig may include an extra pin (or winding paths for some tools), for example, around which the second wire of the pair is wound to create the integrated anchor feature 1422.

Figure 14D:
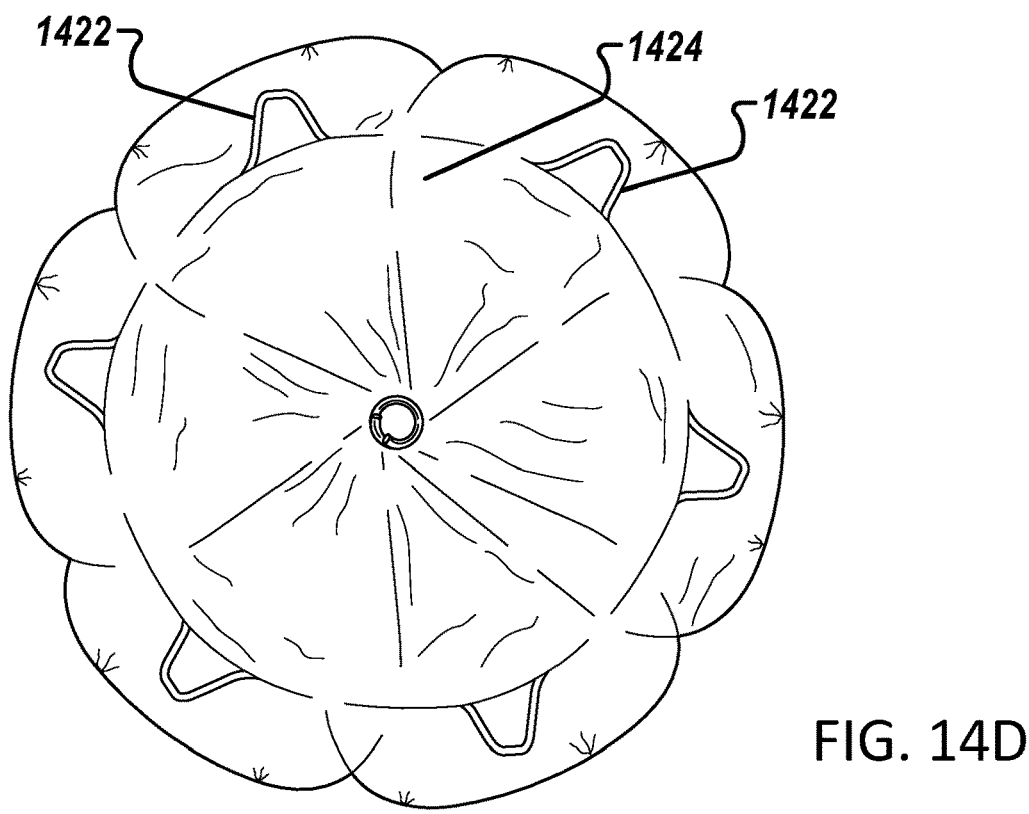
FIG. 14D is an end view of the occlusion device frame of FIG. 14C with a sealing member attached to the frame.

FIG. 14D is an end view of the occlusion device frame 1420 of FIG. 14C with a sealing member 1424 attached to the frame 1420. As can be seen in FIG. 14D, the sealing member 1424, which may correspond to any of the membranous coverings discussed herein, may be disposed over the frame 1420, but the integrated anchor features 1422 may protrude through the sealing member 1424 (e.g., through slits in the sealing member 1424).

Alternative integrated anchor features can be created using the same wire or elongate member that defines the frame of the device and defines proximal features and distal features, for example. FIGS. 21A, 21B, 21C, 21D, and 21E are views of other frames 2100a-e, respectively, that include integrated anchor features 2102a-e, respectively. For simplicity, only a single disc of the respective frames is shown for frames 2100a and 2011e of FIGS. 21A and 21E, respectively, but the integrated anchor features 2102a, 2102e may be located on either distal features or proximal features of a two-disc device, for example. The integrated anchor features 2102a-e are formed by the same elongate member that forms the proximal or distal feature of the frame in the examples of FIGS. 21A-E, in contrast to the two-filar design described above with reference to FIGS. 14C and 14D. Frames 2100a, 2100b, and 2100c include integrated anchor features 2102a, 2102b, and 2102c, respectively, that each include an open loop or finger portion adapted to atraumatically contact tissue and minimize of prevent migration of the corresponding frame at a deployment site. Frames 2100d and 2100e include integrated anchor features 2102d and 2102e, respectively, that each include a closed loop or finger portion adapted to atraumatically contact tissue and minimize of prevent migration of the corresponding frame at a deployment site. With the loop or finger portion of anchor 2102e, the wire crosses itself at a base of the loop, and a tether 2104 is tied around the wire crossing junction to hold the wire portions together at the junction. In some examples, the tether 2104 is comprised of ePTFE or PTFE. The anchor features shown in any of FIGS. 21A-E are may have varying angles, and may be oriented proximally or distally, in various embodiments. For example, various anchor features of a given device may have different angle orientations (i.e. one or more may be oriented proximally, and one or more may be oriented distally. Lengths of the anchor features may also be varied, in various embodiments. In manufacturing the frames 2100, the corresponding winding jig may include an extra pin (or winding paths for some tools), for example, around which the wire is wound to create the integrated anchor feature. In general, any of the frame designs discussed herein may include an integrated anchor feature similar to the features 2100a-e depicted in FIGS. 21A-E, respectively. Any of the frames shown in FIGS. 21A-E could also be constructed as a two-filar design, or as an n-filar design (where n=3, 4, or more, in some examples). Wires can vary by size, material, and cross sectional shape, as discussed herein above for other examples.

Figure 15:
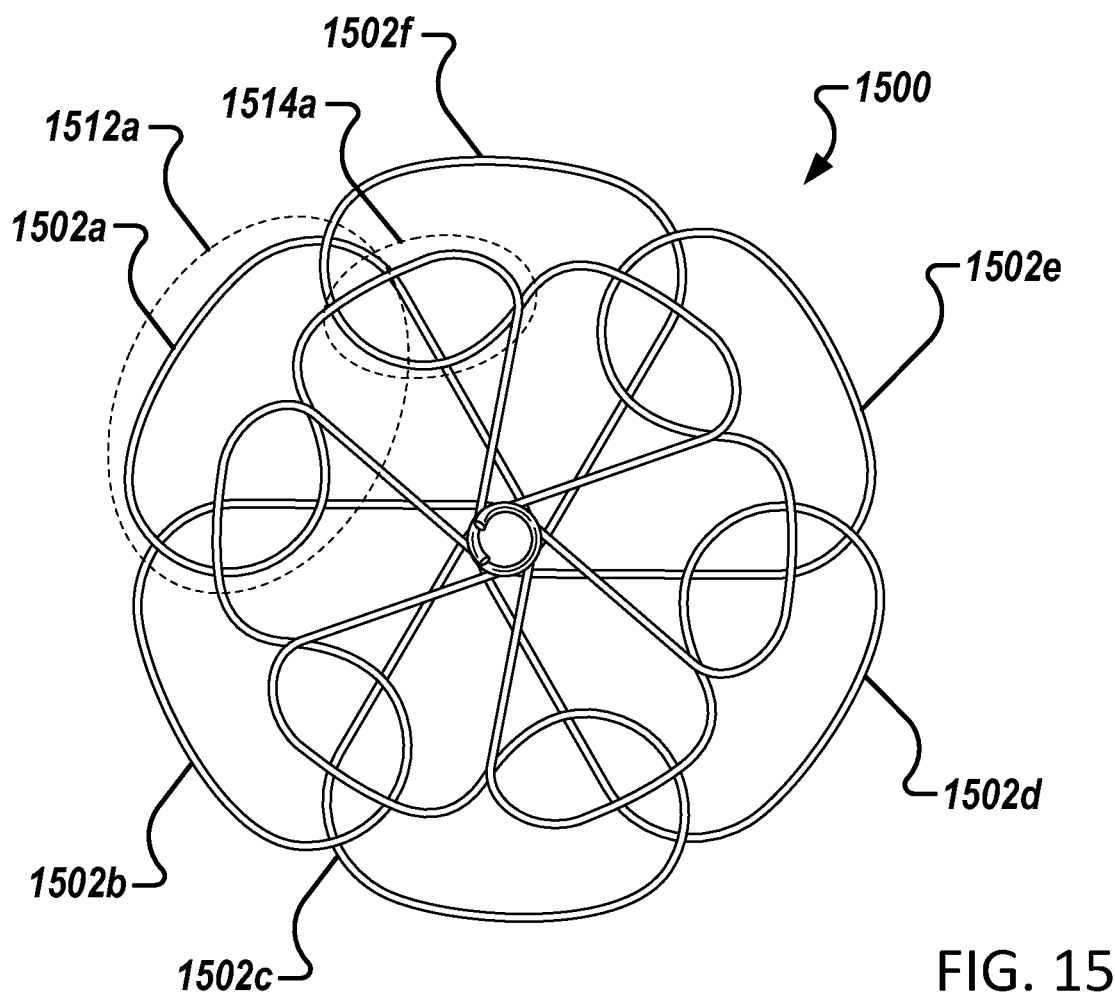
FIG. 15 is a distal-end view of another example occlusion device frame.

FIG. 15 is a distal-end view of an example occlusion device frame 1500. The frame 1500 includes six elongate members 1502, labeled 1502a, 1502b, 1502c, 1502d, 1502e and 1502f. A first end portion of each of the six elongate members 1502a-1502f forms the proximal eyelet (generally into the page in the view of FIG. 15), and a second end portion of each of the elongate members 1502a-1502f forms the distal eyelet (generally out of the page in the view of FIG. 15). Between the eyelets, in this example, are the features of the proximal region and the distal region. With reference to elongate member 1502a, the elongate member 1502a extends from the proximal eyelet and forms a proximal feature 1512a. The proximal feature 1512a may generally be referred to as a "petal" of the device, and may generally be located in a proximal region of the device. After passing through a transition region of the device, the elongate member 1502a forms a distal feature 1514a, which may be generally located in a distal region of the device. As can be seen with reference to the distal-end view of FIG. 15, for a given elongate member 1502a, the distal feature 1514a formed by the elongate member 1502a is formed generally offset in a clockwise direction from the proximal feature 1512a formed by the same elongate member 1502a. For example, the distal feature 1514a is generally partially longitudinally aligned with the proximal feature formed by the adjacent elongate member in the clockwise direction when viewed from the distal end of the device (elongate member 1502f in this example), and partially longitudinally aligned with the proximal feature 1512a formed by elongate member 1502a.

As can further be seen with reference to FIG. 15, as a given elongate member 1502 passes through a transition region of the device, the elongate member 1502 reverses a wire winding direction. For example, proximal feature 1512a can be seen to be wound in a generally counter-clockwise direction (when viewed from the distal end as in FIG. 15), while the distal feature 1514a formed by the same elongate member 1502a is wound in a generally clockwise direction. The same is true for the other elongate members 1502b-1502f. As such, frame 1500 may be considered a balanced frame, as reversing the wind direction may balance or remove an amount of torsional bias with the elongate member.

Similarly, each of the elongate members 1502b-1502f extends from the proximal eyelet and forms a respective proximal feature in the proximal region of the device, passes through the transition region of the device, and forms a respective distal feature in the distal region of the device. As can be seen with reference to FIG. 15, the six proximal features or petals are generally spaced equidistantly around the proximal eyelet, and in aggregate the six proximal features form an occlusion feature of the frame 1500 (e.g., when the frame or a portion of the frame is covered by a membranous covering). When the proximal features of the frame are covered by a membranous covering, for example, the occlusion feature may be used to occlude an LAA, or other space, hole, defect, aperture, appendage, vessel or conduit within a body of a patient. Similarly, the six distal features are generally spaced equidistantly around the distal eyelet, and in aggregate the six distal features form a support feature of the frame 1500. In some examples, one or more of the distal features 1514 (or proximal features 1512) may include a micro-coil anchor, or may include an integrated anchor feature (see discussion of FIGS. 14C and 14D above).

Figure 16A:
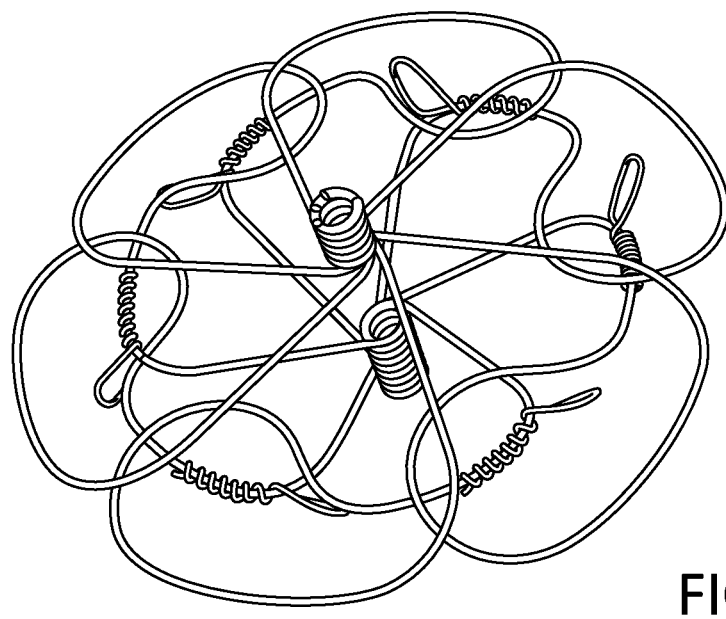
FIGS. 16A and 16B are perspective and proximal-end views, respectively, of another example occlusion device frame.
Figure 16B:
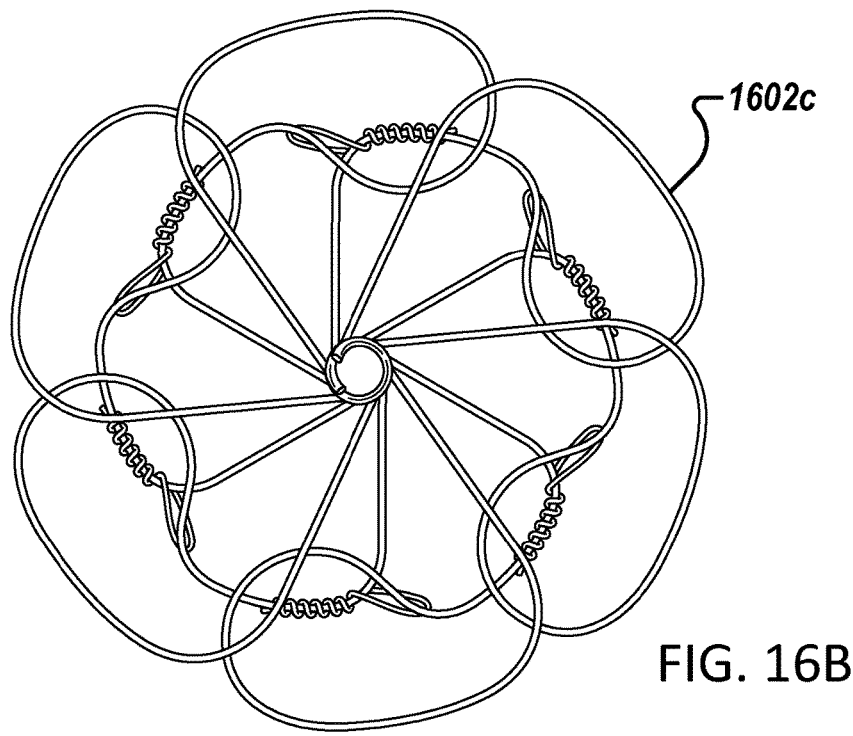

FIGS. 16A and 16B are perspective and end views, respectively, of another example occlusion device frame that includes fixation anchors on distal features of the device frame. The frames shown in FIGS. 16A and 16B correspond to the frame 1500 of FIG. 15, and also include micro-coil anchors on distal features of the frame. As can be seen with reference to FIG. 16B, elongate member 1602c exits the proximal eyelet at about the 11 o'clock position at an angle of about 20 degrees from vertical, and enters the distal eyelet at about the 11 o'clock position at an angle of about −10 degrees from vertical. In some examples, the fixation anchors on the distal features may be replaced by an integrated anchor feature (see discussion of FIGS. 14C and 14D above).

Figure 18:
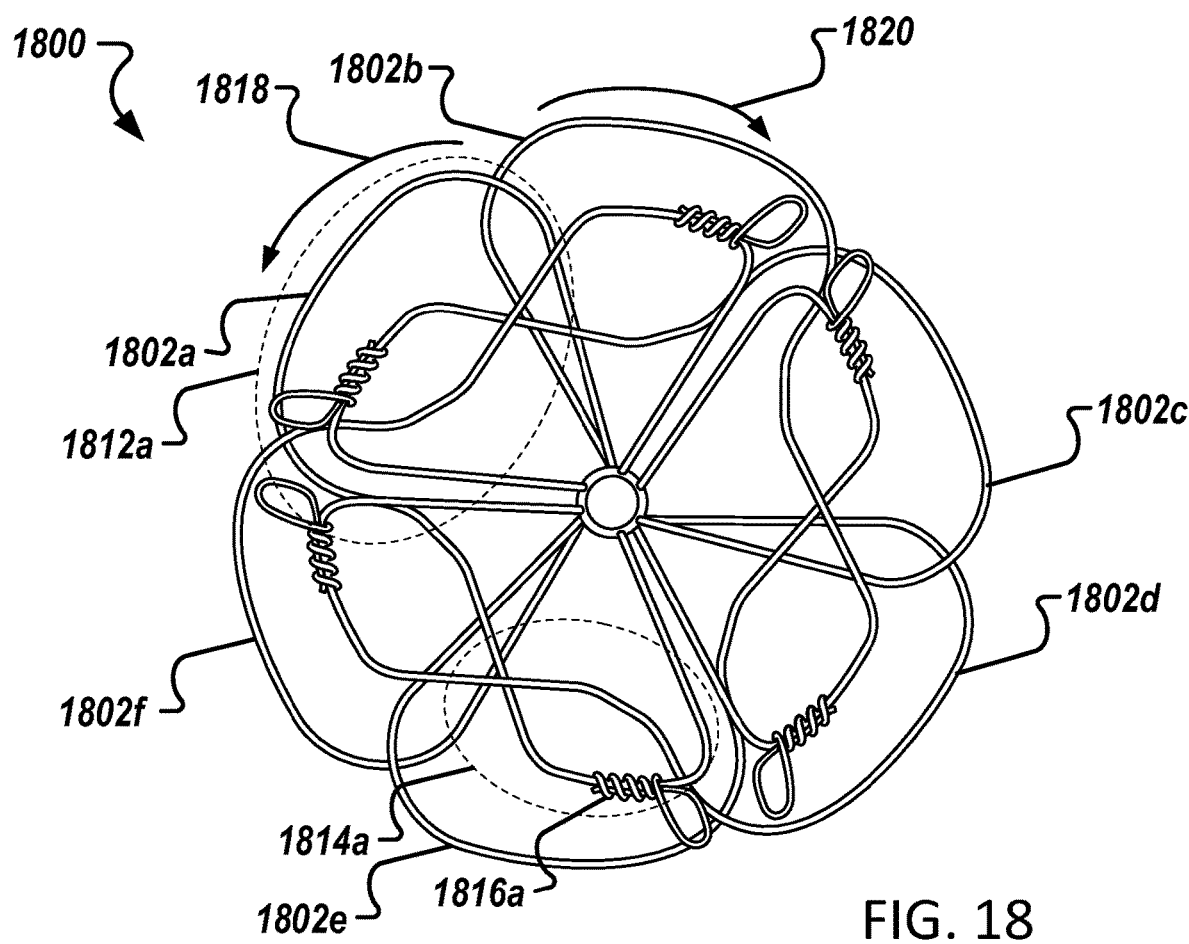
FIG. 18 is a distal-end view of an example occlusion device frame.

FIG. 18 is a distal-end view of an example occlusion device frame 1800. The frame 1800 includes six elongate members 1802, labeled 1802a, 1802b, 1802c, 1802d, 1802e and 1802f. A first end portion of each of the six elongate members 1802a-1802f forms the proximal eyelet (generally into the page in the view of FIG. 18), and a second end portion of each of the elongate members 1802a-1802f forms the distal eyelet (generally out of the page in the view of FIG. 18). Between the eyelets, in this example, are the features of the proximal region and the distal region. With reference to elongate member 1802a, the elongate member 1802a extends from the proximal eyelet and forms a proximal feature 1812a. The proximal feature 1812a may generally be referred to as a "petal" of the device, and may generally be located in a proximal region of the device. After passing through a transition region of the device, the elongate member 1802a forms a distal feature 1814a, which may be generally located in a distal region of the device. As can be seen with reference to the distal-end view of FIG. 18, for a given elongate member 1802a, the distal feature 1814a formed by the elongate member 1802a is formed generally offset in a counter-clockwise direction from the proximal feature 1812a formed by the same elongate member 1802a. For example, the distal feature 1814a is generally longitudinally aligned with the proximal feature formed by the second elongate member (elongate member 1802e in this example) arranged counter-clockwise from elongate member 1802a (i.e., there is another elongate member (member 1802f in this example) disposed between the given elongate member 1802a and the second elongate member 1802e) in the counter-clockwise direction when viewed from the distal end of the device. The distal feature 1814 also includes an anchor feature 1816a, which may be a microcoil anchor (e.g., similar to the microcoil anchors discussed elsewhere herein).

Similarly, each of the elongate members 1802b-1802f extends from the proximal eyelet and forms a respective proximal feature in the proximal region of the device, passes through the transition region of the device, and forms a respective distal feature in the distal region of the device. As can be seen with reference to FIG. 18, the six proximal features or petals are generally spaced equidistantly around the proximal eyelet, and in aggregate the six proximal features form an occlusion feature of the frame 1800 (e.g., when the frame or a portion of the frame is covered by a membranous covering). When the proximal features of the frame are covered by a membranous covering, for example, the occlusion feature may be used to occlude an LAA, or other space, hole, defect, aperture, appendage, vessel or conduit within a body of a patient. Similarly, the six distal features are generally spaced equidistantly around the distal eyelet, and in aggregate the six distal features form a support feature of the frame 1800, and in the depicted example include an anchor feature. In some examples, the frame 1800 does not include anchor features 1816. In some examples, one or more of the distal features 1814 (or proximal features 1812) may include an integrated anchor feature (see discussion of FIGS. 14C and 14D above).

As can further be seen with reference to FIG. 18, adjacent elongate members 1802 are wound in different directions, either clockwise or counterclockwise. For example, elongate member 1802a is wound in a counterclockwise direction 1818 from the proximal eyelet (into the page) to the distal eyelet (out of the page), and adjacent elongate member 1802b is wound in a clockwise direction 1820 from the proximal eyelet to the distal eyelet. Similarly, elongate member 1802c is wound in a counterclockwise direction from the proximal eyelet to the distal eyelet; elongate member 1803d is wound in a clockwise direction from the proximal eyelet to the distal eyelet; elongate member 1803e is wound in a counterclockwise direction from the proximal eyelet to the distal eyelet; and elongate member 1803f is wound in a clockwise direction from the proximal eyelet to the distal eyelet. The balanced wind pattern created by winding adjacent wires in opposite directions creates a device that resists a tendency to drift in any direction when deployed because each frame member may counterbalance the frame member adjacent to it, in some implementations. The balanced wind pattern of this frame includes "butterfly" shaped wire patterns for adjacent wires of the device (see e.g., the patterns formed by adjacent wires 1802a and 1802b, or the patterns formed by adjacent wires 1802c and 1802d, or the patterns formed by adjacent wires 1802e and 1802f).

Figure 19:
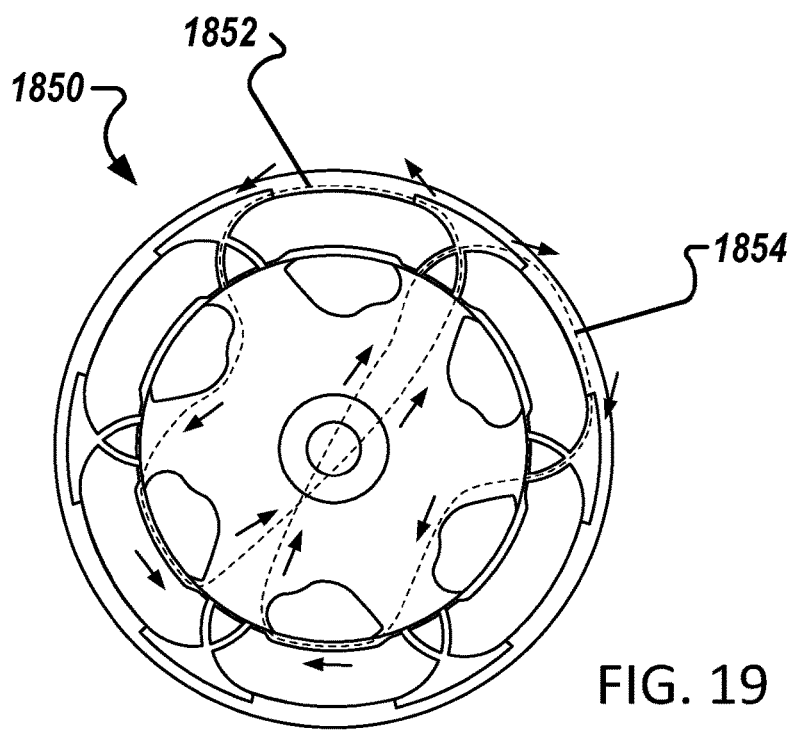
FIG. 19 is a conceptual view of an example winding jig that can be used to wind the frame of FIG. 18.

FIG. 19 is a conceptual view of a winding jig 1850 that can be used to wind the frame 1800 of FIG. 18. Shown in FIG. 19 are winding paths 1852 and 1854 that can be used to wind adjacent elongate elements 1802. For example, elongate element 1802a may be wound using path 1852, and elongate element 1802b may be wound using path 1854. The winding paths 1852 and 1854 also highlight the "butterfly" shape formed by some adjacent elongate members 1802 of the frame 1800, as described above.

The discussion above pertaining to FIGS. 18 and 19 was with reference to a six-wire frame 1800, but in other examples frames having more than six wires (e.g., 8 wires, 10 wires, or 12 wires) may be used. A six-wire frame 1800 may utilize three pairs of starting proximal wires, to form three "butterfly" shapes; a twelve-wire frame 1800 may utilize six pairs of starting proximal wires, to form six "butterfly" shapes.

Figures 20, 21A:
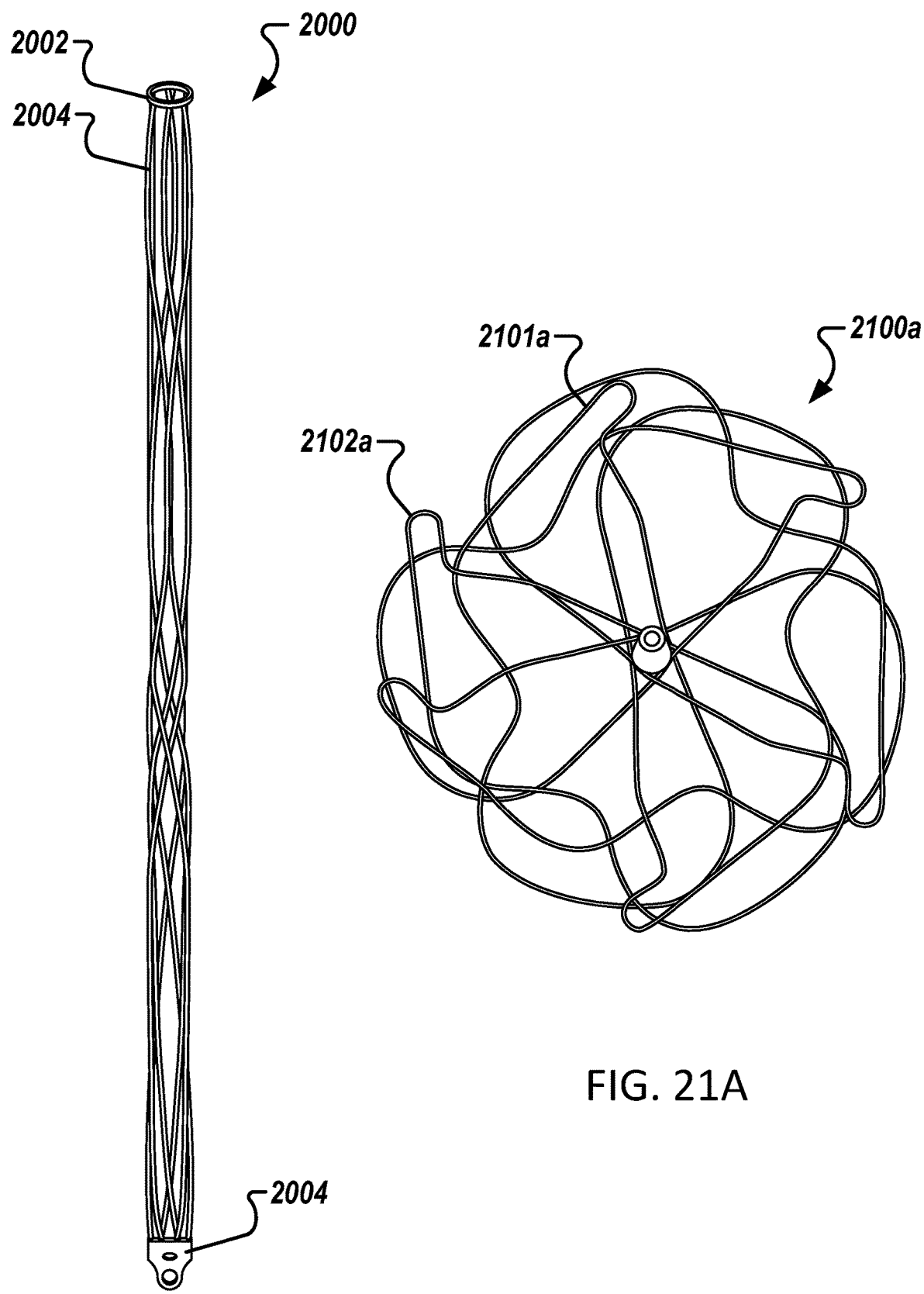
FIG. 20 is a view of an example device frame in an elongated, pre-heat-set configuration, after it was laser-cut from a Niti tube.
FIGS. 21A, 21B, 21C, 21D, and 21E are views of example device frames that include integrated anchor features.
Figure 21B:
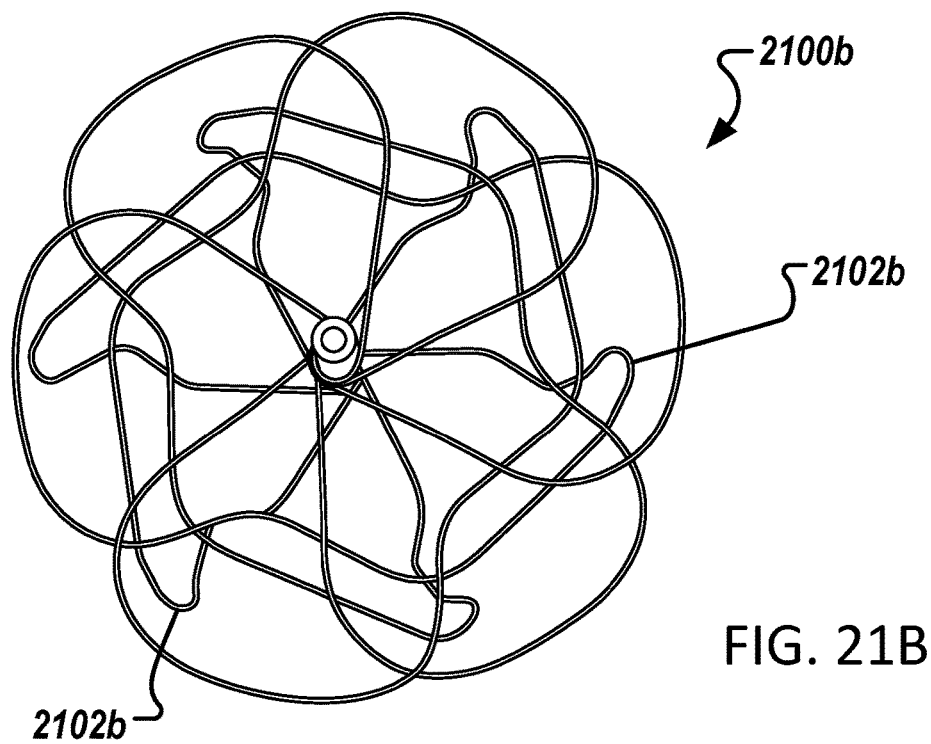
Figure 21C:
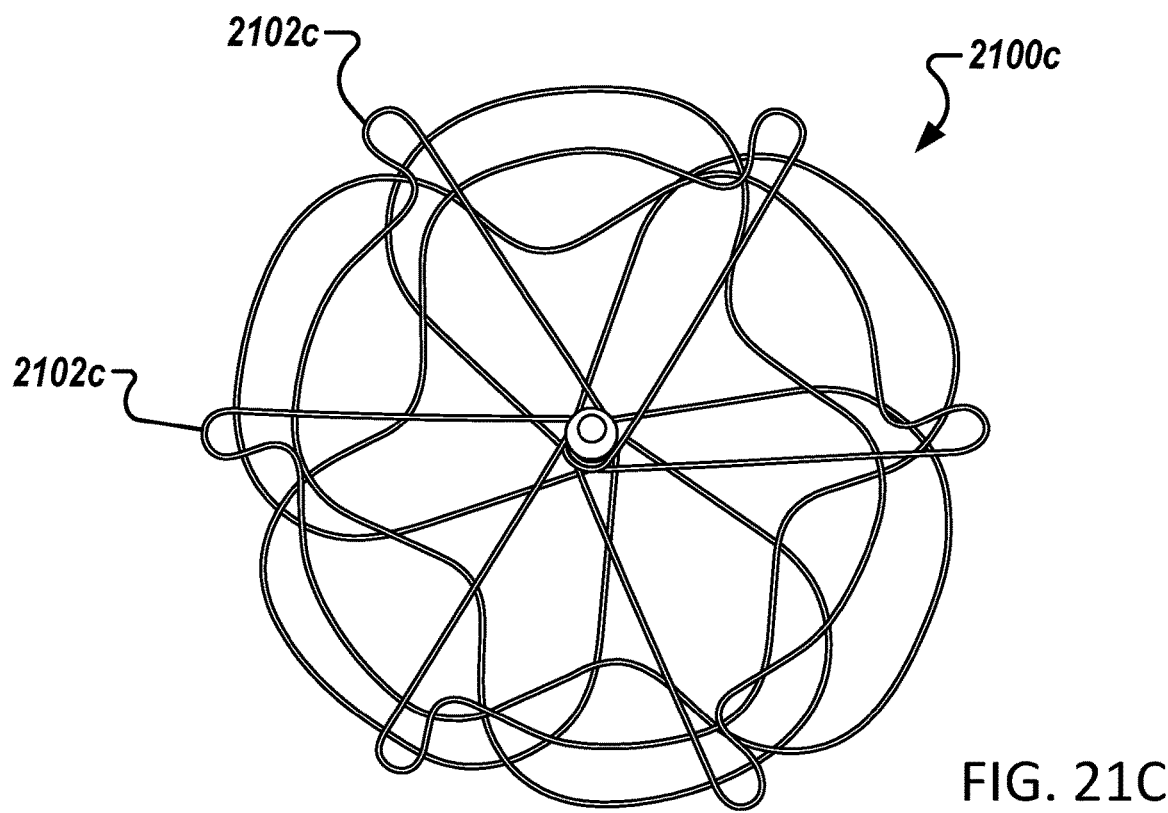
Figure 21D:
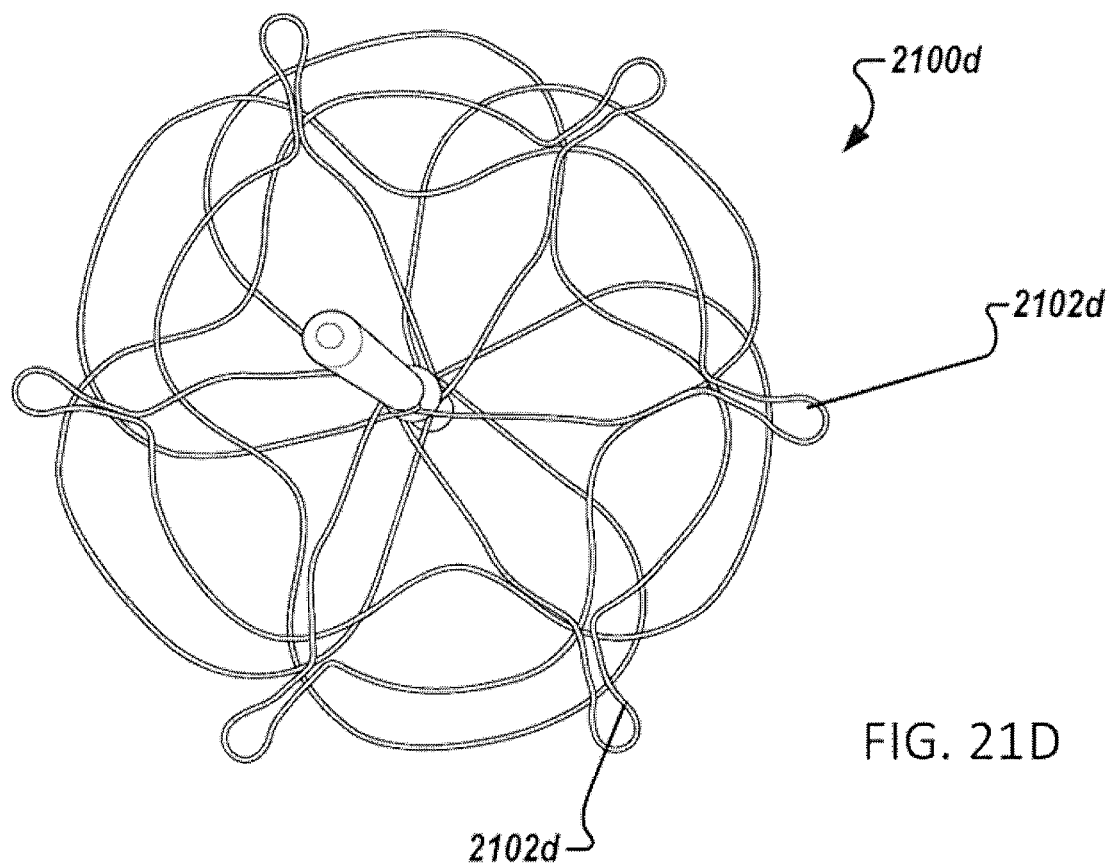
Figure 21E:
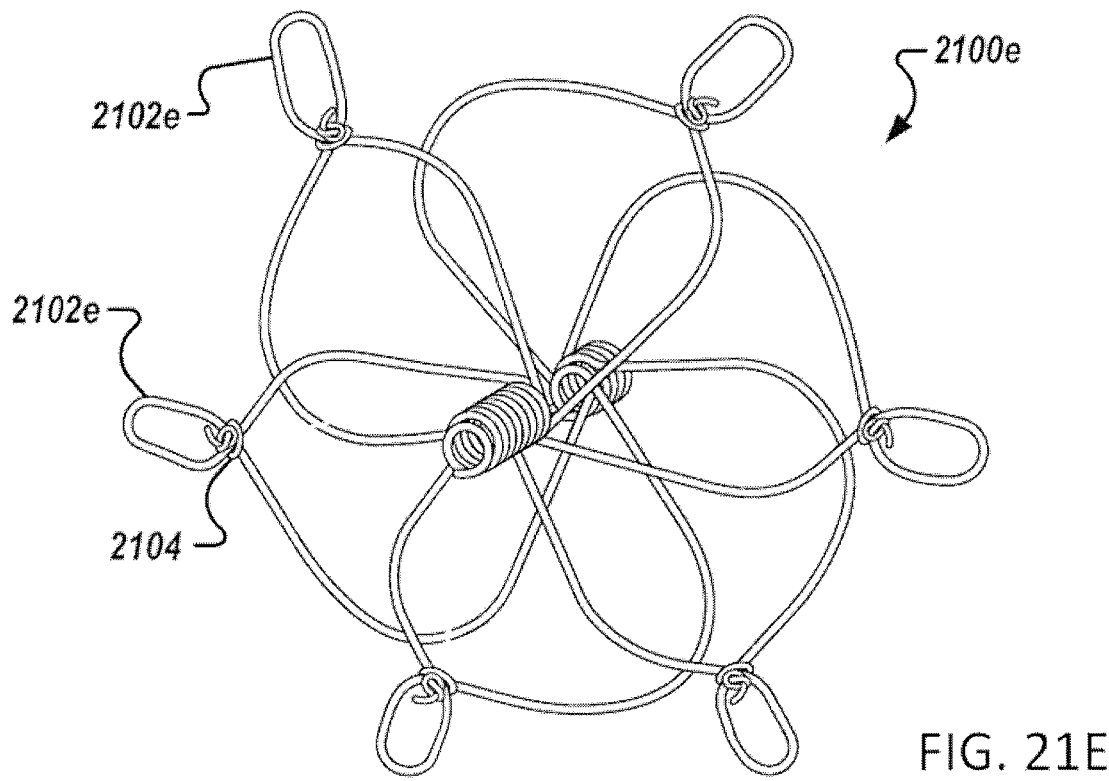

While the example devices discussed herein have generally been described as comprised of elongate elements or wires, in alternative embodiments any of the frames discussed herein may also be formed from a tube, such as laser-cut from a Nitinol tube. For example, a laser may be used to cut a pattern into a hollow tube to create a frame that resembles the wire-based frames discussed herein, where portions of the tube remaining after the pattern has been cut may correspond to the elongate elements or wires of the devices discussed herein. A Nitinol tube having an outer diameter sized to correspond to the eyelet or elongate element aggregation elements discussed herein may be laser-cut in this manner, for example. FIG. 20 is a view of an example device frame 2000 in an elongated, pre-heat-set configuration, just after it was laser-cut from a Niti tube, for example. The frame 2000 includes rings 2002 and 2004 at distal ends of the frame, which may correspond to the eyelets or hub features of the wire-based devices discussed herein. The frame also includes elongate portions 2004 of the tube that can be heat set to a particular configuration so that the elongate portions 2004 form the features (e.g., proximal features or distal features) of the frames discussed herein. The elongate portions 2004 generally terminate at the rings 2002 and 2004. The frame 2000 is intended to depict a general example of how a tube of material may be cut so that remaining portions of the tube may form a frame of devices such as those discussed herein.

While the occlusion devices have been described with respect to an LAA, in some embodiments, the occlusion devices can be used to occlude or seal other apertures within a body of a patient, such as a right atrial appendage, a fistula, a patent ductus arteriousus, an atrial septal defect, a ventricular septal defect, a paravalvular leak, an arteriovenous malformation, or a body vessel.

The examples discussed herein have focused on occlusion devices, but it is contemplated that the features described herein may also be used with other types of medical devices or accessories. Examples of implantable devices and accessories include, without limitation, occlusion and closure devices, filters (e.g. inferior vena cava filter or an embolic protection filter), catheter based grabbers or retrieval devices, temporary filtration devices, stents, stent-grafts, and vessel sizers.

For additional examples of hub features that can be used with the devices discussed herein, see the provisional patent application titled "Joint Assembly for Medical Devices," having inventors Coby C. Larsen, Steven J. Masters, and Thomas R. McDaniel, filed on 16 Nov. 2012, assigned U.S. Ser. No. 61/727,328, and the non-provisional patent application titled "Joint Assembly for Medical Devices," having inventors Coby C. Larsen, Steven J. Masters, and Thomas R. McDaniel, filed on 15 Mar. 2013, the disclosures of which are considered part of and are specifically incorporated by reference in their entirety (including the figures) for all purposes in the present disclosure. For additional examples of delivery system devices, systems, and techniques that can be used to deliver, deploy, reposition, and retrieve the devices discussed herein, see the provisional application titled "Implantable Medical Device Deployment System," having inventors Steven J. Masters and Thomas R. McDaniel, filed on 16 Nov. 2012, assigned U.S. Ser. No. 61/727,328, and the non-provisional patent application titled "Implantable Medical Device Deployment System," having inventors Steven J. Masters and Thomas R. McDaniel, filed on 15 Mar. 2013, the disclosures of which are considered part of and are specifically incorporated by reference in their entirety (including the figures) for all purposes in the present disclosure. For additional examples of delivery system devices, systems, and techniques that can be used to deliver, deploy, reposition, and retrieve the devices discussed herein, see the provisional application titled "Implantable Medical Device Deployment System," having inventors Steven J. Masters and Thomas R. McDaniel, filed on 16 Nov. 2012, assigned U.S. Ser. No. 61/727,328, and the provisional patent application titled "Implantable Medical Device Deployment System," having inventors Steven J. Masters and Thomas R. McDaniel, filed on 15 Mar. 2013, the disclosures of which are considered part of and are specifically incorporated by reference in their entirety (including the figures) for all purposes in the present disclosure.

Several characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. A device for occluding an aperture in a body of a patient, comprising:
    a plurality of wires having proximal end portions and distal end portions;
    a first termination element that is defined by the proximal end portions of the plurality of wires aggregated together;
    a second termination element that is defined by the distal end portions of the plurality of wires aggregated together; and
    a plurality of coil anchors,
        wherein adjacent wires of the plurality of wires are wound in opposite directions to create a balanced frame including
            a first wire of the plurality of adjacent wires extending from the first termination element in a first direction and
            a second wire of the plurality of adjacent wires, adjacent to the first wire, extending from the first termination element in a second direction, and
        wherein each wire of the plurality of wires defines one of first features and one of second features, and
        wherein the plurality of coil anchors are arranged about each of the second features and the second features are at least partially
    circumferentially surrounded by the first features relative to the longitudinal axis of the device and adjacent wires of the second features form a crossing pattern when viewed from one end of the device and along the longitudinal axis of the device, and
    wherein at least one of the plurality of coil anchors comprises:
        a first frame attachment portion extending along the second feature of the first wire, and
        a second frame attachment portion,
            wherein the second frame attachment portion comprises a coil, and
            wherein the coil coils around and covers both the second feature of the first wire and the first frame attachment portion, and
        an anchor portion,
            wherein the anchor portion extends from the first frame attachment portion and the second frame attachment portion,
            wherein the anchor portion includes a first end and a second end, and
                wherein the first end is connected to the first frame attachment portion,
                wherein the second end is connected to the second frame attachment portion, and
                wherein the first end and the second end cross over each other.

2. The device of claim 1, wherein the first wire of the adjacent wires is wound clockwise, and wherein the second wire of the adjacent wires is wound counterclockwise.

3. The device of claim 2, wherein the first wire and the second wire together form a butterfly shape.

4. The device of claim 1, wherein the second feature defined by the second wire of adjacent wires is offset in a counter-clockwise angular direction with respect to the first feature defined by the first wire of the adjacent wires when viewed from the distal end of the device.

5. The device of claim 1, wherein the second feature defined by the second wire is generally longitudinally aligned with a first feature defined by another wire of the plurality of wires.

6. The device of claim 5, wherein a third wire is disposed between the second wire and the another wire.

7. A device according to claim 1, further comprising:
    an occlusive component that includes a plurality of first features that are each defined by a first portion of a respective wire of the plurality of wires, wherein the first features are located in a generally proximal region of the device; and a support component that includes a plurality of second features that are each defined by a second portion of the respective wire of the plurality of wires, wherein the second features are located in a generally distal region of the device.

\* \* \* \* \*